(12) United States Patent
Michelson et al.

(10) Patent No.: US 8,538,774 B2
(45) Date of Patent: *Sep. 17, 2013

(54) METHODS AND SYSTEMS FOR ASSESSING CLINICAL OUTCOMES

(75) Inventors: Seth Michelson, San Jose, CA (US); Timothy Michael Kemp, San Jose, CA (US); Ian Gibbons, Portola Valley, CA (US); Elizabeth A. Holmes, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/609,144

(22) Filed: Sep. 10, 2012

(65) Prior Publication Data

US 2013/0185089 A1 Jul. 18, 2013

Related U.S. Application Data

(60) Continuation of application No. 13/244,762, filed on Sep. 26, 2011, now Pat. No. 8,265,955, which is a division of application No. 12/412,334, filed on Mar. 26, 2009.

(60) Provisional application No. 61/039,721, filed on Mar. 26, 2008.

(51) Int. Cl.
*G06Q 50/00* (2012.01)

(52) U.S. Cl.
USPC ............................................................ 705/2

(58) Field of Classification Search
USPC ............................................................ 705/2
See application file for complete search history.

(56) References Cited

U.S. PATENT DOCUMENTS

| | | | |
|---|---|---|---|
| 5,912,178 | A | 6/1999 | Porter et al. |
| 6,906,320 | B2 | 6/2005 | Sachs et al. |
| 7,017,394 | B2 | 3/2006 | Sullivan |
| 7,255,677 | B2 | 8/2007 | Burch et al. |
| 7,495,537 | B2 | 2/2009 | Tunay |
| 7,574,902 | B2 | 8/2009 | Sullivan |
| 7,713,705 | B2 | 5/2010 | Buechler et al. |
| 7,937,225 | B2 | 5/2011 | Mishra et al. |
| 8,026,049 | B2 | 9/2011 | Assadi-Porter et al. |
| 8,041,090 | B2 | 10/2011 | Alexandrov et al. |
| 8,126,825 | B2 | 2/2012 | Guyon |
| 8,265,955 | B2 | 9/2012 | Michelson et al. |
| 2002/0095260 | A1 | 7/2002 | Huyn |

(Continued)

FOREIGN PATENT DOCUMENTS

| JP | 2005-165987 | 6/2005 |
|---|---|---|
| JP | 2006-346333 | 12/2006 |

(Continued)

OTHER PUBLICATIONS

Shorr, et al. Protein C concentrations in severe sepsis: an early directional change in plasma levels predicts outcome. Crit Care. 2006;10(3):R92. Epub Jun. 15, 2006.

(Continued)

*Primary Examiner* — John Pauls
(74) *Attorney, Agent, or Firm* — Wilson Sonsini Goodrich & Rosati

(57) ABSTRACT

Described herein are methods and systems useful for characterizing clinical outcomes of a subject. Provided herein includes computer-assessed methods, medical information systems, and computer-readable instructions that can aid an end-user in diagnosis, prognosis, and treatment of a clinical outcome.

24 Claims, 39 Drawing Sheets

(56) References Cited

U.S. PATENT DOCUMENTS

| | | |
|---|---|---|
| 2004/0122703 A1 | 6/2004 | Walker et al. |
| 2004/0193019 A1 | 9/2004 | Wei |
| 2005/0119534 A1 | 6/2005 | Trost et al. |
| 2005/0209785 A1 | 9/2005 | Wells et al. |
| 2005/0283380 A1 | 12/2005 | Garduno |
| 2006/0172429 A1 | 8/2006 | Nilsson et al. |
| 2006/0173663 A1 | 8/2006 | Langheier et al. |
| 2006/0241869 A1 | 10/2006 | Schadt et al. |
| 2007/0014343 A1 | 1/2007 | Horneman et al. |
| 2008/0040158 A1 | 2/2008 | Eguchi et al. |
| 2008/0204043 A1 | 8/2008 | Wang et al. |
| 2009/0318775 A1 | 12/2009 | Michelson et al. |

FOREIGN PATENT DOCUMENTS

| | | |
|---|---|---|
| KR | 10-2007-0083810 | 8/2007 |
| WO | WO 2006/094797 A1 | 9/2006 |
| WO | WO 2007/098957 A1 | 9/2007 |

OTHER PUBLICATIONS

European search report and search opinion dated Mar. 24, 2011 for Application No. 9723974.3.

International search report and written opinion dated Jul. 30, 2009 for PCT Application No. US2009/38467.

Office action dated Feb. 8, 2012 for U.S. Appl. No. 13/244,762.

Office action dated Aug. 1, 2012 for U.S. Appl. No. 12/412,334.

Office action dated Nov. 25, 2011 for U.S. Appl. No. 12/412,334.

METHODS AND SYSTEMS FOR ASSESSING CLINICAL OUTCOMES

CROSS-REFERENCE

This application is a Continuation Application of U.S. Ser. No. 13/244,762, filed on Sep. 26, 2011 now U.S. Pat. No. 8,265,955 which is a Divisional Application of U.S. Ser. No. 12/412,334, filed on Mar. 26, 2009, which claims the benefit of U.S. Provisional Application No. 61/039,721, filed Mar. 26, 2008, all of which are incorporated herein by reference in their entirety.

BACKGROUND OF THE INVENTION

Conventional methods for assessing a patient's clinical outcome are primarily based on clinicians' judgment and past experience. The conventional methods generally involve laboratory tests, patient surveys and office visits at isolated time points, all of which are not scalable for a time series analysis, especially for one that tracks or predicts the trend of a patient's clinical outcome in real time. Intrinsic to the conventional methodologies is the profound drawback that a relatively small set of information such as a single clinician's personal preference is taken into consideration in reaching a clinical decision. As such, under the existing medical system, patient care becomes increasingly difficult when multiple variables are involved. In particular, there lacks a system and method to effect a multi-dimensional analysis in which a large set of biomarkers are used to aid in the diagnosis, prognosis, and treatment of a clinical outcome or the design and execution of a clinical trial.

Multivariate statistics are generally concerned with determining a statistical distribution of an outcome or a series of outcomes based on multiple variables. Inherently, most medical conditions and treatments are multivariate due to the complexities of the physiology. The discoveries of a vast number of disease biomarkers and the establishment of miniaturized analytic systems have made a new paradigm of patient care that makes multivariate analysis feasible. A desirable new paradigm would provide rapid access to information characterizing clinical outcome and then automatically linking that information through customized communication channels so that the desired medical actions (adaptive dose ranging, clinical decision making and so forth) can be performed. Also desirable is the ability to integrate information from an individual's blood tests with other physiologically relevant factors, and present that information in an actionable format. The technology described herein satisfies these needs and provides related advantages as well.

SUMMARY OF THE INVENTION

The present invention provides a medical information system for subject data analysis. In one aspect, a system of the present invention is particularly useful for advancing the future of blood testing and data analysis. For example, the system can be part of an integrated infrastructure built around real-time, point-of-care consumer blood monitoring devices which analyze a small blood sample (e.g., 500 ul, 50 ul, 25 ul, 10 ul or even less) and wirelessly transmit that information to a database which integrates real-time data with stored data from disparate databases (patient record, genetic/genomic information, data from pivotal trials) into one central repository. The system then allows for the automatic application of multivariate, multidimensional mathematics to the data repository to perform specific commands or tasks, e.g., mapping real-time PK/PD dynamically in the context of the pathophysiology of a given medical condition.

In another aspect, a system of the present invention can be used to improve the label of key drugs through adaptive clinical studies which generate publications for label expansions for new indications, patient subpopulations, and for ameliorating safety concerns. The development of such a system for home, real-time blood monitoring has significant implications which allow one to collect information which is otherwise not available through the use of the conventional laboratory testing.

The medical information system typically comprises (a) an input device for receiving subject data and in communication with a processor; (b) storage unit in communication with the processor having a database for: (i) storing data corresponding to a probability space defined by a set of discrete clinical outcomes, each of which is characterized by statistical distribution of at least one biological marker; and (ii) storing subject data corresponding to the at least one biological marker; (c) a processor that calculates the position of said subject data in said probability space as a way of assessing the probability of a discrete clinical outcome of said subject; and (d) an output device that transmits information relating to the discrete clinical outcome of c) to an end user.

Non-limiting clinical outcome that the system is adapted to predict can be selected from the group consisting of but not limited to: complete response (CR), partial response (PR), stable disease (SR), non-response (NR), adverse drug effect (ADR), and drug toxicity. In using the medical information system, the end user can be a medical personnel or the subject himself or herself. In some instances, the end user is from a pharmaceutical company.

In one aspect, the processor of the system calculates the position of said subject data in said probability space as a way of assessing the probability of a discrete clinical outcome of said subject.

In another aspect, the input device of the system comprises a touch screen. Where desired, the input system can comprise a data entry portal or a keyboard. The subject data to be input into, processed by, or transmitted as an output by the system can be textual, numeric or a category. Where desired, the textual or numeric information is solicited from the end user.

In some instances, the subject data represent measurements of the at least one biological marker present in a bodily fluid. In some instances, the measurements are obtained by a point-of-care device that is operated by the subject. The measurements can be taken at various time points to yield a trajectory within the probability space, wherein said trajectory represents a time series of the assessed clinical outcome. The various time points can cover a period of less than or about 24 hours In another aspect, the medical information system comprises an output device having an automatic alert system. The automatic alert system can be programmable by the end user. Where desired, the automatic alert system is programmable based on a predefined protocol for a clinical trial. In another aspect, the output device of the system transmits selected portions of the subject data and the probability space in response to instructions from the end user. In yet another aspect, the information transmitted by the output device is encrypted. In still another aspect, the information transmitted by the output device represents an assessment of the clinical outcome of said subject at a single time point. The information transmitted by the output device can represent a time series of the assessed clinical outcome.

In still another aspect, the input device and/or the output device of the system comprises a user interface that can remotely access the network.

In yet another aspect, the medical information system comprises a network.

In yet another aspect, the storage unit of the system stores historical reference data of a plurality of subjects in relationship to the at least one biological marker. Where desired, the data stored in the storage unit are selected from the categories consisting of pathology, anatomy, treatment option, treatment outcome, pharmacological parameter, pharmacokinetics parameter, psychological parameter, and genomic information. The database can be public, internal.

The end user of the medical information system can be a health care provider, including without limitation a Health Maintenance Organization (HMO).

The present invention further provides a method for characterizing the probability of a clinical outcome of a subject. The method comprises the steps of (a) constructing a probability space defined by a set of discrete clinical outcomes, each of which is characterized by a statistical distribution of at least one biological marker; (b) obtaining subject data corresponding to the at least one biological marker; and (c) calculating the position of said subject data in said probability space, thereby characterizing the probability of the clinical outcome of said subject.

Also provided is a method of characterizing a clinical outcome of a subject comprising: (a) constructing a probability space within a server, wherein the probability space is defined by a set of discrete clinical outcomes, each of which is characterized by the statistical distribution of at the least one biological marker; (b) entering data of a subject into the server, said data corresponding to the at least one biological marker; and (c) calculating the position of said subject data in said probability space thereby characterizing the clinical outcome of the subject. In some embodiments, in practicing the subject methods, at least steps b and c are repeated at various time points to yield a trajectory within a probability space, wherein said trajectory is indicative of the likelihood of progression to the clinical outcome. The subject methods can comprise the step of notifying a medical personnel or the subject of a need for taking a medical action upon assessing or characterizing the position of said subject data in said probability space. In some instances, the medical action involves at least one action selected from the group consisting of altering a dosage of an existing therapeutic agent administered to said subject, administering a different a therapeutic agent, and administering a different combination of therapeutic agents. Notification of a medical action can be electronically transmitted, e.g., wirelessly transmitted. The subject methods can further comprise step of, upon selection of the at least one action, performing an outcome analysis for assessing a result of said selected action, and automatically updating the probability of a discrete clinical outcome of said subject.

Further provided in the present invention is a computer readable medium comprising computer readable instructions, which when executed cause a processor to: a) provide a probability space defined by a set of discrete clinical outcomes, each of which is characterized by a statistical distribution of at least one biological marker; b) obtain subject data corresponding to the at least one biological marker; and c) calculate the position of said subject data in said probability space to assess the probability of a clinical outcome of said subject. In general, the instructions operate in a software runtime environment. In one aspect, the instructions when executed further causes a processor to provide a user defined alert condition based on an assessment of trajectory parameters of the subject data in the probability space, wherein said trajectory parameters are at least one of speed, acceleration, direction, and position.

In an aspect, a method is provided herein of predicting the occurrence of a medical condition that requires medical intervention, the method comprising: (a) measuring concentrations of a first set of biomarkers present in a subject and measuring one or more physiological indicators of said subject at a given frequency, wherein the first set of biomarkers are suspected to be predictive of the medical condition; (b) based on the concentrations measure in (a), generating from the first set a subset of biomarkers that are more correlative with the occurrence of the medical condition and/or a new frequency of measurement of the biomarkers; and (c) measuring concentrations of the subset of (b) and/or following the new frequency of measurement of one or more biomarkers, thereby predicting the occurrence of the medical condition.

In some instances, a method further comprises analyzing data reflecting the concentrations and/or the physiological indicators with multivariate statistical software. In some instances, the biological markers are present in a biological sample of said subject. The biological sample can be diluted by an appropriate fold to ensure, e.g. the appropriate range of concentration level is detected.

In another aspect herein, a method of monitoring sepsis development of a subject comprises: measuring at least two parameters selected from the group of (1) body temperature of said subject, (2) protein C concentration of said subject, (3) interleukin 6 (IL-6) concentration of said subject, multiple times to yield a trend of temperature, protein C trend, and/or IL-6; and wherein an increase beyond normal body temperature, a decrease in protein C concentration and/or an increase in IL-6 concentration is indicative of the development of sepsis in said subject. In some aspects, a decrease in protein C and an increase of IL-6 can be indicative of the development of sepsis in said subject. In some other aspects, a decrease in protein C and an increase of IL-6 and an increase beyond normal body temperature can be indicative of the development of sepsis in said subject. In some instances, an at least about 10-fold increase in IL-6 concentration in said subject is indicative of the occurrence of sepsis in said subject. In a further instance, an at least about 100-fold increase in IL-6 concentration in said subject is indicative of the occurrence of sepsis in said subject. This method may further comprise the step of increasing frequency of measuring IL-6 concentration upon an increase beyond normal body temperature and/or a decrease in protein C concentration. For example, the frequency of IL-6 measurement can be increased to once a day, once every 12, 8, 6, or 4 hours. A determination of the occurrence of sepsis may be promptly followed by an appropriate medical intervention.

Also described herein is a method for characterizing a medical condition of a subject, comprising: obtaining a first set of subject data comprising at least one biological marker and at least one physiological parameter from the subject; determining the probability of a medical condition of the subject using the first set of subject data obtained; selecting a second set of subject data from the probability of the medical condition; and obtaining the second set of subject data from the subject, thereby characterizing the medical condition of the subject.

In yet another aspect, a method is disclosed for characterizing periodicity of a clinical condition of a subject, the method comprises: identifying a set of biomarkers for a clinically relevant condition; obtaining longitudinal subject data corresponding to at least one biomarker in said set to obtain a trend of the subject data; analyzing said trend to identify periodic changes in the at least one biomarker; measuring values of peak measurements of the periodic changes of the trend; and characterizing the values of the peaks thereby characterizing the periodicity of the clinically relevant condition. In some instances, the analyzing step comprises developing an ARIMA model to determine a differencing lag in the underlying model. The differencing lag can be used to detrend the trend and establish a stationary trend. In some instances, the analyzing step comprises calculating an autocorrelation function and the measuring step comprises identifying the statistically significant peaks in the autocorrelation function. In some instances, the analyzing step comprises calculating spectral density and the calculating spectral density is performed using a Fast Fourier Transform. The measuring step can comprise identifying the power spectrum of the maximum spectral density frequency.

In an aspect described herein, a method for monitoring subject response to therapy comprises: obtaining longitudinal subject data corresponding to at least one biomarker in a set of biomarkers for a clinically relevant condition to obtain a trend of the subject data, wherein the subject data is obtained from a subject receiving a therapy; monitoring periodicity of the trend; and corresponding the periodicity to a response to the therapy received by the subject. In some instances, the therapy is a periodic dosing regimen. In some instances, the response to the therapy is characterized by a time-dependent behavior of peak levels of the trend. In some instances, the time-dependent behavior is substantially constant. In other instances, the time-dependent behavior is changing linearly. In yet other instances, the time-dependent behavior is changing exponentially.

In an aspect, a method is disclosed herein for characterizing the emergence of clinically relevant subpopulations of patients exposed to a therapeutic agent, the method comprising: identifying a set of biomarkers in a blood sample that act as surrogate markers for the therapeutic agent; measuring the set of biomarkers longitudinally from a group of patients exposed to the therapeutic agent; identifying distinct clusters in a multivariate clustering space of the measured values of the set of biomarkers from the group of patients; determining the rate of separation of the distinct clusters and measuring the distance between the distinct clusters in a statistical manner; obtaining patient information from the group of patients to classify the patients in clinically relevant subpopulations; and comparing the distinct clusters to the clinically relevant subpopulations to characterize sensitivity and specificity of the distinct clusters to predict the clinically relevant subpopulations. In some instances, the method further comprises identifying a second set of biomarkers configured to improve the characterization of the emergence of distinct clusters to predict the clinically relevant subpopulations. In some instances, the group of patients exposed to the therapeutic agent are participants in a clinical trial. In some instances, the clinical trial is a dose ranging trial. In other instances, the clinical trial is a part of an adaptive clinical trial. The adaptive clinical trial can be designed to characterize an optimal dosing regimen or can be designed to characterize an optimal responder population. In some instances, the measuring the distance step comprises measuring the Mahalanobis distance between the distinct cluster centroids. In other instances, the measuring the distance step comprises measuring the nearest-neighbors distance between the distinct clusters. In yet other instances, the measuring the distance step comprises measuring a Euclidean distance measure between the distinct clusters. In some instances, the measuring the distance step measuring a Manhattan distance measure between the distinct cluster.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

Many features of the invention are set forth with particularity in the appended claims. A better understanding of the features and advantages of the invention will be obtained by reference to the following detailed description that sets forth illustrative embodiments, in which many principles of the invention are utilized, and the accompanying drawings of which:

DETAILED DESCRIPTION OF THE INVENTION

Figure 1:
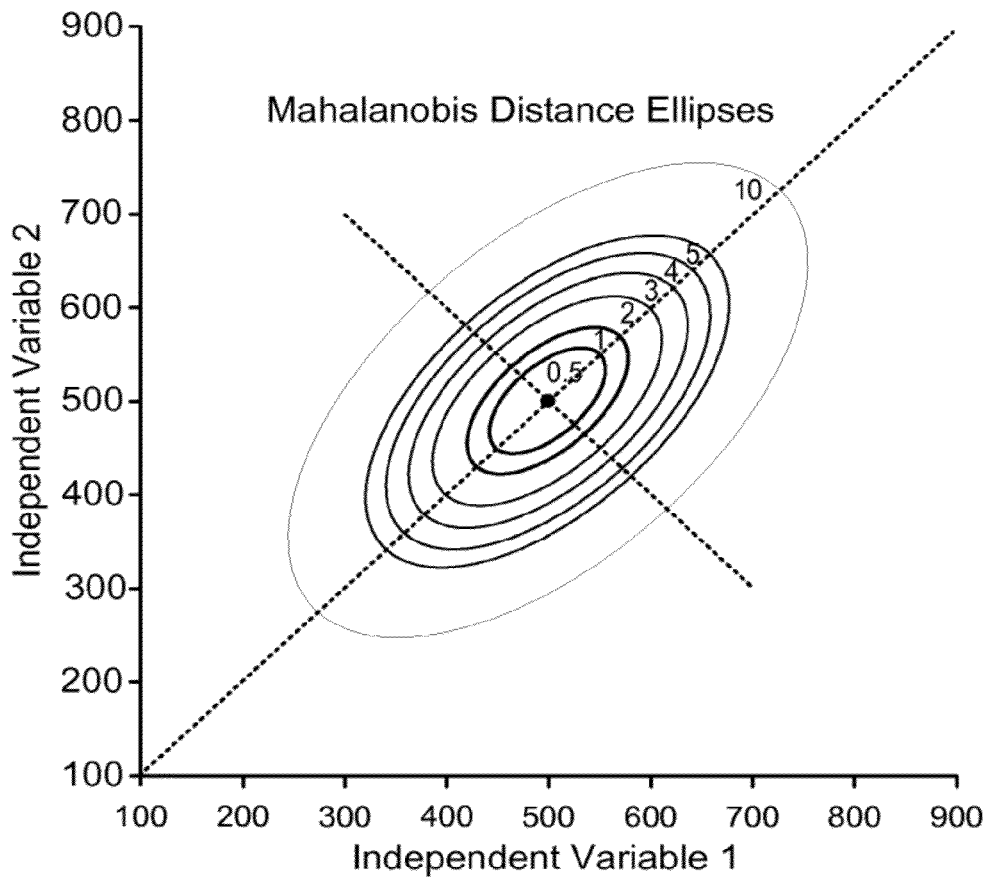
FIG. 1 illustrates a general representation of the Mahalanobis distance method and the representative ellipses. The figure also includes the Mahalanobis distance mathematical equation.

In one embodiment, a method is provided herein for characterizing the probability of a clinical outcome of a subject. The method comprises the steps of (a) constructing a probability space defined by a set of discrete clinical outcomes, each of which is characterized by a statistical distribution of at least one biological marker; (b) obtaining subject data corresponding to the at least one biological marker; and (c) calculating the position of said subject data in said probability space, thereby characterizing the probability of the clinical outcome of said subject.

In practicing the methods herein, one generally utilizes a set of biological markers (also referred to herein as biomarkers) relevant to a given clinical outcome. In order to improve the reliability and accuracy of a mathematical calculation, biomarkers are selected based upon multivariate statistics from data pertaining to a clinical outcome, whether it being, for example, a disease or a medical procedure. In some embodiments, discriminant analysis is performed to determine the most relevant biomarkers pertaining to a particular medical clinical outcome.

In an aspect, a method is provided herein of predicting the occurrence of a medical condition that requires medical intervention, the method comprising: (a) measuring concentrations of a first set of biomarkers present in a subject and measuring one or more physiological indicators of said subject at a given frequency, wherein the first set of biomarkers are suspected to be predictive of the medical condition; (b) based on the concentrations measure in (a), generating from the first set a subset of biomarkers that are more correlative with the occurrence of the medical condition and/or a new frequency of measurement of the biomarkers; and (c) measuring concentrations of the subset of (b) and/or following the new frequency of measurement of one or more biomarkers, thereby predicting the occurrence of the medical condition.

Pluralities of discrete clinical outcomes, sometimes referred to as medical outcomes, for a specific medical condition are plotted in a geometrical manner. A set of values of the biomarkers are chosen that are the most representative of each clinical outcome. Using the mathematical methods described herein, probabilities of class assignment to each discrete clinical outcome can be assigned to any set of values of observed biomarkers. A probability space can then be constructed by plotting the probability of any set of values of observed biological markers within the geometric space defined by the plurality of discrete clinical outcomes.

Model Building

In some instances, mathematical modeling describes the dynamic state of a system. In some instances, the models use a system of equations representing outcome parameters, biomarker and drug concentrations and the like over time. Such equations might be simple enough to solve in closed form, yielding an algorithmic formula. However, in some instances, models of human disease can be too complex to permit a simple closed form solution. In some instances, a solution as described herein can be projecting numerical solutions forward in time, also known as termed predictive biosimulation.

The objective of cluster analysis is to group observations into clusters such that each cluster is as homogeneous as possible with respect to the clustering variables. Any conventional clustering algorithm may be used to define the discrete set of clinical outcomes based upon the recognized biomarkers. Besides the Discriminant Function Analysis, there are many such algorithms, such as "Single Linkage," "Complete Linkage," "K means," "Ward's Method," or the "Centroid Method." Additionally, one can identify clusters using "Decision Trees". These algorithms are well-known to anyone familiar with the art, and are available in standard statistical packages such as SAS and SPSS. The clustering algorithms group like objects together, and keep unlike objects in separate groups.

Multivariate statistics to identify classes of similar subjects in a sample population can also be applied for building an appropriate model. The techniques currently employed include, but are not limited to, Discriminant Function Analysis (DFA), Hierarchical Clustering Analysis, Factor Analysis (in which an underlying model or relationship is assumed), Self-Organizing Maps (SOMs), Support Vector Machines (SVMs), and Neural Nets. Each is a pattern recognition technology using multivariate descriptor vectors, which subjects are classmates, to more completely manage an adaptive clinical trial.

Other techniques estimating the model parameter space include several conventional methods, such as the graphical method and gradient-based nonlinear optimization (Mendes and Kell, 1998). The graphical method is typically applied to those problems that can be converted to linear regression problems, and are generally not amenable to closed-loop learning as they require human intervention at each step. The gradient-based nonlinear optimization method does not have such a restriction; however it does require information about the error function with respect to the parameter estimates. As such it often converges to local minima. Evolutionary algorithms including genetic algorithms, evolutionary programming, genetic programming, and their variants (Back et al., 1997; McKay et al., 1997; Edwards et al., 1998) have been applied to overcome these limitations.

In some instances, to best account for the dynamics of a biological system, the equation systems discussed above can be composed of ordinary differential equations which calculate the rate of change of a biological entity over a fixed time segment. That quantification is a function of the state of the system at the instant of analysis, and includes terms for all other entities in the system that might affect that rate of change.

In many instances, as described herein, biological entities of interest are found in blood comprising but not limited to circulating proteins. In the modeling space, the time rate of change of each biological entity is called the derivative and is quantified as the instantaneous slope of the biological entity's concentration curve in the time domain.

The value of any selected target biological entity at each selected sampling time point can be calculated as well as the rate of change for every entity in the sampling space. This can result in a point estimate per biological entity for the derivative in units comprising but not limited to a change in concentration per unit time.

In some instances, a method can utilize two point slopes along with a K-point model fitting regression equations through the last K observations, to estimate the first, second, and higher order derivatives, for example:

$$dP(t)/dt = f(P(t), \{\text{other proteins, cells types, etc.}\}, \text{model parameters})$$

where P(t) is the concentration of a given protein as a function of time. And where f is function of P(t) and entities affecting specific protein concentration curves, comprising second signals, cell numbers, and the like. And where model parameters are coefficients in those equations that quantify those relationships, for example comprising production rates and clearance rates. The system can be linear or non-linear.

An alternate embodiment of the mechanism is a system of entities where P(t) is a protein vector $\Pi(t)=[P_1(t), P_2(t), \ldots P_N(t)]$ where N is the number of proteins chosen to sample, and $\beta(P, \text{etc.})$ becomes a matrix $M(\Pi(t); \beta(\Pi(t))$. The system parameters become a vector as $\beta(\Pi(t))$.

For example, clearance rates of each PM) in the vector $\Pi(t)$ are captured in this vector form. $\beta(\Pi(t))$ characterizes the functional coefficients of the matrix M. The system is linear when $\beta$ does not depend on $\Pi(t)$ or on time. The system is linear and parametrically time-dependent when $\beta$ depends on t, and varies linearly with time.

In another example, the system is nonlinear when the clearance rate changes with time and can represent the up-regulation or down-regulation in time. The system is represented but is not limited by the vector equation:

$$d\Pi(t)/dt = M(\Pi(t); \beta(\Pi(t))^*\Pi(t)$$

In yet another example, the dynamic state of biological systems has a level of specificity which is captured in an exemplary biosimulation system. Every entity in the system will typically act on a small subset of other entities. For example, protein 2 modifies the rate of production of protein 1 by binding to a cell surface receptor on an activated effector cell. The concentration of protein 2 modifies the rate of production of protein 1. When a third protein acts on the production of protein 2 the rate of production of protein 1 depends indirectly on the level of production of protein 2.

The equations that best represent the above example in this biosimulation system are:

$$dP_1/dt = \beta_{12} P_2(t)$$

$$dP_2/dt = -\beta_{22} P_2(t) + \beta_{23} P_3(t)$$

$$dP_3/dt = 0$$

In these exemplary equations, the concentration of Protein 3 is constant and the rate of Protein 1 production is an increasing function of the Protein 2 levels, factored by $\beta_{12} > 0$. In addition, the levels of Protein 2 are a function rate Protein 2 is cleared from the system, in this case, proportionally by a factor $\beta_{22} > 0$, and the effects of $P_3(t)$ on its production, described by a factor $\beta_{23} > 0$ and is parameterized by the vector $(\beta_{12}, \beta_{22}, \beta_{23})$. Any triplet vector can be used in the general case to generate any family of trajectories in time for Proteins 1 and 2. Protein 3 is non-varying in this model since its derivative remains zero.

By measuring Proteins 1 and 3 at each time point in a monitoring period, values for $P_1(t)$, and $P_3(t)$, and estimates for $dP_1/dt$ and $dP_3/dt$ are obtained. $P_2(t)$ can then be solved and constrain the solution set to a parameter vector $(\beta^*_{12}, \beta^*_{22}, \beta^*_{23})$, which is defined by well defined algebraic equations. Estimates of both $P_2(t)$ and $dP_2/dt$ derive the state of the constrained system based on point estimates as derived from the samples. This allows for projecting forward in time where a model trajectory will likely be at the next sample point, and re-adjustment of the model parameters as necessary in a dynamic feedback self-correcting system.

The self-correcting mechanism and feedback system can be implemented in a periodically sampled measurement space, and that model refinement and re-parameterization can take place at each sample interval. After each application of this self-correcting methodology, the space of acceptable parameter vectors should begin to converge to a patient specific vector that projects forward in a predictive trajectory.

A system that dynamically characterizes patient subpopulations based on the longitudinal sampling of predictive protein profiles can use that information as a Type 1 biomarker to verify to the researcher scientist that the compound is acting on the target as expected. The mechanism of action for that compound can also be researched for whether it is acting as expected. Characterization of the dynamic emergence of the subpopulations is based upon their behaviors and the protein profiles they exhibit.

In an example, one population is treated with the test compound while another is an untreated control. If the protein profiles of the treated population behave in accordance with the underlying hypothesis as it pertains to the compound's mechanism of action, the protein profiles will, as a conglomerate pattern, act as a Type 1 biomarker. If individuals within that population show considerable variance in both the direction and velocity of the protein profile, adjustment of the doses of the slower population members can occur and the trial protocol can be changed accordingly.

A variety of statistical analyses are applicable for building a probability space or model. FIG. 1 illustrates an exemplary characterization of similarity as measured by the Mahalanobis distance in a two-dimensional (multivariate) space. The outcome of a discriminant function analysis is typically a Mahalanobis distance for every subject in the analysis data set. The methods of performing the discriminant analysis in this manner or similar manners are known to those skilled in the art. In this example, the data from two independent variables (for example, biomarkers) are plotted against each other. Each patient in the analysis set is represented by a single point on the graph. The distance between each patient's biomarker pair pattern and the centroid of the cluster of data is calculated as the Mahalanobis distance and is represented by the ellipses in the FIG. 1, wherein the centroid can be typically defined as the mean sector of all independent measures in the space of interest. The probability that any particular patient belongs to a cluster depicted herein is inversely proportional to the distance from the centroid of the cluster. In this way the Mahalanobis distance ellipse on the plot in FIG. 1 is used as a measure of similarity between the two sets of independent variables. This method also accounts for noise in the appropriate distance metric by assigning probabilities of class assignment for a particular patient based on the variance observed in the underlying clustered data. Thus this method can account for uncertainty in the probability space.

In conventional clustering, one typically works from a distance matrix, which lists the similarity of every object to be clustered versus every other object. The process begins with the creation of the distance matrix as known to one skilled in the art. A triangular matrix of distances among all pairs of patients must be computed. Each of the distances between subject data will be a function of the measured biomarkers. The function would take the form of a sum or weighted sum. The distances for a given variable are, in turn, a sum of distances between individual observations for that variable. This sum also may be weighted. For example, each cluster of subjects potentially represents a discrete clinical outcome.

The distance matrix metric can include calculating a statistical difference, such as the Mahalanobis distance, Euclidean distance, and Manhattan distance. The matrix represents, in a statistically rigorous way, the similarity of two multivariate patterns in a multidimensional space. Based on these distances, individuals are grouped together in a cluster.

Figure 2:
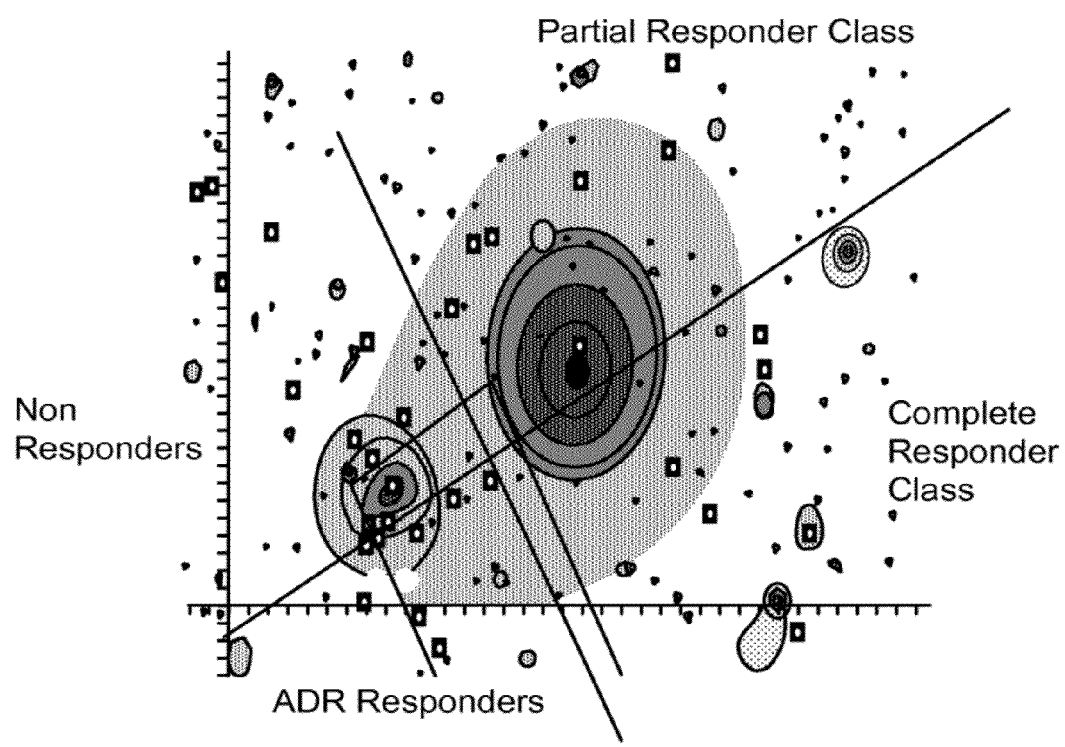
FIG. 2 illustrates an example of the results of a cluster analysis of a clinical outcome.

FIG. 2 illustrates an exemplary clustering method of defining the discrete clinical outcomes. In this example, the centroid method was used to determine multiple centroids of biomarker data patterns. Each centroid either defines or belongs to a different set of discrete clinical outcomes based upon measured biomarker information. In FIG. 2, examples of the classification of biomarker patterns of a medical condition include a partial responder class, a non-responder class, a complete responder class, and an adverse drug reaction class. Every data point is related to a centroid of the class it falls within. The centroid can be set to be the point most representative of the class.

After the distance matrix has been constructed and discrete clinical outcomes have been defined by a set of biomarkers, a probability space can be constructed from multivariate distributions (for example, clusters) by applying a metric that accounts for the variance-covariance structure of the data. Based upon the measured distance, a probability for class assignment for any observed biomarker pattern is calculated. The calculated probability for any obtained biomarker pattern defines the probability space.

Where desired, a probability measurement is carried out by way of a Bayesian calculation. Other methods of calculating the probability for class assignment include, but are not limited to, Nelson-Aalen estimation, the ordinary least squares estimation, the weighted least squares estimation, and the maximum likelihood estimation. Another method is to use a decision tree analysis and from the measure determine the ultimate sensitivity and specificity of the derived rule.

Figure 3:
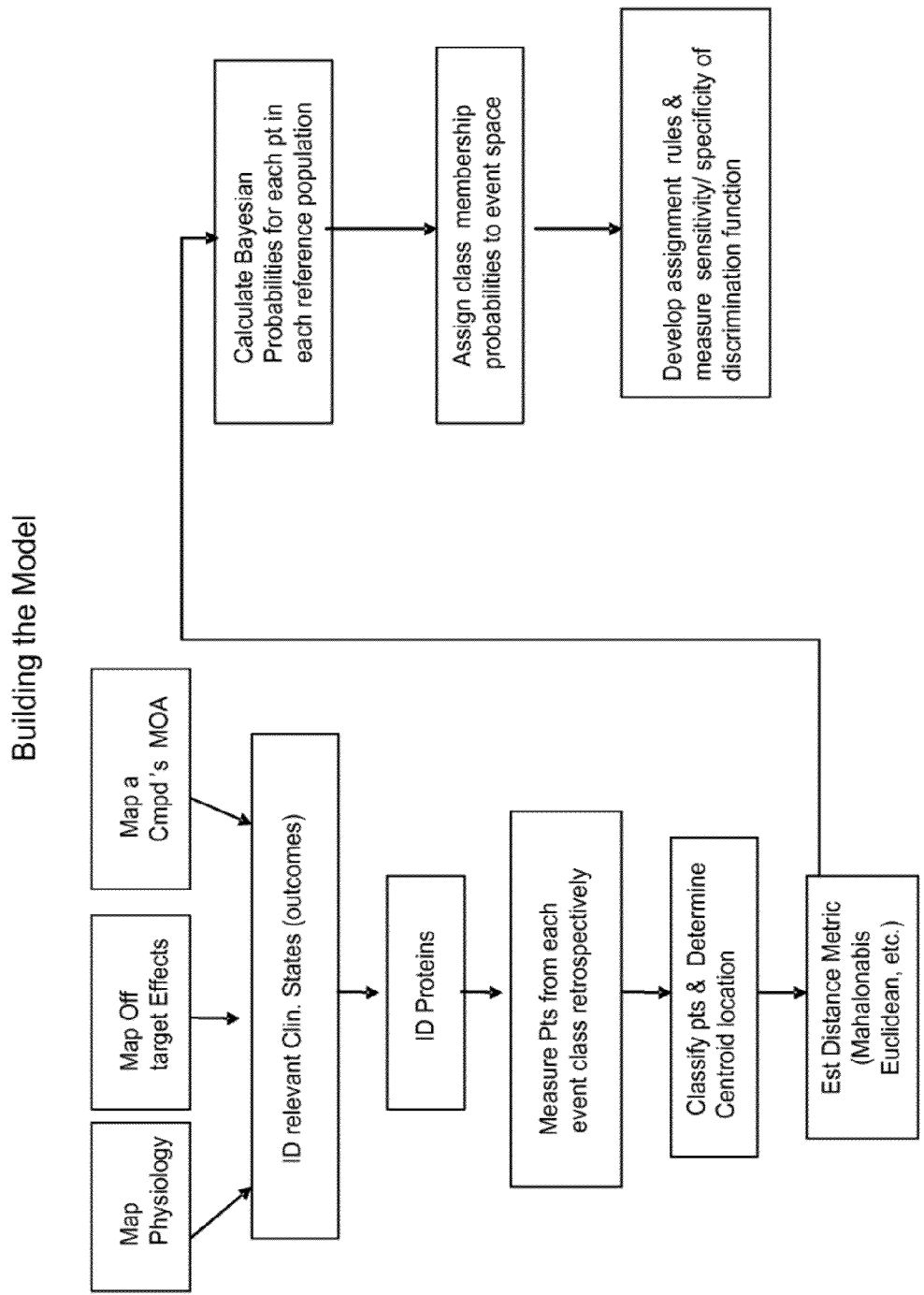
FIG. 3 is a flow chart illustrating an exemplary method of assessing a clinical outcome of a subject and assigning probabilities thereto.

FIG. 3 illustrates an exemplary method of the invention of building a mathematical model for assessing a medical condition. Based upon prior history of a medical condition, a user (for example, a physician) identifies the relevant clinical outcomes or outcomes. The physiology, a compound or drug's method of action, and/or off target treatment effects are then utilized to help define the borders of a probability space.

Figure 4:
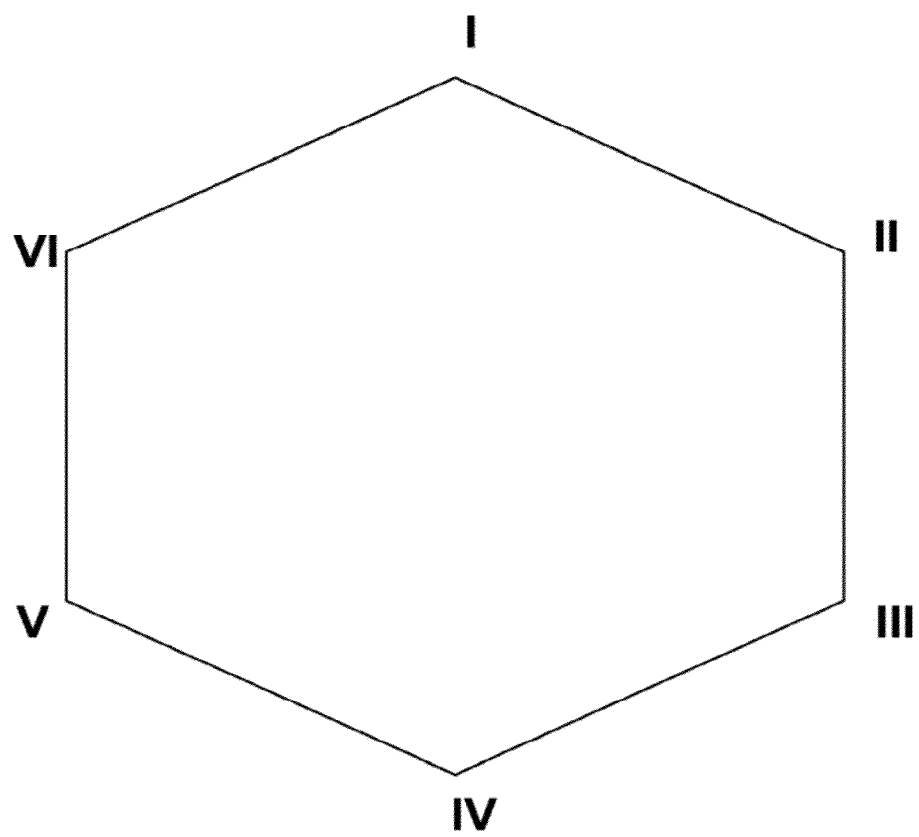
FIG. 4 illustrates an example probability space geometrical representation.

A graphical example of the probability space and the discrete clinical outcomes that define the borders of the probability space are illustrated in FIG. 4. Each number represents a different clinical outcome.

Biomarkers that are most relevant to the clinical outcomes of a given medical condition are identified using multivariate discriminant analysis. Data from the set of biomarkers are classified according to the discrete clinical outcome to which the independent data is most closely correlated.

After the data sets are classified by cluster analysis and/or discriminant function analysis and identified as clinical outcomes, the centroid location of a clinical outcome is determined. For each reference point or independent biomarker data point, a probability of classification into each reference clinical outcome is assessed.

When data from an individual subject is obtained corresponding to at least one biomarker, the data is input into the mathematical model and its geometrical position within the probability space is determined. A distance metric is then used to determine the position of the subject data with reference to each clinical outcome. In a preferred embodiment, the distance metric is the Mahalanobis distance. For the subject data, the model obtains a distance metric corresponding to each discrete clinical outcome.

A statistical estimation method is used to convert the plurality of distance metrics into a plurality of probabilities for the subject data. Each probability of the plurality of probabilities corresponds to a discrete clinical outcome. In an embodiment, the statistical estimation is a Bayesian estimation. The plurality of probabilities is used as the coordinates of the subject data in the geometric probability space, such as the one illustrated in FIG. 4. The position of the subject data within the probability space is an assessment of the medical condition of the subject.

Rules can be assigned by the user (for example, medical personnel) to any point in the probability space. The rules may guide the user in understanding the subject's current medical condition and guide the user in selecting a course of action.

The methods described herein can be performed at any point in time during observation of the subject. Subject data can be obtained at various time points. The position of the subject data in the probability space can then be calculated using the mathematical methods described herein. The steps of obtaining and calculating the position of subject data in a probability space can be repeated to yield a trajectory within a probability space, wherein said trajectory is indicative of a time series of the assessed clinical outcomes.

Trajectory

As a medical condition progresses, a subject is typically monitored by medical personnel. Monitoring can be preformed by running a series of tests. As testing methods and devices, such as point-of-care microfluidic devices, become more reliable and accessible, data from the patient can be acquired and processed at multiple time points. The sequential structure of obtained data is often a time series or a set of longitudinal data, but may also be data that reflects changes that occur sequentially with no specific reference to time. The system does not require that the time or sequence values are equally spaced. In fact, the time parameter can be a random variable itself.

In some embodiments, the time series of obtaining subject data is at least 6, 24, 48, 72, or 96 hours. In other embodiments, the time series can be at least 7, 30, 60, 90, 180, or more days. The time series can also be over a series of years.

The longitudinal data provides valuable insight into the progression of a medical condition or treatment. However, as the number of tested items increases, the complexity of analyzing the longitudinal data increases. It can become very difficult to understand or determine relevant data about a medical condition or treatment.

The longitudinal data acquired from a subject can be grouped into a vector or a trajectory to assess a medical condition. A vector is defined geometrically as an arrow where the tail is the initial point and the head is the terminal point. A vector's components can relate to a geographical coordinate system, such as longitude and latitude. Navigation, by way of specific example, uses vectors extensively to locate objects and to determine the direction of movement of aircraft and watercraft.

Physics and engineering fields are probably the most common users of vector analysis and have stimulated much of the mathematical research. In the field of mechanics, vector analysis objects include equations of motion including location, velocity, direction, and acceleration; center of gravity; moments of inertia; forces such as friction, stress, and stain; electromagnetic and gravitational fields.

Velocity, the time rate of change in position, is the combination of speed (vector length) and bearing (vector direction). Acceleration is another common vector quantity, which is the time rate of change of the velocity. Both velocity and acceleration are obtained through vector analysis, which is the mathematical determination of a vector's properties and/or behaviors.

Vector analysis of longitudinal subject data pertaining to a medical condition can be used to understand the medical condition and statistically determine a discrete clinical outcome.

For example, the normal condition for the individual can be observed by plotting biomarker data for the individual. The stable, normal condition will be a located in one portion of the graph.

The individual's normal condition may be disturbed by the administration of a pharmaceutical or a change in medical condition. Under the effect of the administered pharmaceutical, the individual's normal condition will become unstable and move from its original position in the graph to a new position in the graph. When the administration of a pharmaceutical is stopped, or the effect of the pharmaceutical ends, the individual's normal condition may be disturbed again, which would lead to another move of the normal condition in the graph. When the administration of a pharmaceutical is stopped, or the effect of the pharmaceutical ends, the individual's normal condition may return to its original position in the graph before the pharmaceutical was administered or to a new or tertiary position that is different from both the primary pre-pharmaceutical position and the secondary pharmaceutical-resultant position.

In some instances, biomarker values can change very rapidly, such that standard sampling (for example, a lab test) may miss large changes in the values. In an example, sepsis can occur very quickly when a patient is using a pharmaceutical or is a member of a pharmaceutical clinical trial. Many times, early clues as to the medical condition of the patient are not seen because current testing procedures do not occur rapidly enough. Also current testing procedures are inflexible within a short period of time, so if a patient needs to be tested for a different biomarker value or physiological parameter within a short period of times (for example, 4 hours), it is often not possible to receive test results.

Large changes in biomarker values can occur such that conventional lab methods which use only one sample dilution level cannot measure the analyte due to the range of the device. Often, more sophisticated lab methods that use multiple dilution ranges that extend a range can also be overwhelmed by a massive change (for example, greater than 1000-fold) in a biomarker value. If a dilution is repeated to obtain the proper range, in many instances 24 hours may have elapsed before the results of the assays are obtained. As described, a system or method herein can report results in near real-time fashion, therefore medical personnel has the ability to change the course of medical action as necessary from the biomarker values obtained. For example, when an increase of an analyte between assay increases by 100-fold, 200-fold, 500-fold, 1000-fold, 10,000-fold, or even more, it can increase the dilution level used for the next sample (for example, 100, 200, 500, 1000, 10,000-fold or higher) in addition to changing the frequency of measurement of the analyte.

In an aspect herein, a method of monitoring sepsis development of a subject comprises: measuring at least two parameters selected from the group of (1) body temperature of said subject, (2) protein C concentration of said subject, (3) interleukin 6 (IL-6) concentration of said subject, multiple times to yield a trend of temperature, protein C trend, and/or IL-6; and wherein an increase beyond normal body temperature, a decrease in protein C concentration and/or an increase in IL-6 concentration is indicative of the development of sepsis in said subject. A decrease in protein C followed by an increase of IL-6 can be indicative of the development of sepsis in said subject. A decrease in protein C followed by an increase of IL-6 and an increase beyond normal body temperature can be indicative of the development of sepsis in said subject. In some instances, an at least about 10-fold, 100-fold, 200-fold, 500-fold, 1000-fold, 10,000-fold, 500,000-fold or more increase in IL-6 concentration in said subject is indicative of the development of sepsis in said subject. In a further instance, an at least about 10-fold, 100-fold, 200-fold, 500-fold, 1000-fold, or more decrease in protein C concentration in said subject is indicative of the development of sepsis in said subject.

In an example, when no significant event is occurring in a patient following chemotherapy at home, the measurement frequency of an analyte can be reduced. In some instances, the system can prompt appropriate action by a user based on prior results.

In some instances, the methods and systems described herein allow for the monitoring of the health status or medical condition of a subject throughout a time frame as small as a few days. For example, the evolution and pathophysiology of the disease process, the response to therapy, and the possible onset of untoward side effects upon exposure to a drug can be monitored by longitudinally sampling blood. From these samples a profile of key circulating biomarkers can be established. Specific biomarkers can be selected based on, for example without limitation: knowledge of the disease process and its molecular pathophysiology, the mechanism of action of a given compound, and its observed effects profiles.

Figure 5:
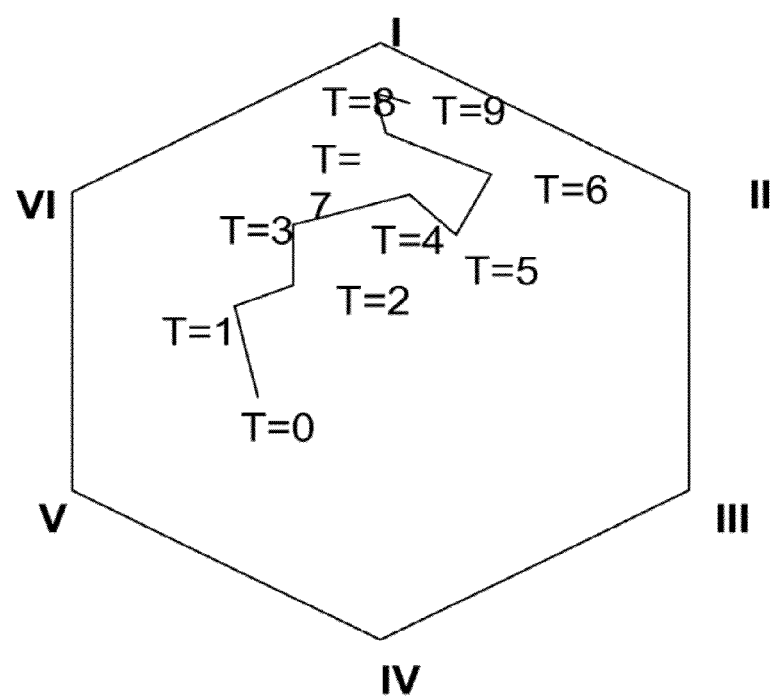
FIG. 5 illustrates a trajectory of data of a subject in a probability space.

Representation of a similar movement of longitudinal data to that previously described is illustrated in FIG. 5. At each time point (T=0 to T=9), the data point is plotted in a probability space. The line traveled from one point to the next is a vector.

Diagnosis of the individual may be aided by studying several aspects of the movement of the individual's medical condition in a probability space. The direction (for example, the angle and/or orientation) of the path followed by the medical condition as it moves in the graph can aid in the diagnosis, prognosis and treatment decision-making for a given clinical outcome. The speed and acceleration of the movement of the medical condition in the graph may also be diagnostic. Also, the position of the individual's medical condition at an independent time point may itself be diagnostic.

Given that the direction and/or speed of the movement of the normal condition in the graph is diagnostic, one can use the direction and/or speed of the initial movement of the normal condition to predict the consequent, new location of the normal condition; especially if it is established that, under the effect of a certain agent (for example, a pharmaceutical), there are only a certain number of locations in the graph at which an individual's normal condition will stabilize.

However, in some aspects of the invention, both diagnosis and prediction of assessing the medical condition of a subject are performed by qualified medical personnel and the mathematical model provides an educational tool and resource.

Figure 6:
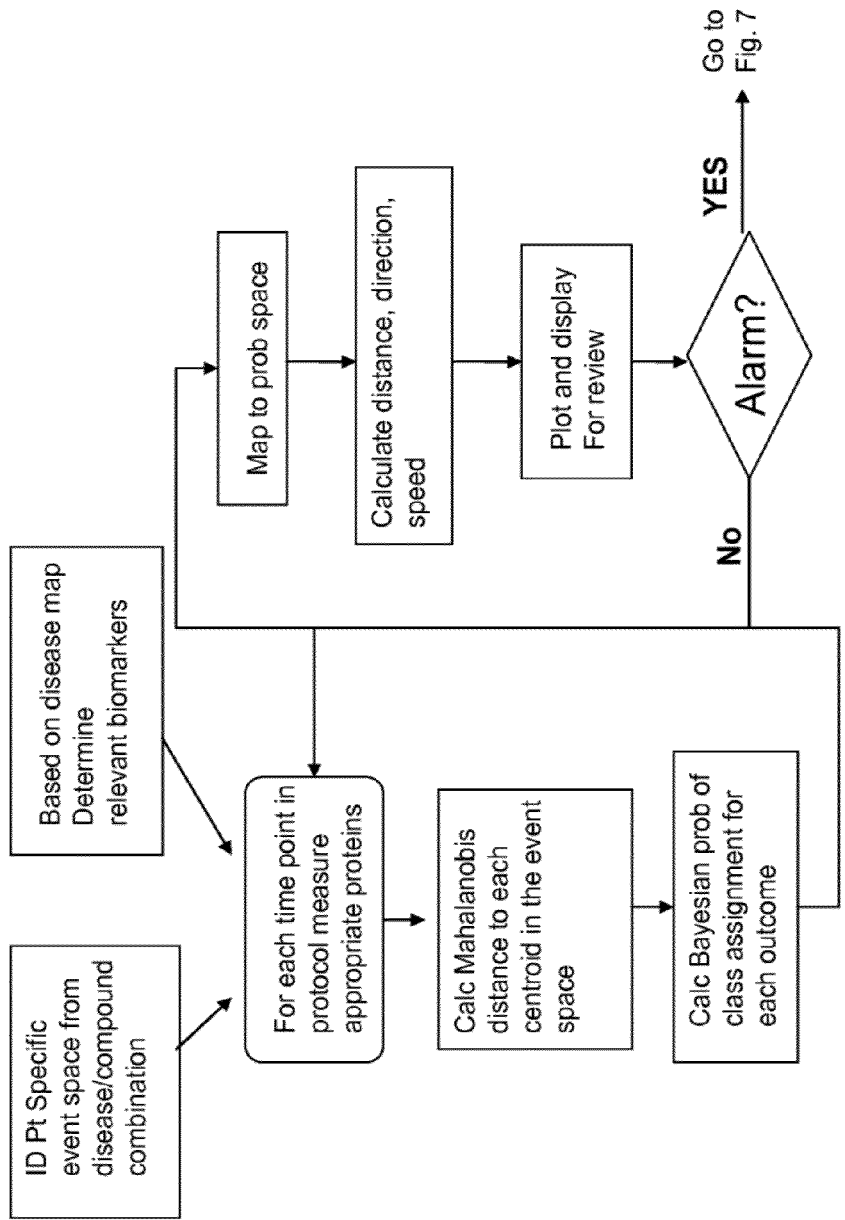
FIG. 6 is a flow chart illustrating an exemplary method of alerting a user to assess a clinical outcome of a subject.

FIG. 6 illustrates an exemplary method of the invention for applying a mathematical model longitudinally in real-time. Relevant biomarkers and discrete clinical outcomes corresponding to different biomarker patterns are predetermined from historical data. Data is then obtained from a subject and the data corresponding to each relevant biomarker is measured. Data is preferably obtained from the subject using a point-of-care microfluidic device, however, it can be obtained in any manner. Each time the data is obtained a distance metric (for example, Mahalanobis distance) is calculated in relation to each centroid obtained from a cluster analysis of the historical data. The centroids represent the discrete clinical outcomes determined from the historical data.

As following the flow diagram in FIG. 6, for each individual data set through time, the probability of the data belonging to each clinical outcome is calculated. The probability is calculated from the distance metric using a statistical estimation procedure, such as a Bayesian estimate. Based on the set of calculated probabilities, the position of each time point of subject data is assigned to the probability space. The calculation is repeated for each time point.

A trajectory or vector is then created by linking adjacent time points. The distance, direction, speed, and acceleration of the vector can be calculated and plotted for display or review. If the user (for example, physician), deems the data to be of significant importance, the user may activate an alarm or warning system and accordingly change the course of action for treating or monitoring the medical condition. After a course of action has been adjusted, the steps assessing the medical condition of a subject can be repeated to continue to monitor the trajectory of the subject.

Figure 7:
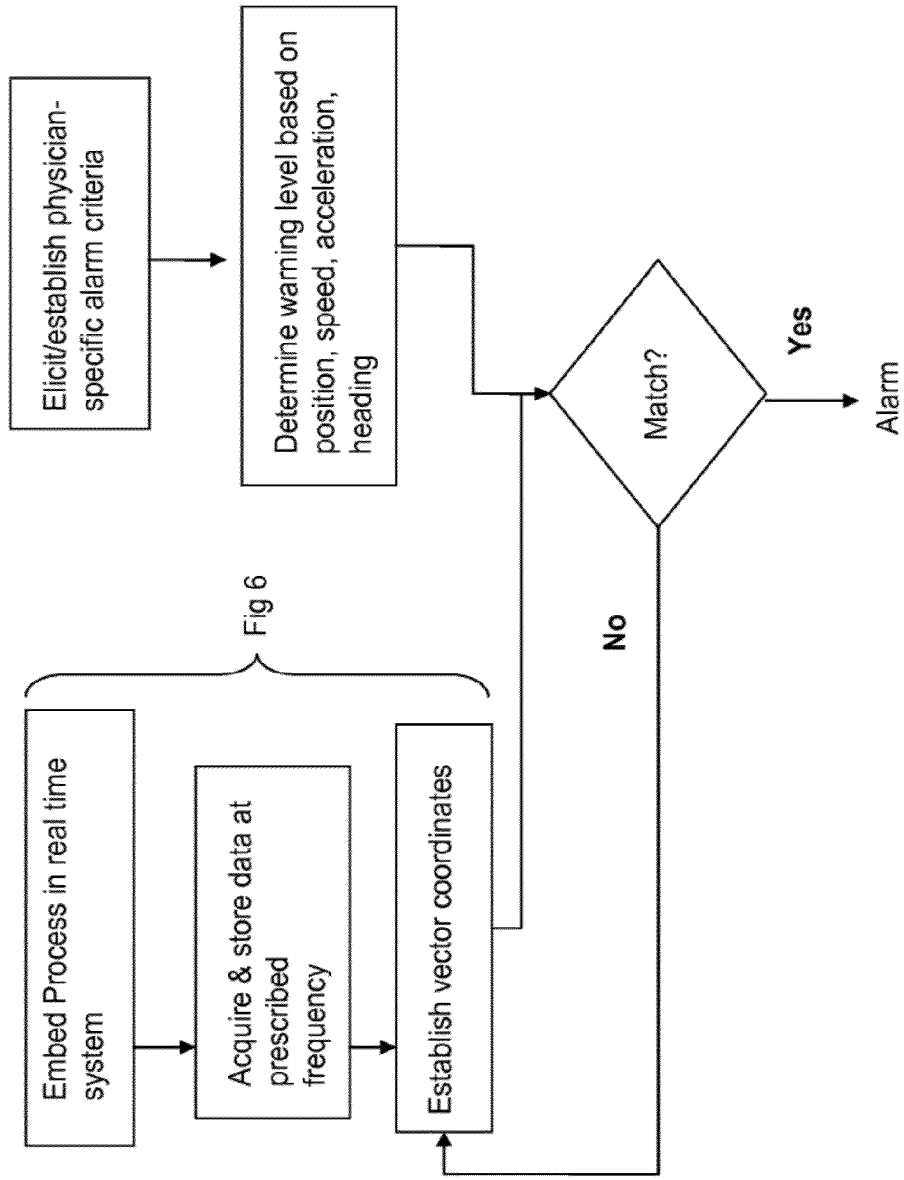
FIG. 7 demonstrates a method of establishing rules for a probability space of clinical outcomes.

FIG. 7 illustrates an exemplary method of the invention for developing an alarm or early warning system for or upon assessing the medical condition of a subject. The trajectory of a medical condition of subject and the information corresponding to the trajectory (for example, speed or acceleration) is obtained through a method of multivariate statistical calculations, such as the method illustrated in FIG. 6. In order to analyze the information obtained from the mathematical analysis, qualified medical personnel (for example, a physician) can establish criteria for activating an alarm or warning system based on the measurement of biomarker patterns from an individual subject.

This method allows each individual user to define the value and set of criteria as they see fit, according to the individual user's priorities. It is understood that each user or physician may view each medical condition differently and the example method of FIG. 7 accounts for these differences.

Figure 8:
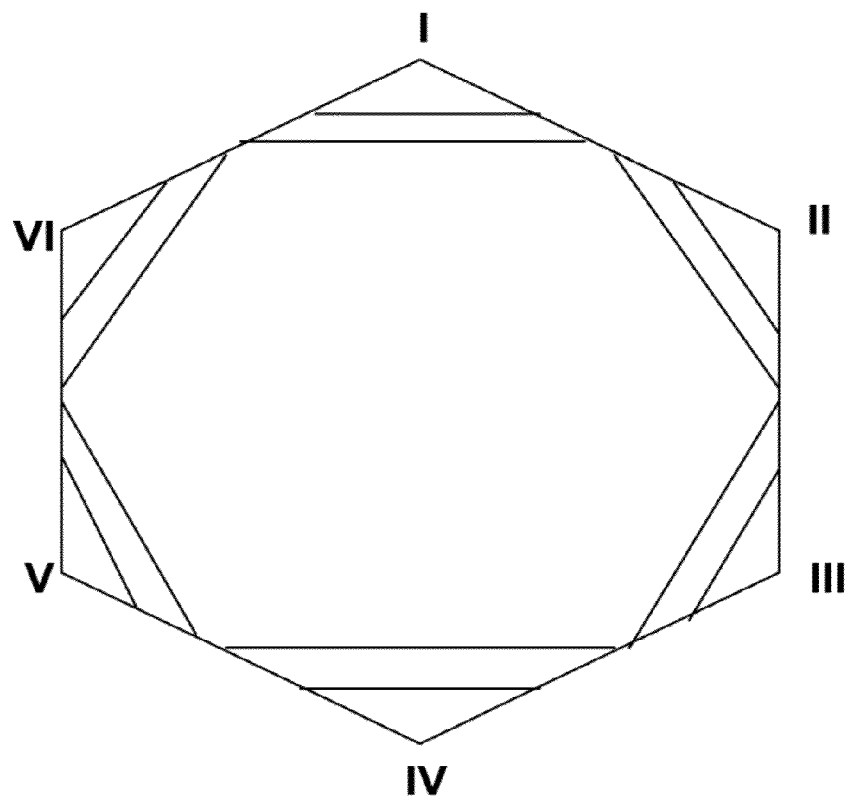
FIG. 8 illustrates a graphical presentation of rules for a probability space.

An exemplary method of the invention assigns progress lines to each discrete clinical outcome. The progress lines may represent different clinical criteria for the medical condition a subject passes over. Preferably, the progress lines are positioned and determined by an individual user, such as medical personnel. The user may assign different locations of the progress lines based upon the subject history, historical data of the medical condition, or personal experience. An example of a probability space with rules demonstrated as progress lines is illustrated in FIG. 8. For example, if the trajectory of a subject goes within one of the progress lines illustrated in FIG. 8, an alarm or warning system may be activated to notify the user or the subject. Other possible results include, but are not limited to, a system printout of the medical data, a user interface displaying the information, a flashing light, an alert system, an alarm, a buzzer, an email, a telephone communication, and a pager system. The alarm system not only assesses the current medical condition of the subject, but may also guide a course of action for the user.

When one or more of the characteristics of the trajectory surpasses a specific value as determined by the model user, an alarm or warning system can be activated. The user can then determine the next course of action for assessing the medical condition of the subject.

In an embodiment of the invention, medical personnel or the subject can be notified of a need for taking a medical action after assessing or characterizing the position of the subject data in a probability space. Examples of a notification include an alert system, an alarm, a buzzer, an email, a telephone communication, and a pager system.

Medical personnel may take medical action when notified by the methods of the invention that the medical condition of a subject has violated a rule imposed by the medical personnel. Medical action includes, but is not limited to, ordering more tests performed on the patient, altering the dosage of an administered therapeutic agent, administering a therapeutic agent, terminating the administration of a therapeutic agent, combining therapies, administering an alternative therapy, placing the subject on a dialysis or heart and lung machine, and administering a pain killer. In some embodiments, the subject may take medical action. For example, a diabetic subject may administer a dose of insulin.

After a medical action has been taken or has been chosen, an outcome analysis can be performed for characterizing a result of the selected action. The outcome analysis can lead to automatically updating the probability of the discrete clinical outcome of the subject.

Any clinical outcome, result, or action related to a particular medical condition may be utilized as a discrete clinical outcome. For example, discrete clinical outcomes may be generic, such as responder, non-responder, partial responder, and septic, or they be more specific such as adverse drug reactions. In addition, discrete clinical outcomes may be sequellae, or downstream clinically relevant events or results. Subject data can be obtained for any pharmacological, pathophysiological or pathopsychological clinical outcome. The subject data may be obtained during a first time period before an intervention is administered to the patient, and also during a second, or more, time period(s) after the intervention is administered to the patient. The intervention may comprise a drug(s) and/or a placebo. The intervention may be suspected to have a propensity to affect the heightened risk of the onset of the specific medical condition. The intervention may be suspected of having a propensity to decrease the heightened risk of the onset of the specific medical condition. The specific medical condition may be an unwanted side effect. The intervention may comprise administering a drug, and wherein the drug has a propensity to increase the risk of the specific medical condition, the specific medical condition may be an undesired side effect.

Medical conditions include, but are not limited to, pharmacological, pathological, physiological and psychological conditions. For example, abnormality, affliction, ailment, anomaly, anxiety, cause, disease, disorder, illness, indisposition, infirmity, malady, problem or sickness, and may include a positive medical condition for example, fertility, pregnancy and retarded or reversed male pattern baldness. Specific medical conditions include, but are not limited to, neurodegenerative disorders, reproductive disorders, cardiovascular disorders, autoimmune disorders, inflammatory disorders, cancers, bacterial and viral infections, diabetes, arthritis and endocrine disorders. Other diseases include, but are not limited to, lupus, rheumatoid arthritis, endometriosis, multiple sclerosis, stroke, Alzheimer's disease, Parkinson's diseases, Huntington's disease, Prion diseases, amyotrophic lateral sclerosis (ALS), ischaemias, atherosclerosis, risk of myocardial infarction, hypertension, pulmonary hypertension, congestive heart failure, thromboses, diabetes mellitus types I or II, lung cancer, breast cancer, colon cancer, prostate cancer, ovarian cancer, pancreatic cancer, brain cancer, solid tumors, melanoma, disorders of lipid metabolism, HIV/AIDS, hepatitis, including hepatitis A, B and C, thyroid disease, aberrant aging, and any other disease or disorder.

Biological Markers

Biological markers, also referred to herein as biomarkers, according to the present invention include without limitation drugs, prodrugs, pharmaceutical agents, drug metabolites, biomarkers such as expressed proteins and cell markers, antibodies, serum proteins, cholesterol, polysaccharides, nucleic acids, biological analytes, biomarker, gene, protein, or hormone, or any combination thereof. At a molecular level, the biomarkers can be polypeptide, glycoprotein, polysaccharide, lipid, nucleic acid, and a combination thereof.

Of particular interest are biomarkers associated with a particular disease or with a specific disease stage. Such biomarkers include but are not limited to those associated with autoimmune diseases, obesity, hypertension, diabetes, neuronal and/or muscular degenerative diseases, cardiac diseases, endocrine disorders, any combinations thereof.

Also of interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are analytes that are indicative of a microorganism. Exemplary microorganisms include but are not limited to bacterium, virus, fungus and protozoa. Other biomarkers obtained from a subject also include blood-born pathogens selected from a non-limiting group that consists of *Staphylococcus epidermidis*, *Escherichia coli*, methicillin-resistant *Staphylococcus aureus* (MSRA), *Staphylococcus aureus*, *Staphylococcus hominis*, *Enterococcus faecalis*, *Pseudomonas aeruginosa*, *Staphylococcus capitis*, *Staphylococcus warneri*, *Klebsiella pneumoniae*, *Haemophilus influnzae*, *Staphylococcus simulans*, *Streptococcus pneumoniae* and *Candida albicans*.

Biomarkers also encompass a variety of sexually transmitted diseases selected from the following: gonorrhea (*Neisseria gorrhoeae*), syphilis (*Treponema pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Biomarkers encompass a diversity of respiratory pathogens including but not limited to *Pseudomonas aeruginosa*, methicillin-resistant *Staphlococccus aureus* (MSRA), *Klebsiella pneumoniae*, *Haemophilis influenzae*, *Staphlococcus aureus*, *Stenotrophomonas maltophilia*, *Haemophilis parainfluenzae*, *Escherichia coli*, *Enterococcus faecalis*, *Serratia marcescens*, *Haemophilis parahaemolyticus*, *Enterococcus cloacae*, *Candida albicans*, *Moraxiella catarrhalis*, *Streptococcus pneumoniae*, *Citrobacter freundii*, *Enterococcus faecium*, *Klebsella oxytoca*, *Pseudomonas fluorscens*, *Neiseria meningitidis*, *Streptococcus pyogenes*, *Pneumocystis carinii*, *Klebsella pneumoniae Legionella pneumophila*, *Mycoplasma pneumoniae*, and *Mycobacterium tuberculosis*.

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR.

Exemplary liver markers include, without limitation, Arginase 1 (liver type), Alpha-fetoprotein (AFP), Alkaline phosphatase, Alanine aminotransferase (ALT), Lactate dehydrogenase (LDH), Protein C, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancreatic markers include without limitation Insulin, Amylase, Pancreatitis-Associated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx)

Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type 1N propeptide, Osteocalcin (bone gla-protein), Alkaline phosphatase, Cathepsin K, COMP (Cartilage Oligimeric Matrix Protein), Osteocrin Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease markers include without limitation Viremia, Bacteremia, Sepsis, PMN Elastase, PMN elastase/α1-PI complex, Surfactant Protein D (SP-D), HBVc antigen, HBVs antigen, Anti-HBVc, Anti-HIV, T-supressor cell antigen, T-cell antigen ratio, T-helper cell antigen, Anti-HCV, Pyrogens, p24 antigen, Muramyl-dipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Insulin, Glucose, Hemoglobin, ANGPTL3 and 4.

Exemplary inflammation markers include without limitation Rheumatoid factor (RF), Tumor Necrosis factor-α (TNF-α), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4) Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor).

Exemplary markers of lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII: Antihemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibodies include those for EGFR, ErbB2, and IGF1R.

Exemplary tyrosine kinase inhibitors include without limitation Abl, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threoline Kinase Inhibitors include without limitation AKT, Aurora A/B/B, CDK, CDK (pan), CDK1-2, VEGFR2, PDGFRb, CDK4/6, MEK1-2, mTOR, and PKC-beta.

GPCR targets include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

In a separate embodiment, a method herein utilizes pharmacological parameters useful for assessing efficacy and/or toxicity of a therapeutic agent and the agent's affect on a medical condition. For the purposes of this invention, a "therapeutic agent" is intended to include any substances that have therapeutic utility and/or potential. Such substances include but are not limited to biological or chemical compounds such as simple or complex organic or inorganic molecules, peptides, proteins (for example, antibodies) or a polynucleotides (for example, anti-sense). A vast array of compounds can be synthesized, for example, polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Implementation of the Methods

It is to be understood that the exemplary methods and systems described herein may be implemented in various forms of hardware, software, firmware, special purpose processors, or a combination thereof. Methods herein can be implemented in software as an application program tangibly embodied on one or more program storage devices. The application program may be executed by any machine, device, or platform comprising suitable architecture. It is to be further understood that, because some of the systems and methods depicted in the Figures are preferably implemented in software, the actual connections between the system components (or the process steps) may differ depending upon the manner in which the present invention is programmed. Given the teachings herein, one of ordinary skill in the related art will be able to contemplate or practice these and similar implementations or configurations of the present invention.

Figure 9:
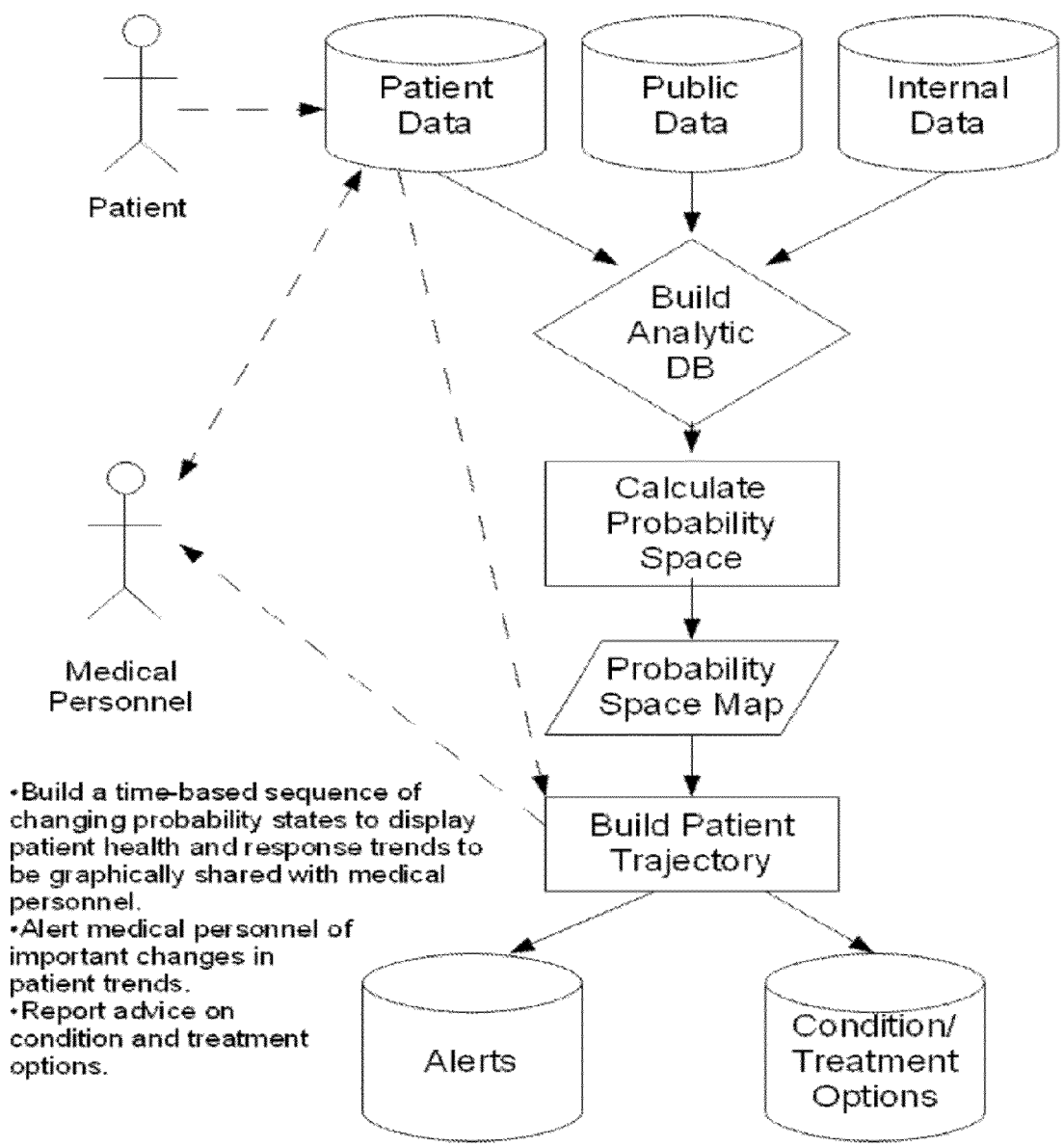
FIG. 9 is a flow chart illustrating an exemplary method of implementing a mathematical model to assess a clinical outcome.

FIG. 9 illustrates the process flow of building the model and system for assessing the medical condition of a subject. The subject inputs personal data into a database. The same or a different database contains data from other subjects with a similar medical condition. Data from the other subjects can be historical data from public or private institutions. Data from other subjects may also be internal data from a clinical study.

The subject may input data in a variety of ways, or using a variety of devices. For example, a point-of-care microfluidic device may be used to acquire biomarker data at the point-of-care. The data from the device may then be communicated directly from the device to a database or processor. A computer or data entry system may also input subject data to a database or processor. Data may be automatically obtained and input into a computer from another computer or data entry system. Another method of inputting data to a database is using an input device such as a keyboard, touch screen, trackball, or a mouse for directly entering data into a database.

A database is developed for a medical condition in which relevant clinical information is filtered or mined over a communication network (for example, the Internet) from one or more data sources, such as a public remote database, an internal remote database, and a local database. A public database can include online sources of free clinical data for use by the general public, such as, for example, databases supplied by the U.S. Department of Health and Human Services. For example, an internal database can be a private internal database belonging to particular hospital, or a SMS (Shared Medical System) for providing clinical data. A local database can comprise, for example, biomarker data relating to discrete clinical outcome. The local database may include data from a clinical trial. It may also include clinical data such as temperature and laboratory information, EKG results, blood test results, patient survey responses, or other items from patients in a hospital or an internal hospital monitoring system. The database can also include historical reference data of a plurality of subject members in relationship to at least one biological marker.

The database may also be implemented on a variety of commercially available authoring packages.

The database may be of a storage unit of a medical information system.

Data from a database can be filtered and classified according to specific cases or medical conditions or a group of diagnoses and conditions. For example, the classification within the database may follow the standard international code of diagnoses (ICD-9 coding system). A medical condition may include, for example, a physical state of a subject or a disease that the subject is suffering from.

In an embodiment, the data stored in the database may be selected from the categories consisting of: pathology, anatomy, treatment option, treatment outcome, pharmacological parameter, pharmacokinetics parameter, psychological parameter, and genomic information.

Subject data can be stored with a unique identifier for recognition by a processor or a user. In another step, the processor or user can conduct a search of stored data by selecting at least one criterion for particular patient data. The particular patient data can then be retrieved.

Relationships can be established between elements of the public databases, the internal databases and the subject data. Explicit relationships declare and record inferences made based on information revealed by the trajectory or other available observations.

FIG. 9 illustrates the flow of data from a database that includes the data from the subject to a processor that performs the mathematical methods described herein to construct a probability space. The subject data may also be inputted to the processor separately from the data pertaining to a discrete clinical outcome that is stored in a database.

A processor can perform calculating the probability space. Once a probability space map is prepared, the same processor or a different processor can plot biomarker data from an individual subject within the probability space. The probability space map itself can be transmitted to an output, such as a display monitor. The position of the subject data within the probability space may also be transmitted to an output. The processor may have a means for receiving patient data directly from an input device, a means of storing the subject data in a storage unit, and a means for processing data. The processor may also include a means for receiving instructions a user or a user interface. The processor may have memory, such as random access memory, as is well known in the art. In one embodiment, an output that is in communication with the processor is provided.

A user interface refers to graphical, textual, or auditory information presented to a user. User interface may also refer to the control sequences used for controlling a program or device, such as keystrokes, movements, or selections.

A user interface may be a commercial software application for displaying subject data and/or the position of the subject data in a probability space. The user interface generally provides users with access to a task-specific set of functions to view and modify content. In preferable embodiments of the invention, the user interface is a graphical user interface (GUI). In some embodiments, a constructed probability space in two dimensions can be viewed using a GUI. Also, the trajectory of subject data positioned within the probability space can be viewed using a GUI. The GUI may be displayed on a display monitor. Other user interfaces that may be utilized with the methods of the invention include, but are not limited to, alert systems, web-based interfaces, text interfaces, sound interfaces, batch interfaces, and intelligent interfaces. In an embodiment of the invention, the user interface can remotely communicate with the system.

By acquiring data from a subject at multiple points in time, a trajectory of the subject data can be processed. For each time point, a processor may calculate the position of the subject data time point in a probability space. A trajectory is created by connecting at least two time points of subject data. Different vector parameters of the trajectory can be calculated such as distance, speed, direction, and acceleration. The vector parameters can be calculated by a processor. The processor may be the same as or different than the processor used to construct the probability space.

Based upon rules imposed by a user, the position or trajectory of subject data may activate an alert. The alert or alert system notifies the user when the subject data conflicts with a rule imposed by a user. For example, a rule may comprise the probability of a subject of developing an adverse drug reaction (ADR) is greater than 60 percent. When the probability of the subject data exceeds the rule, an alert is communicated to a user.

Examples of an alert include, but are not limited to, a sound, a light, a printout, a readout, a display, a page, an e-mail, a fax alert, telephonic communication, or a combination thereof. The alert may communicate to the user the raw subject data, the calculated position in probability space of the subject data, the trajectory of the subject data, or a combination thereof.

A user is most preferably medical personnel. In an embodiment, the same user has access to the subject data, establishes the rules for alerting the user, and is alerted by the alert. The user may also be the subject. For example, a diabetic patient may monitor his personal glucose levels or other biomarker levels. In another embodiment, a user has access to the subject data at any step of the mathematical model.

Figure 10:
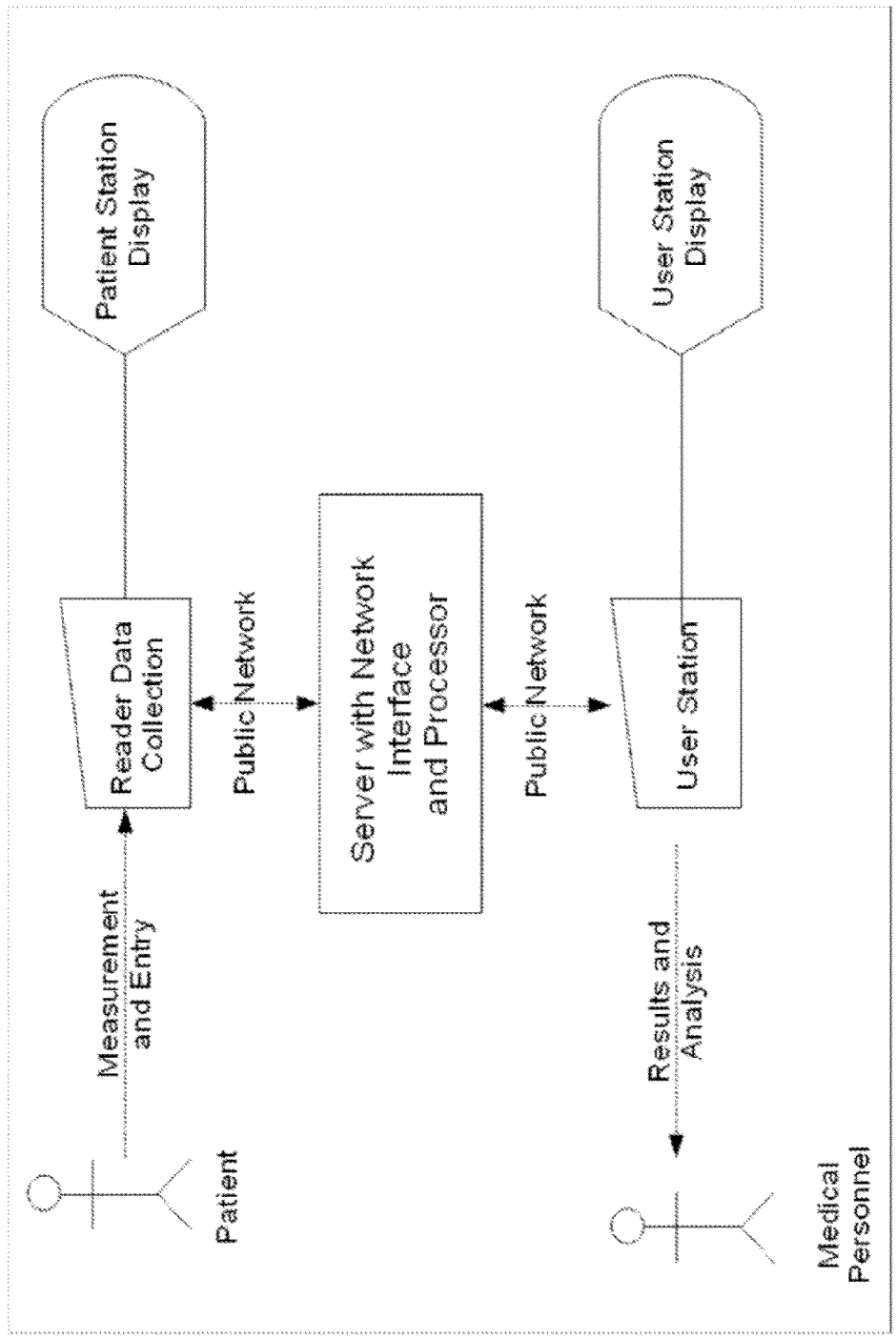
FIG. 10 is a flow chart illustrating an exemplary system comprising a server for communicating and processing medical data.

FIG. 10 demonstrates a networking method of assessing the medical condition of a subject. A system of communicating information may or may not include a reader for reading subject data. For example, if biomarker data is acquired by a microfluidic point-of-care device, the values assigned to different individual biomarkers may be read by the device itself or a separate device. Another example of a reader would be a system to scan in subject data that has been entered in an electronic medical record or a physician chart. A further example of a reader would consist of an electronic patient record database from which subject data could be directly obtained via the communications network.

A user station may be incorporated into the methods and systems herein. The user station can act as a reader for reading subject data or as a data entry system. The user station may also be used to communicate data information directly to a user, such as medical personnel or the subject. The user station platform may be a computer or one of a wide variety of hardware platforms that runs any operating system. The platform may read and write to and from a storage unit. A storage unit may be incorporated within the user station. As will be readily apparent to those of ordinary skill in the art, other hardware may be used to execute the methods of the invention.

According to still further embodiments, a server may be provided for use in assessing a medical condition of a subject. In some embodiments, a reader and/or user station communicates with a server. The server may comprise a network interface and a processor. A storage unit may also be provided in the server. The storage unit is coupled to receive the patient data from the input device, reader, or user interface, and to store the patient data.

The storage unit may be any device capable of storing data for a long period of time, either as a component of the platform, or as a separate entity that is coupled to the network. Although any appropriate storage capacity may be used, the capacity is typically at least ten megabytes and more usually at least twenty gigabytes. The storage unit may be permanent or removable. For example, the storage unit may be as magnetic random access, such as flexible or hard disk drive, magnetic sequential access, such as tape, optical random access such as CD, DVD or Magnetic Optical drive, and solid state memory, such as EPROM, MRAM and Flash. In addition, the present invention anticipates other storage devices. All of the aforementioned storage units are by way of example and are not intended to limit the choices that are or may become available in the art.

In some embodiments, the data are further manipulated prior to storage by the processor compressing the data. Some data are very large and compression permits conservation of storage space. In the absence of compression, this large amount of data may present a particular problem for the storage of medical information.

In other embodiments of a system for assessing the medical condition of a subject, data storage, processing and control of data are implemented on a server that is in communication with a user station. Optionally, computations with the data may be performed on the server as well. In this client-server embodiment, the server is communicatively coupled to one or more user stations by local area network (LAN), implemented with Ethernet, Wi-Fi, Bluetooth, USB or Firewire, a Wide Area Network (WAN) such as the Internet, implemented by broadband cable, xDSL, T1, metropolitan Wi-Fi or other high speed communications down to plain-old-telephone-service (POTS).

A user station is in communication with a server to output the information processed by the server. The user station may be the same or different from the user station or device used to input subject data into the system. The user station may also be an alert or a warning system. Examples of a user station include, but are not limited to, a computer, a PDA, a wireless telephone, and a personal device, such as an iPod. The user station may be in communication with a printer or a display monitor to output the information processed by the server.

In a networked system comprising a server, any number devices may be members of a medical network enterprise and access a central collection of medical data stored in a server. A given user station may have access to enormous amounts of patient data from healthcare sources anywhere in the world. In one application, data from multiple practitioners are accumulated for defined clinical trial studies.

Statistical information is provided to the user of the system, preferably at the point-of-care. The point-of-care is where treatment is implemented. Advantageously, the dynamic and real-time characteristics of Internet usage are captured in this feature. This enables medical personnel or the subject either in the office or in the field to instantaneously be notified of and presented with, for example, a subject's medical condition and statistical information pertaining to the subject data.

The user station, alert system, or output device may encrypt the data prior to data transmission. The data can also be encrypted by the processor to protect private information. A variety of encryption schemes may be used, such as public key encryption or private key encryption. The encryption components may be stand-alone components or software components. The server may also include a decryption unit for decrypting received subject data prior to storage.

In an alternative embodiment, if the communication bandwidth between the user and the server becomes restrictive (for example, if the server is "down"), the model can be duplicated and reside in a mirror server at a user station. Updates and communications between the server and the mirror server can be done off-line at predetermined times. On-line requests from the user can be handled locally by the mirror server. This alternative provides increased reliability for users, since the on-line processes do not depend on outside networks.

In an alternative configuration of the data analysis system, client-based architecture is used where storage, data processing and computations are performed on a user station. An input device transmits data from a source to a platform. The platform is coupled to a display through a display controller. The display may be any one of a number of conventional display devices, such as a liquid crystal display or video display. The platform contains a storage unit, a processor and an interface for communicating with the input device. The storage unit has a database for storing, manipulating and retrieving subject data. The storage unit also may store and run an operating system. The user station platform may be a computer or one of a wide variety of hardware platforms that runs any operating system. The platform may read and write to and from its storage unit. As will be readily apparent to those of ordinary skill in the art, other hardware may be used to execute the software.

In another aspect, computer readable instructions are provided, which when executed cause a processor to: provide a probability space defined by a set of discrete clinical outcomes, each of which is characterized by a statistical distribution of at least one biological marker; obtain subject data corresponding to the at least one biological marker; and calculate the position of said subject data in said probability space to assess the probability of a medical condition of said subject.

The computer readable instructions may be a part of a software package. The software package can be provided with a server of the invention or an input device, such as a microfluidic point-of-care device.

In an embodiment, computer readable instructions comprise instructions for creating a trajectory between two time points of subject data. The instructions may also cause a processor to calculate vector parameter of a trajectory, such as speed, position, heading, and acceleration.

Computer readable instructions may direct a processor or output device to output the assessment of a medical condition. The instructions, when executed, may display a graphical representation on a monitor, print an output on a printer, or activate an alert or alarm.

In another aspect, computer readable instructions may be stored in a computer readable medium. In some embodiments, the computer readable medium that stores instructions is a storage unit as described herein. Still other embodiments may provide a computer readable medium having stored therein a plurality of sequences of instructions, which, when executed by a processor, execute a method of the invention.

The computer readable instructions when executed can cause a processor to provide a user defined alert condition based on an assessment of trajectory parameters of the subject data in the probability space. In an embodiment, the trajectory parameters are at least one of speed, acceleration, direction, and position.

As used herein, a "computer readable medium" refers to any medium which can be read and accessed directly by a computer or a processor. Featured computer readable media include, but are not limited to, magnetic storage medium, optical storage medium, electrical storage medium, and hybrid storage medium of any of these categories.

The computer readable instructions can operate in a software runtime environment of the processor. In an embodiment, a software runtime environment provides commonly used functions and facilities required by the software package. Examples of a software runtime environment include, but are not limited to, computer operating systems, virtual machines or distributed operating systems. As will be appreciated by those of ordinary skill in the art, several other examples of runtime environment exist.

The computer readable medium may be a storage unit of the present invention as described herein. It is appreciated by those skilled in the art that computer readable medium can also be any available media that can be accessed by a server, a processor, or a computer.

Computer readable media includes volatile and non-volatile, removable and non-removable media implemented in any method or technology for storage of information such as computer-readable instructions, data structures, program modules, or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer. A skilled artisan can readily adopt any of the presently known methods for recording information on a computer readable medium.

The computer readable medium can be incorporated as part of the computer-based system of the present invention, and can be employed for a computer-based assessment of a medical condition.

Healthcare Operating System

Different aspects of the invention can be used and developed for healthcare systems. Examples of such systems include point-of-care systems, a healthcare operating system or a combination of both. For example, a user may test a blood sample with a device and the information from the test can be provided to a system or method of the invention, which in turn sends additional information to the user.

In an embodiment, a healthcare system is part of an integrated infrastructure built around real-time, point-of-care disposable blood monitoring devices which analyze about 10 microliter samples in a similar manner to automated replication of the manual processes run by a central laboratory. In an integrated infrastructure, information can be wirelessly transmit from an assay device to a database which integrates data from the device with stored data from disparate databases (patient record, genetic or genomic information, data from clinical trials) into a central database. The system can then allow for the automatic application of mathematics to the database in the context of the pathophysiology of a given disorder. For example, a healthcare system can be used to rapidly improve the label of key drugs through adaptive clinical studies which can generate publications for label expansions for new indications, patient subpopulations, and for ameliorating safety concerns.

In an embodiment of the invention, a healthcare system can be utilized for home, real-time blood monitoring has significant implications which allow us to collect information which cannot be seen using the conventional blood testing infrastructure.

Figure 11:
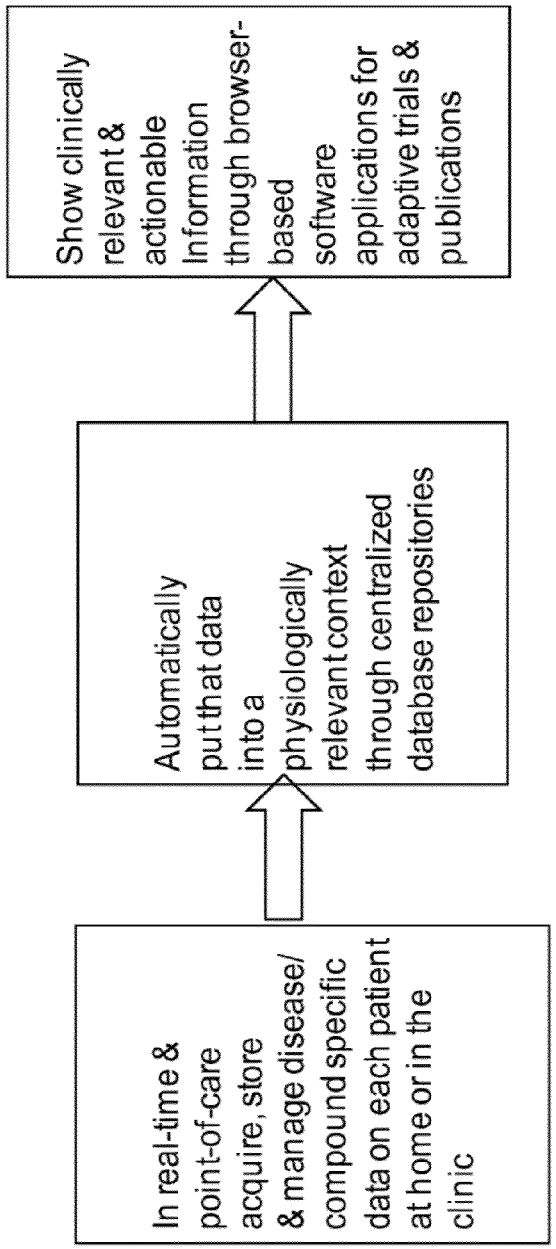
FIG. 11 illustrates an exemplary embodiment of a system of the invention with real-time acquisition of subject data and the transmittal of the information in real-time to a server or system that is capable of converting the information or data to a physiologically relevant context.
Figure 11:
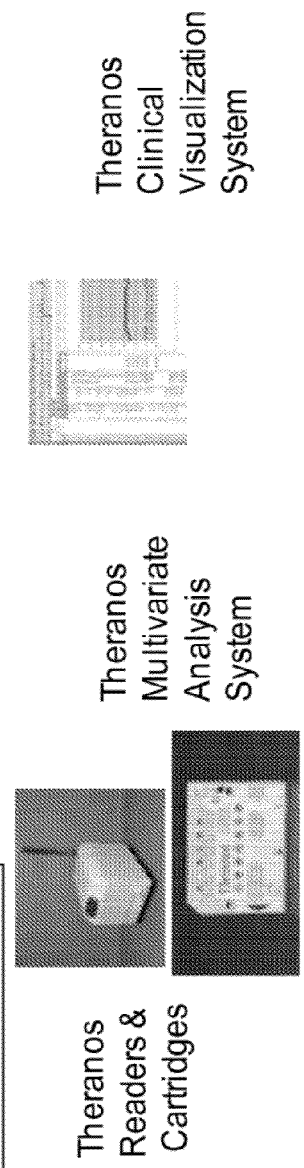

FIG. 11 illustrates an exemplary embodiment of a system of the invention. Real-time acquisition of subject data can be accomplished using a point-of-care device. The point-of-care device can acquire, store, and/or manage information based upon a specific disease or compound. The point-of-care device may also be in communication with the user or a computer or system belonging to the user. A point-of-care environment in this example can be the home or the clinic. Also illustrated in FIG. 11 is transmitting information in real-time from the point-of-care device to a server or system that is capable of converting the information or data to a physiologically relevant context. This can be accomplished by transferring the information to a database or a plurality of databases. The databases can be on a server or a plurality of servers. In an embodiment, a centralized database repository is used to analyze the data and return the data to an end user in a physiologically relevant context. The data can be returned and, in the example of FIG. 11, information, such as clinically relevant and actionable information, can be returned to a user through browser-based software applications. The information could be used for adaptive clinical trials and publications if the end user is a medical researcher or pharmaceutical company.

A system of the invention comprising a point-of-care device in communication with a healthcare system may not require the transfer of samples, such as transportation to a laboratory, which in turn, can improve the integrity of a sample. Detection of an analyte in a system or method of the invention can be provided in real-time at the point-of-care. Real-time detection integrated with a healthcare central database system can allow for the creation of complex longitudinal data series acquired by an immunoassay device.

Figure 12:
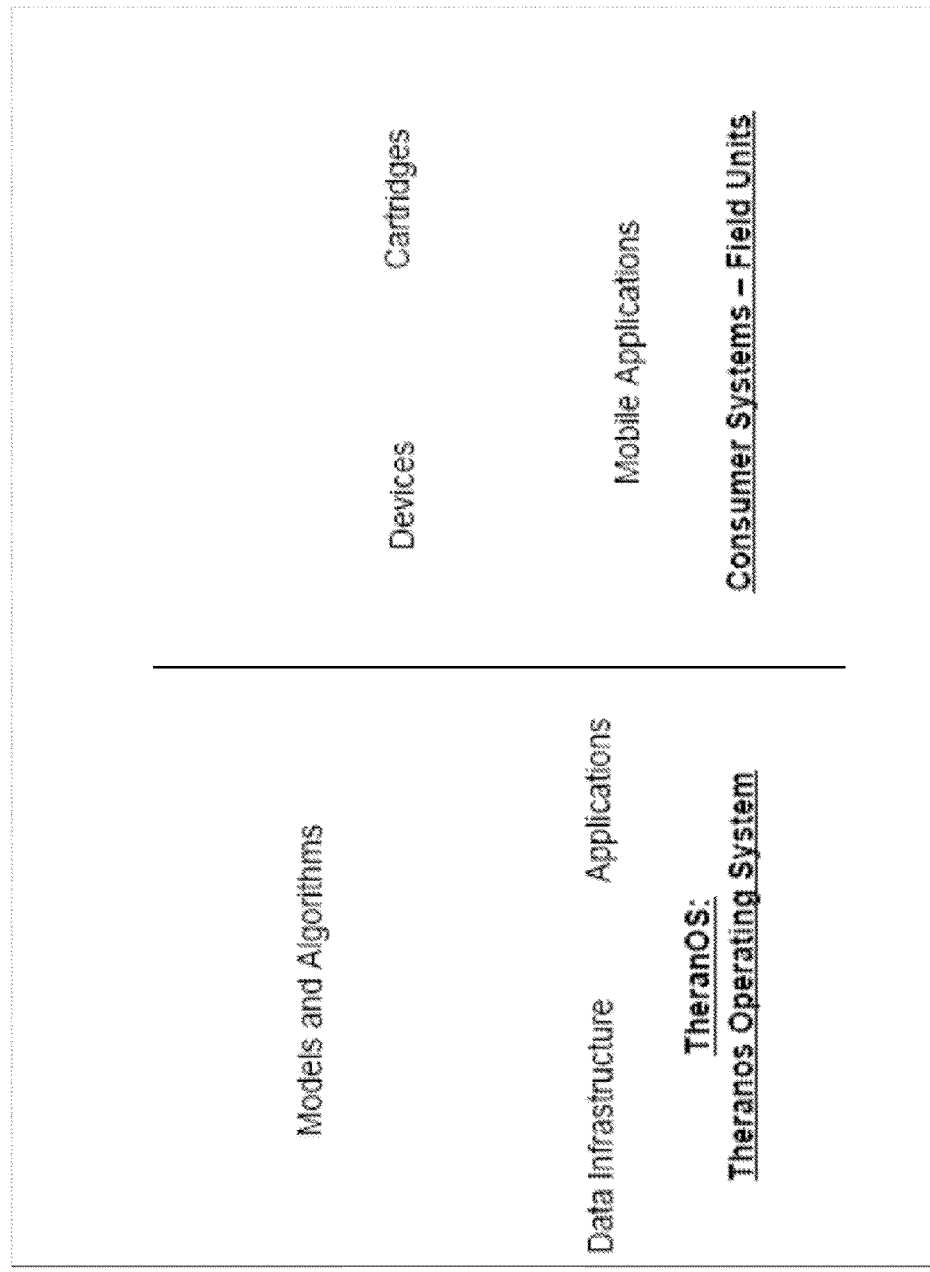
FIG. 12 demonstrates an exemplary system of the invention, wherein a health care operating system comprises data infrastructure, models and algorithms, and software applications.

FIG. 12 demonstrates an exemplary system of the invention, wherein a health care operating system comprises data infrastructure, models and algorithms, and software applications. The data infrastructure can be used by a pharmaceutical company for clinical trials across an entire pharmaceutical pipeline. A model or algorithm of the health care operating system can comprise, for example, predictive and dynamic, multivariate, multi-dimensional models that can be customized for program-specific objectives and that can map disease progression and regression. A system can be integrated with back-end algorithms, models, and data in the data infrastructure. For example, a system can transmit individualized content to users on device touch-screens or mobile phones. The feedback may assist with behavior modification and increase compliance with therapy. The algorithms described herein enable correlation of blood data to efficacy dynamics profiles, behavior, lifestyle, diet, and side-effects.

Content can be based on data for patient classes, which recognize physiological and psychological pre-dispositions as well as local socio-environmental influences. In another embodiment, a system can link users through social networks, where success stories compound through the combination of each tailored home health system with a given therapy.

The health care operating system can interact at the point-of-care with consumer systems, such as an assay cartridge, an assay reading device, or a mobile device such as a cell phone. The field units can be integrated with point-of-care home and mobile monitoring systems. Field units can be remote, portable patient care systems and can provide on-site, real-time, automatic processing of cartridges for blood analysis. In some instances, field units comprise a user interface, allowing patient to initiate assays and graphically enter a variety of relevant information, such as: patient diaries, environmental, behavioral, and psychological information, and two-way communication system from the instruments to medical personnel or mobile phones and back to patients with relevant content, messages, and health information. In some instances, blood and environmental data is automatically (for example, wirelessly) transmitted into models in real time.

As described herein, a health care operating system can comprise information integration and exploitation infrastructure that permits, for example without limitation: data acquisition and storage of point-of-care results in real time, integration of blood parameters and patient diary data with all other physiologically relevant information, and a central mathematical software program. The central mathematical software program can graphically visualize, help to interpret, and analyze all data in one place and link any new information into a disease management system that then maps the information onto a probability space of clinical outcomes. A health care operating system or a field unit can provide a graphical display of clinically relevant and actionable information back to the health care provider and/or the patient or user.

Possible applications for a healthcare system of the invention include, but are not limited to, an integrated link to an adaptive clinical trial or healthcare management system, drug and systems combinations for post-prescription monitoring, a healthcare operating system (for example, a server controlled point of care whole blood monitoring systems), and identification of correlations to efficacy of key compounds during clinical studies.

In an embodiment, a system can provide a graphical portrayal of integration of available data sets to a user.

In another embodiment, a system of the invention can generate data that may serve as historical data in future studies. A system can be customized according a the needs of a user, for example, extracting relevant information from a pharmaceutical company's existing databases, a central mathematical software program which allows a pharmaceutical company to visually see, interpret, and analyze all of their data in a place and is linked to a clinical trial system.

When utilized with clinical trials of pharmaceuticals, a system of the invention can provide an understanding of compound efficacy, disease progression and patient response that may not be possible using the conventional blood testing infrastructure.

A database and a healthcare system can be customized to monitor trends protein assays over time and their relationship to disease progression across different indications while accounting for the other relevant variables or biomarkers in the pathophysiology of the disease. The customization can be designed to automatically incorporate all relevant data for use in mapping disease progression across relevant indications and are the foundation of historical data. The maps and baselines can be used in designing future studies and in future studies to extract better information from blood test results and provide early reads on efficacy across different indications.

Figure 13:
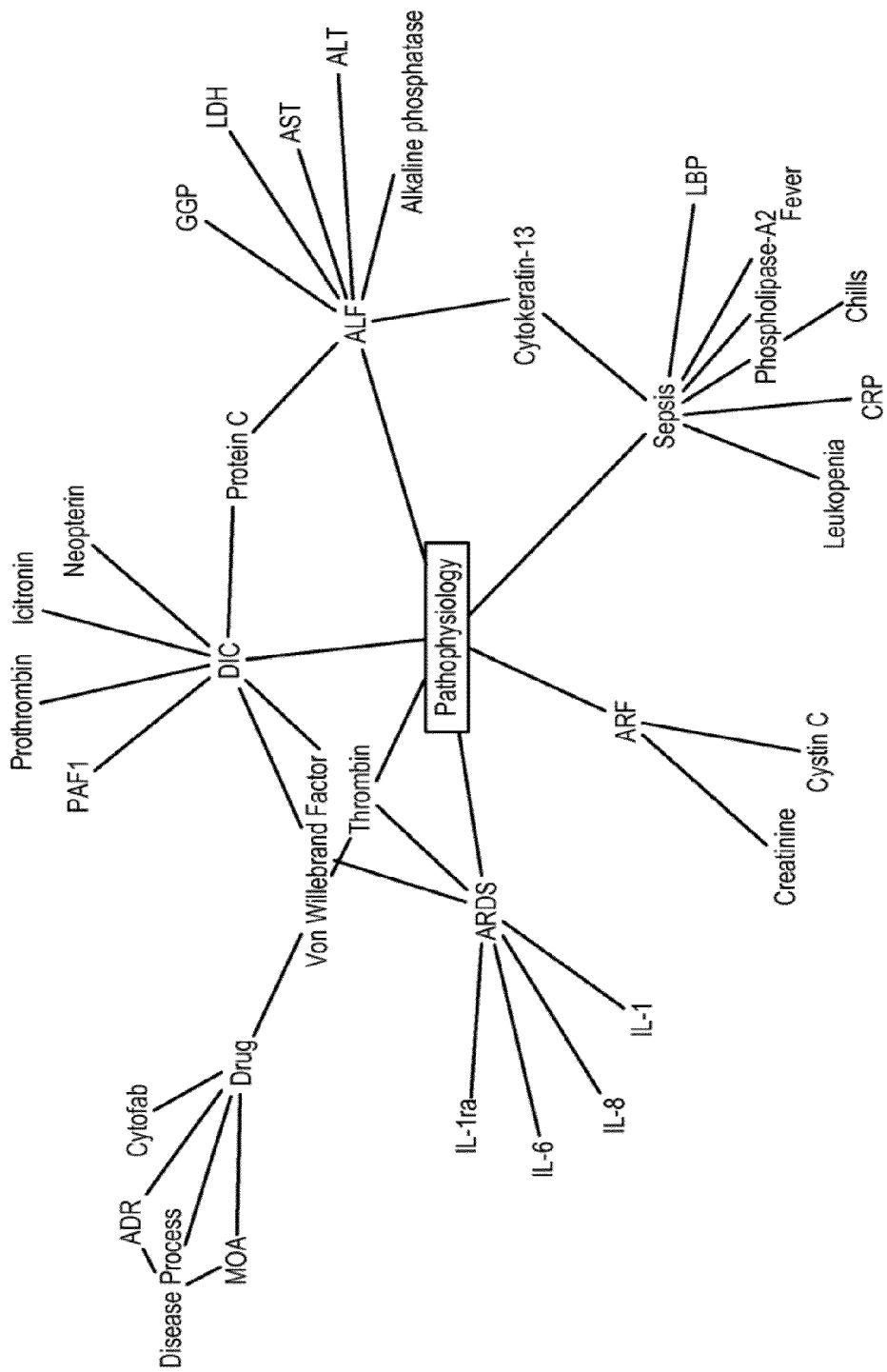
FIG. 13 demonstrates an exemplary database comprising an ontology of biomarkers that are related some types of medical conditions.

FIG. 13 demonstrates an exemplary database comprising an ontology of biomarkers that are related some types of medical conditions. For example, sepsis as a disease is categorized as a pathophysiology and is linked in this ontology to Acute Liver Failure (ALF), Disseminated Intravascular Coagulation (DIC) and the like. Each of these pathologies can be considered a sequellae of sepsis in the context of this ontology. In this example, a drug used to treat sepsis is Cyto-Fab. In some instances, the sequellae can be characterized by the spectra of biomarkers as described in FIG. 13. For example, ALF is characterized by specific patterns of ALT, AST, GGT, and Alkaline phosphatase.

In an aspect of the invention, the methods, devices and systems disclosed herein can comprise a healthcare operating system. A healthcare operating system can comprise a central control system for delivery of care to consumer and for an economic model for payors and payees.

In an embodiment, a healthcare operating system can provide an early system possibly to detect the onset of disease. A system can further comprise a learning engine that ties to the preferences of a user or an insurance provider based on drug availability, targeted response rate, or payment structure.

A computer system or server of the invention can include a dynamic learning engine, for example, as the system or server receives data, the operations of the system or server can be updated. A system or server can also call in to siloed databases, extracts, and locally store (permanently or temporarily) information in a central data repository.

In another embodiment, a healthcare system can comprise a communications portal for a user to communicate an array of information to the system, such as weight, nicotine consumption, food consumption, exercise, and physchiatric variables.

Figure 14:
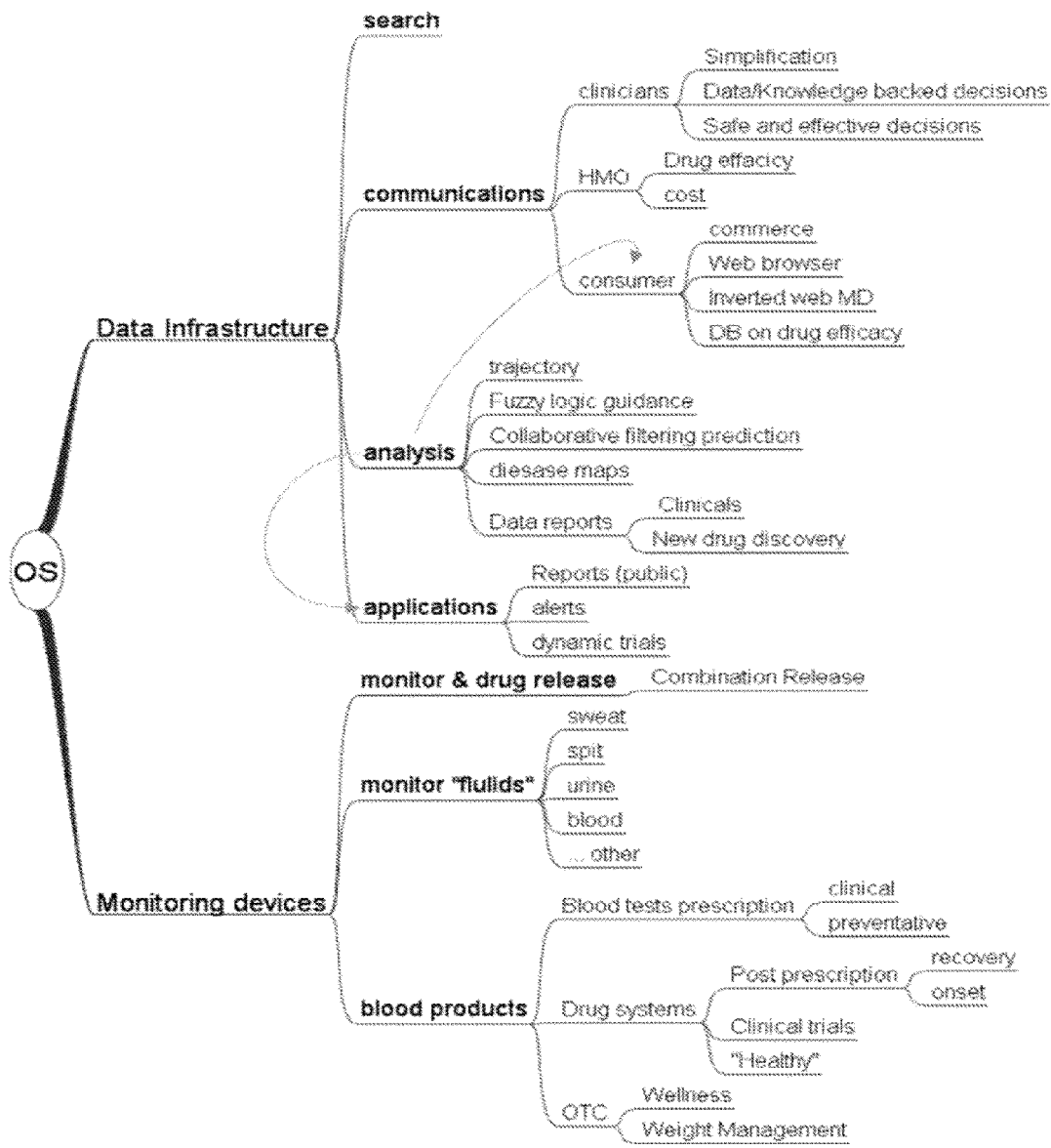
FIG. 14 illustrates the an exemplary hierarchy of a healthcare operating system of the invention wherein the central operating system has access to a data infrastructure and monitoring devices for obtaining subject data.

FIG. 14 illustrates an example hierarchy of a healthcare operating system of the invention. The central operating system has access to a data infrastructure and monitoring devices for obtaining subject data. As demonstrated in the example in FIG. 14, the data infrastructure can comprise a search tool, communication links, analysis of data, and applications. For example, a communications link can communicate to a consumer, clinician, or HMO. A clinician can use the information for simplification and effectiveness of his decision making or as a data/knowledge base background. An HMO could for example receive information of a clinical trial, such as drug efficacy and the costs of the drug use. Analysis of information in the data infrastructure as illustrated in FIG. 14 can include generation of a trajectory, fuzzy logic guidance, collaborative filtering prediction, disease maps, and data reports for clinical trials or new drug discovery. Examples of applications of a data infrastructure include reports (public or private), alerts (for example alerts of a user, clinician, clinical trial, or a pharmacy), and dynamic, adjustable trials.

Also demonstrated in FIG. 14 is the hierarchy of information received by the exemplary operating system from monitoring devices. The devices and operating system can monitor and release drugs if necessary. In a preferable embodiment, the devices monitor analytes in a bodily fluid. For example, when monitoring blood, the devices may be capable of executing prescription blood tests for a clinical or preventative setting or evaluate drug systems as demonstrated.

In an aspect, a system is disclosed that solicits input from the user or his agent (for example, a physician) to facilitate a conversation between the subject and his agent about the status of the person's health at a time. Examples of input that can be solicited by a system include, but are not limited to, establishing alert levels, medical notation, and personal notation. The system can acquire clinically relevant information about a person and place the information in a physiologically-reasonable context. Examples of clinically relevant information include, but are not limited to, age, gender, race, medical history, and genomic information.

In an embodiment, time dependent data can be representative of overall clinical health or response, including a diagnosed disease condition that requires monitoring, a response profile for a particular drug or combination of drugs, or subject observed observations of his health.

Calculated or observed information can be provided to a user. Examples of users include, but are not limited to, a patient, a physician, a clinical monitor for a clinical trial, and other medical personnel.

Information can also be integrated into a central repository for inclusion into, for example, a medical record or a clinical trial report.

Figure 15:
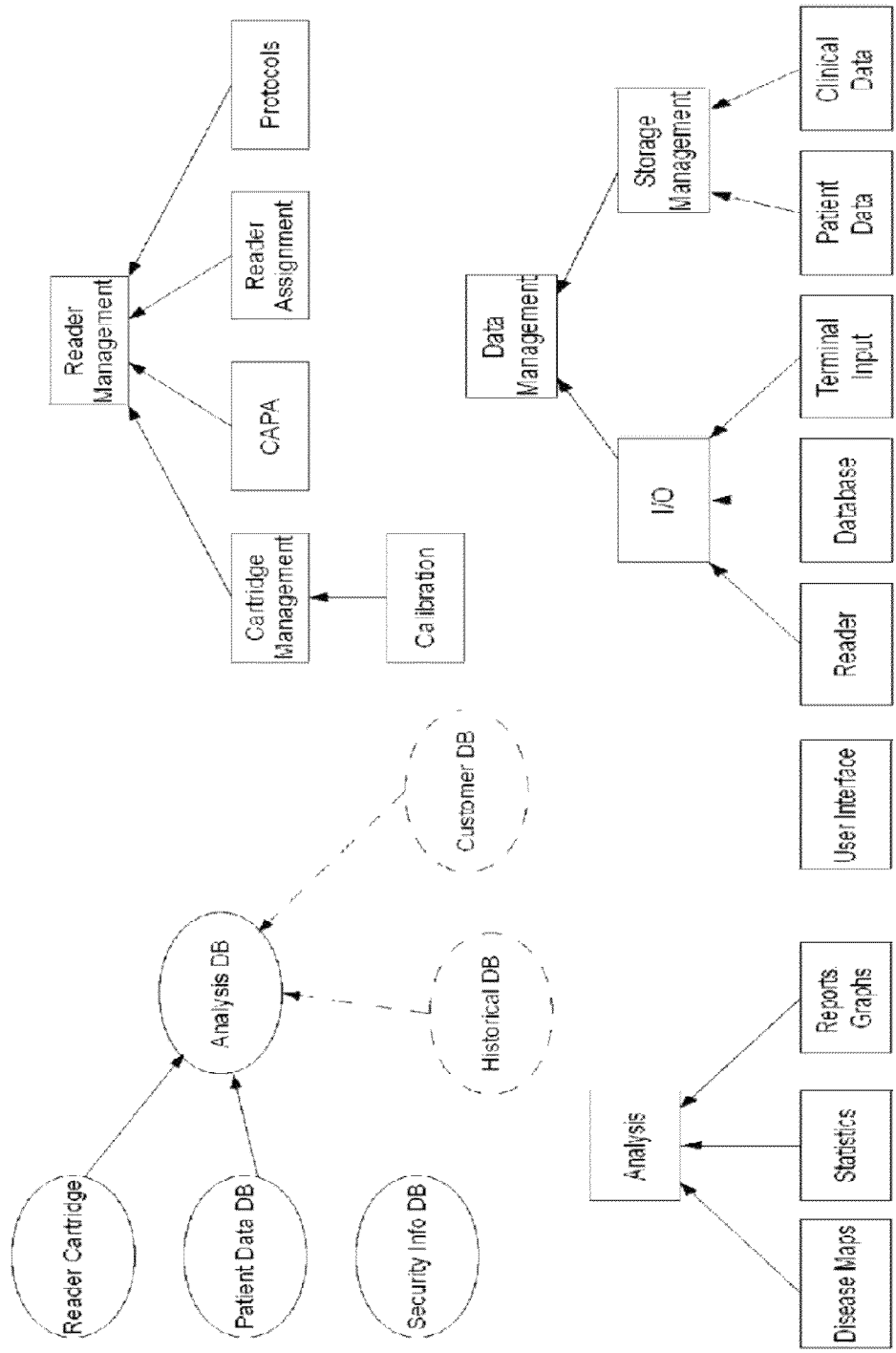
FIG. 15 demonstrates an exemplary system of the invention wherein an analysis database can receive information from a database containing data from a reader or cartridge database, historical databases, a patient database that can contain data entered by a patient, and a customer database.

FIG. 15 demonstrates an exemplary system of the invention wherein an analysis database can receive information from a database containing data from a reader or cartridge database, historical databases, a patient database that can contain data entered by a patient, and a customer database. Other features of a system of the invention are demonstrated in FIG. 15. The system is capable of performing analysis on data received by the system. The analysis can be any method as described herein and can include developing or utilizing a disease map, using statistics for a statistically analysis of information within the system, reports or graphs, and/or a combination of the different methods as described.

FIG. 15 also illustrates a user interface that may be utilized in a system of the invention. The user interface can interact with any of the components demonstrated in FIG. 15. In a preferable embodiment, the user interface allows a user to interface with the system to determine test data or analysis outcomes, such as physiologically relevant information. The user interface may be a touch screen, monitor, keyboard, mouse, or any other item that allows a user to interact with a system of the invention as would be obvious to one skilled in the art.

As shown in FIG. 15, a system can be utilized to manage a reader or point-of-care device. This can include management of a cartridge to be inserted into the reader for measurement of data. For example, the system can provide the reader a protocol for running an immunoassay of the cartridge. A system of the invention can also provide information to the reader for calibration of the immunoassays run on the cartridge that are run or executed by the reader. Reader management can also include information for assigning the reader for the appropriate reading system for reading an immunoassay from a point-of-care cartridge. Reader management can also include corrective and preventive actions (CAPA), which is an instrument of integrated and comprehensive compliance management. An element of the CAPA approach is an effective and systematic processing of quality deficiencies, errors and malfunctions with the goal to provide appropriate corrective actions and consistently prevent a reoccurrence of non-conformance situations. The CAPA strategy was developed by the Food and Drug Administration (FDA) for the inspection of medical products.

Systems and methods described herein can be used for pharmaceutical clinical trials. In some instances, the systems and methods accelerate trial timelines by an average of 18 months. In some instances, a system or method herein may provide dose-response and efficacy dynamics profiles in less than 18 months, less than 15 months, less than 12 months, less than 10 months, less than 9 months or even less than 6 months. Real-time pharmacokinetics and pharmacodynamics may provide better efficacy and more safety information. The methods herein may also decrease the risk of toxicity slowing approval or restricting use by shifting dose across: sub-populations, concomitant medications, and multiple indications. In other instances, a system or method herein can improve predictive visibility into pathway dynamics. A model as describe can produce predictive insights and power strategic decisions. A system can support communications with regulatory authorities internationally and can facilitate 'learn and confirm' strategy for adaptive clinical trials.

A system herein can include a data management system. The data management system can be operated through a plurality of devices or systems, or by a single central server. An example of data management of a system of the invention is shown in FIG. 15. A data management system can receive input or output from, for example, a point-of-care reader, a database (such as an analysis database or a historical database), and a terminal (such as a user interface). A data management system can also conduct storage management, for example, storage of a patient's individual data or storage of information related to a particular disease or drug profile. For example, if using a system and/or method of the present invention to conduct a clinical trial on an experimental drug, the data management and storage management systems can receive data from the point-of-care from a reader, and then store the information in databases for analysis of the data. Both the patient data and the analysis data may then be stored for future use of a system. For example, if one side effect is noted in a patient in Phase I of a clinical trial, that side effect information may be used for the analysis of results of a patient in Phase III of the clinical trial. As another example, a diabetic individual may receive a glucose measurement at an earlier time, which may then be used to evaluate the condition of the individual at a later time following another measurement.

Example 1

Prostate Cancer and Anti-Angiogenesis Treatment

A Phase I or Phase IIa clinical trial for treating a subject diagnosed with prostate cancer with an anti-angiogenic drug allows for dose adjustments during the trial. The subject is monitored over a course of time during the clinical study. The method of action of the anti-angiogenic drug is to halt the growth of blood vessels in and around the tumor, thereby depriving the tumor of adequate blood supply. This may induce ischemia and nutritional necrosis in the tumor, thereby debulking the tumor.

After the method of action is determined, discrete clinical outcomes are chosen by medical personnel, such as a physician or clinical monitor. The discrete clinical outcomes chosen in this example are complete response (CR), partial response (PR), non-response (NR), and adverse drug reaction (ADR). The ADR related to the anti-angiogenic drug is hypertensive encephalopathy in this example.

Six biomarkers representative of the clinical outcome of the subject with prostate cancer are chosen to define the discrete clinical outcomes. The biomarkers are PSA, TPS, hK2, VCAM-1, Endothelin-1, and 6-keto-PGF-1-$\alpha$. Using these biomarkers and the corresponding historical data on the progression of prostate cancer treatments with anti-angiogenic drugs as well as data from other subjects in the clinical trial, a cluster analysis is performed. Each discrete clinical outcome is assigned to a centroid of one of the clusters.

Before the subject is treated with the drug, the subject is assigned a position in the probability space based upon the subject's data from the relevant biomarkers. The probability of the subject belonging any of the discrete clinical outcome classes is determined using the Mahalanobis distance, from which a probability is calculated using a Bayesian estimation. The result of this calculation returns the four probabilities corresponding to the four clinical outcomes of the example. The position of the subject is determined by plotting the four probabilities in the probability space.

The probability space corresponding to four clinical outcomes is graphically displayed as a square in two dimensions. The user of the model, in this example, medical personnel, establishes rules for the medical condition of the subject based the subject data's position and/or trajectory in the probability space. Each discrete clinical outcome has a line representing the rule established by the medical personnel, as shown by the dashed lines in FIG. 16. When the subject crosses the dotted line towards the CR or PR conditions, the subject is substantially free of ADR and has improved his/her prognosis.

Figure 16:
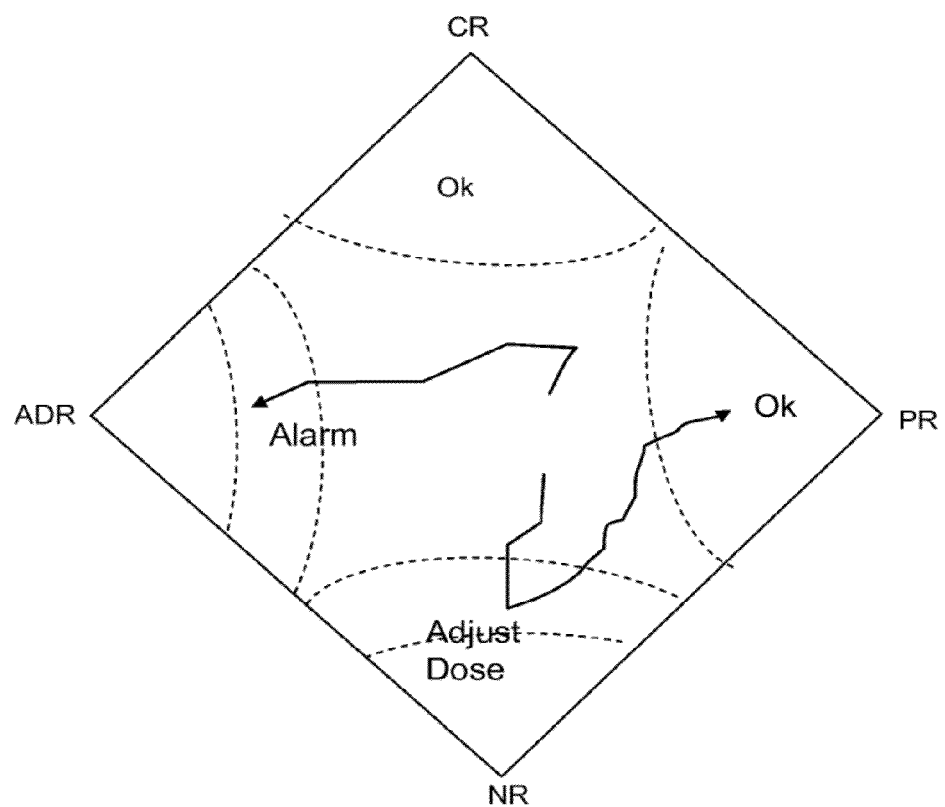
FIG. 16 illustrates exemplary trajectories of two subjects in a probability space representing prostate cancer discrete clinical outcomes.

In FIG. 16, the trajectories of two different subjects are plotted. Subject 1 has a trajectory that starts in the middle of the probability space and then heads towards the ADR condition. In this example, the medical personnel may notice the trajectory's speed or acceleration and intervene in the treatment. When Subject 1's trajectory crosses the dotted line towards the ADR condition, an alarm is activated. The medical personnel react accordingly.

Subject 2 has a trajectory that heads towards the NR condition. The dose of the anti-angiogenic drug treatment is adjusted corresponding to the rules established by the medical personnel. After the adjustment of the dose, the trajectory heading changes towards the PR condition. The example illustrates a method and embodiment of the invention for monitoring a clinical trial.

Example 2

Sepsis and Anti-TNF Treatment

Subjects with confirmed or suspected sepsis or systemic inflammatory response syndrome (SIRS) are treated with an anti-TNF therapeutic during a Phase IIb (dose adjustment allowed) or a Phase III (no dose adjustment allowed) clinical trial. The subject is monitored over a course of time during the clinical study. The method of action of the anti-TNF drug is anti-inflammatory. The drug is aimed at preventing or circumscribing downstream sequellae of sepsis. Typically, the anti-TNF drug is given in conjunction with a broad spectrum antibiotic.

After the method of action is determined, discrete clinical outcomes are chosen by a physician. The discrete clinical outcomes chosen in this example are response (R), non-response (NR), and four sequellae (disseminated intravascular coagulation (DIC), acute respiratory distress syndrome (ARDS), acute liver failure (ALF), and acute renal failure (ARF))

Twenty biomarkers representative of the medical condition of the subject with confirmed or suspected sepsis are chosen to define the discrete clinical outcomes. In this example, the biomarkers fall into multiple categories to monitor the different discrete clinical outcomes as defined by the physician. Lipoprotein Binding Protein (LBP) biomarkers measure infectious growth and the R and NR conditions. The LBP biomarkers are LBP, TNF, CRP, IL-6, and IL-8. Biomarkers that are relevant to the DIC condition are von Willebrand's factor, Protein C, thrombin, procalcitonin, neopterin, and PAF-1. The biomarkers of the ARDS condition are von Willebrand's factor, IL-6, IL-8, IL-1, and TNF. The biomarkers of the ALF condition are ALT, AST, GGT, LDH, Alkaline phosphatase, bilirubin, and Protein C. The biomarkers of the ARF condition are Creatinine and Cystin C.

Using the biomarkers described in this example and the corresponding historical data on the progression of sepsis and the treatment of sepsis with anti-TNF therapeutics as well as data from other subjects in the clinical trial, a cluster analysis is performed. Each discrete clinical outcome is assigned to a centroid of one of the clusters.

Before the subject is treated with the drug, the subject is assigned a position in the probability space based upon the subject's data from the twenty biomarkers. The probability of the subject belonging to any of the discrete clinical outcome classes is determined using the Mahalanobis distance, from which a probability is calculated using a Bayesian estimation. The result of this calculation returns six probabilities corresponding to the six clinical outcomes of the example. The position of the subject is determined by plotting the six probabilities in the probability space.

Figure 17:
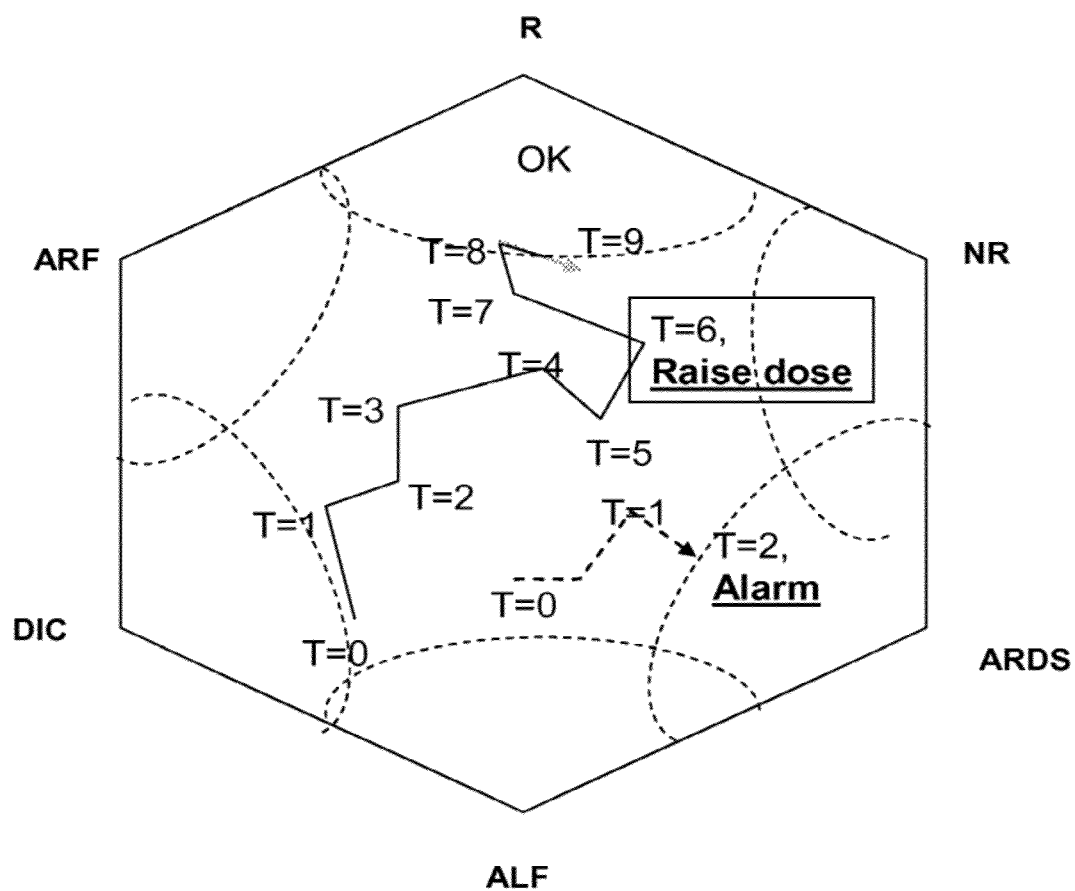
FIG. 17 illustrates exemplary trajectories of two subjects in a probability space representing clinical outcomes of a subject developing sepsis.

The probability space corresponding to the six discrete clinical outcomes is graphically displayed as a hexagon in two dimensions. The physician establishes rules tracking non-responsive subjects and possible advent of sequellae. The rules are plotted on the hexagonal graph as lines as illustrated in FIG. 17. The medical condition of the subject is based the subject data's position and/or trajectory in the probability space.

In FIG. 17, the trajectories of two different subjects are plotted. Subject 1 has a trajectory that starts with a high probability of being a member of the DIC condition. However, as the subsequent time points are taken, the subject trajectory moves away from the DIC condition and towards the NR condition. When the physician notices the trajectory's speed and heading, at T=6, he raises the dose. At T=9, the subject's position in the probability space has a high probability of being part of the R condition. The physician assesses the medical condition of the subject at any point in time along the subject's trajectory.

Subject 2 has a trajectory that begins in the middle of the probability space and heads towards the NR condition at T=1. However, at T=2, the subject's position and trajectory are in violation of the rule established by the physician and an alarm is sounded. The alarm alerts the physician that the subject has a high probability of suffering from one of the dangerous clinical outcomes of sepsis.

Example 3

Diabetes and Insulin Sensitization

Subjects with non-insulin-dependent Type 2 diabetes are treated with a commercially available insulin sensitizer and are monitored for efficacy and safety wherein the primary ADR of concern is congestive heart failure (CHF). The subject is monitored over a course of time during the clinical study. The method of action of the insulin sensitizer involves re-establishing insulin sensitivity in the subject via antagonism of a nuclear receptor in the adipose tissue and the liver. The insulin sensitizer and method of action act to increase glucose uptake in the peripheral tissues and thus reduce the circulating glycemia.

A subject and a physician choose the best set of discrete clinical outcomes and rules for the subject based on personal information. The discrete clinical outcomes are response (R), non-response (NR), and adverse drug reaction (ADR). The ADR is congestive heart failure.

After the three clinical outcomes are chosen, biomarkers most representative of the medical condition of the subject are determined by discriminant analysis. The biomarkers representative of efficacy of the insulin sensitivity treatment are glucose, insulin, adiponectin, and resistin. The ADR of congestive heart failure identifies the representative biomarkers as Brain natriuretic peptide (BNP), amino-terminal-pro-BNP (N-BNP), atrial natriuretic factor (ANF), Troponin-C, Cardiac fatty acid binding protein, Myosin light chain-1, Myoglobin, MMP-9. Using these biomarkers and the corresponding historical data on the type 2 diabetes, a cluster analysis is performed. Each discrete clinical outcome is assigned to a centroid of one of the clusters.

Before the subject is treated with an insulin sensitizer, the subject is assigned a position in the probability space based upon the subject's data from the relevant biomarkers. The probability of the subject belonging any of the discrete clinical outcome classes is determined using the Mahalanobis distance, from which a probability is calculated using a Bayesian estimation. The result of this calculation returns three probabilities corresponding to the three clinical outcomes of the example. The position of the subject is determined by plotting the three probabilities in the probability space.

The probability space corresponding to three clinical outcomes is graphically displayed as a triangle in two dimensions. The physician and subject establish rules most important to the individual diabetic subject. The rules are to track the NR and ADR conditions. When the probability of belonging to the ADR condition class increases beyond a boundary defined by the rule, an alarm is triggered. The dose is increased according to a rule when the subject has a high probability of being a NR.

Figure 18:
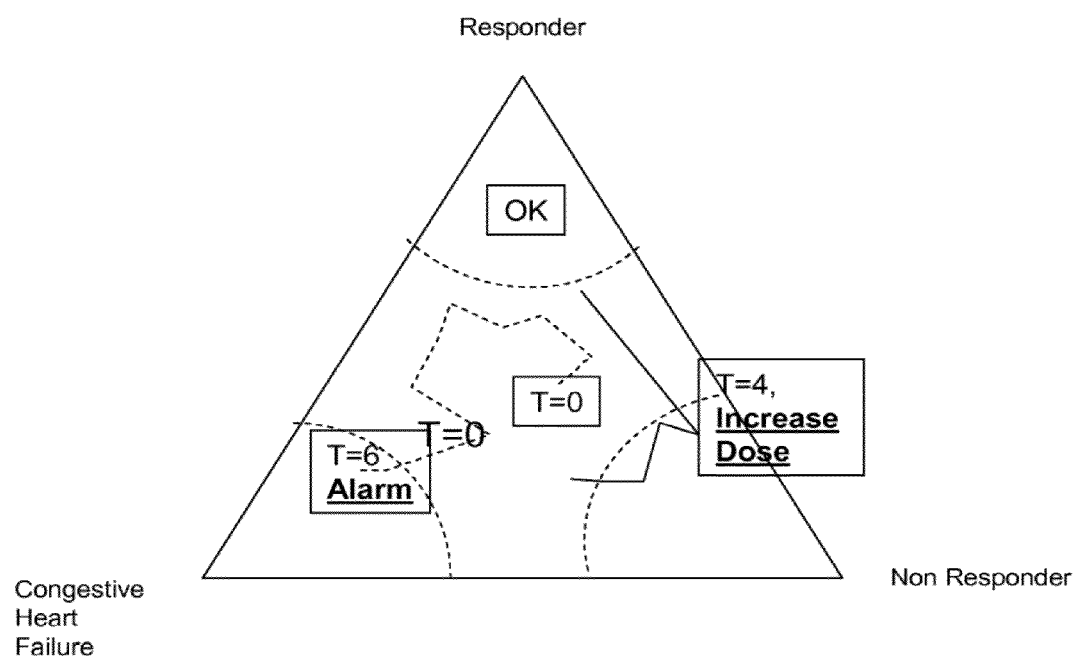
FIG. 18 illustrates exemplary trajectories of two subjects in a probability space representing the medical condition of diabetic subject using an insulin sensitizer.

In FIG. 18, the trajectories of two different subjects are plotted. Subject 1 has a trajectory that starts in the middle of the probability space and then heads towards the ADR condition. In this example, the subject may notice the trajectory's speed or acceleration and ask the physician if a change in treatment is necessary. When Subject 1's trajectory crosses the dotted line towards the ADR condition, an alarm is triggered. The subject may react by going to the hospital.

Subject 2 has a trajectory that heads towards the NR condition. The dose of the insulin sensitizer is adjusted corresponding to the rules established by the physician and the subject. After the adjustment of the dose, the trajectory heading changes towards the R condition. The example illustrates a method of the invention for monitoring a diabetic subject taking a commercial insulin sensitizer and, with the help of a physician, monitoring the subject's own condition at home.

Example 4

Graphical Representation of the Clinical Outcome of a Subject

The example demonstrates a method for communication of the results from the mathematical model to a user. The method is to plot a series of points and vectors in a space bounded by a polygon. The vertices of the polygon represent the centroids of clusters of discrete clinical outcomes. The position of the points represents the probability that the subject data belongs to each centroid. The probability of the point belonging to the discrete clinical outcome is inversely proportional to the distance of that point from the vertex. Since the vertices represent all the significant clinical outcomes, the sum of the probabilities for a given point must be 1.

A set of vectors is created where each value of a vector represents the probability of membership in each of the clusters. The modulus (magnitude) of the values is the probability and the argument (angle) of the vector points to a vertex, which are equally spaced. The vectors are summed and the resulting point is located in the composite probability space.

TABLE 1

| Time Point | Discrete Clinical outcome | | | | |
|---|---|---|---|---|---|
| | R | NR | ADR1 | ADR2 | ADR3 |
| 1 | 20 | 20 | 20 | 20 | 20 |
| 2 | 25 | 10 | 25 | 20 | 20 |
| 3 | 30 | 10 | 20 | 20 | 20 |
| 4 | 40 | 10 | 10 | 20 | 20 |
| 5 | 50 | 10 | 10 | 10 | 20 |
| 6 | 60 | 10 | 10 | 10 | 10 |
| 7 | 80 | 10 | 5 | 5 | 0 |
| 8 | 100 | 0 | 0 | 0 | 0 |

For example, in Table 1, each row represents the position of one point. The columns, labeled at the top, represent the probability that the point is a member of that cluster. So, in the first row, the probability that the point is in cluster "R" is 20%, that it is in the cluster "NR" is also 20%, and so on.

Figure 19:
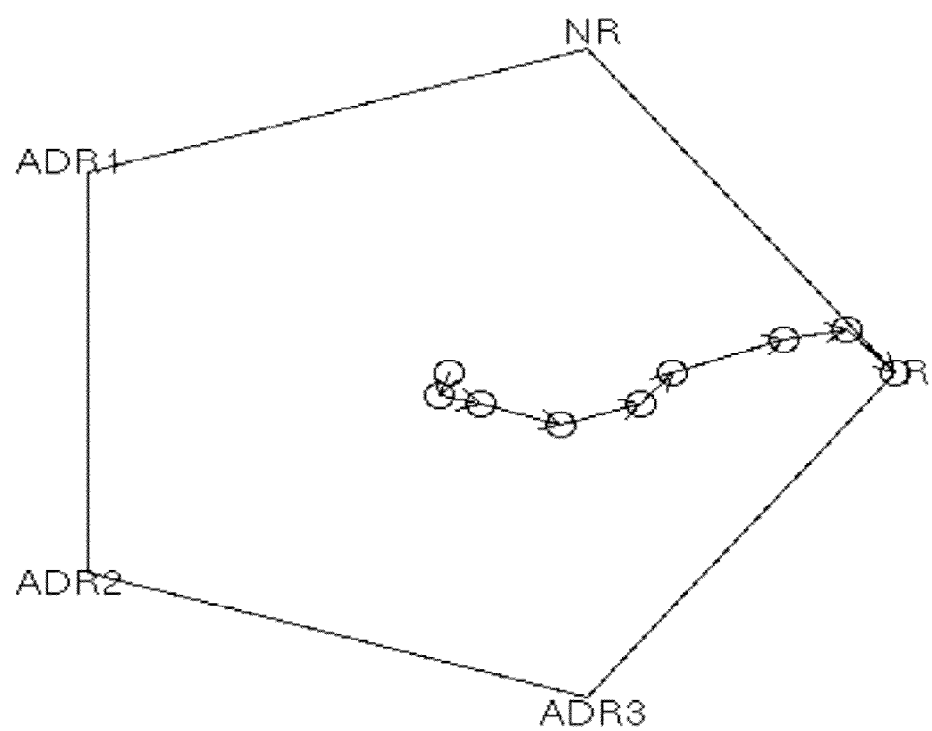
FIG. 19 illustrates a method of graphically representing a trajectory of subject data in a probability space in two dimensions.

For the data in the table a graphical representation is created as illustrated in FIG. 19. We see that the surrounding polygon has five vertices, each labeled as one of the columns in the tabular data above. The first point of the set, at the tail of the chain of arrows, is at the center of the drawing, indicating that the percentage probability that the point is in any of the clusters is the same as the others. In this example, as the trajectory grows through time, the probability of the subject data reaches a final point that has 100 percent chance of being in cluster "R" and zero percent chance of being elsewhere. Correspondingly, the final point is at the "R" vertex.

Figure 20:
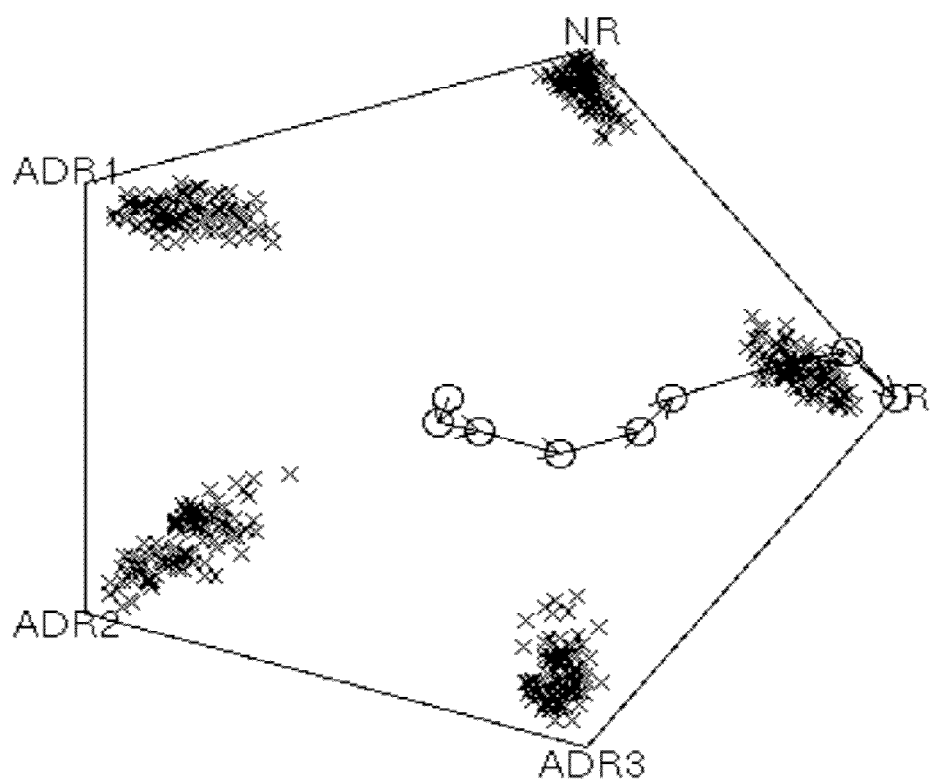
FIG. 20 illustrates a method of graphically representing a trajectory of subject data in a probability space in two dimensions and the position of the data for defining discrete clinical outcomes.

Additional information can be included in the output of the probability space, including the points representing the data of the discrete clinical outcomes that defined the clusters and centroids. FIG. 20 illustrates a graphical representation of the cluster data points.

Example 5

Drug development is an extremely risky proposition. Over the last decade, the failure rates for clinical programs have been identified as high 90% with an amortized cost of nearly one billion dollars per approved drug. These failures are due to any number of factors. These include, but are not limited to: a faulty hypothesis as to a target's role in the evolution and pathophysiology of the disease; the testing of that hypothesis in an inappropriate, and non-predictive, animal model; a faulty hypothesis regarding a compound's MOA; inappropriate dosing schedules for individuals within target subpopulations, including inappropriate pharmacokinetics/pharmacodynamics (PK/PD) characteristics; and developing untoward physiological effects (for example, Adverse Drug Reactions—ADRs) in some segments of the patient population and thus decreasing the therapeutic index for the compound in that population.

This example demonstrates using a Type 1 biomarker for a compound within a particular therapeutic area to: (a) validate the underlying hypothesis regarding the method of action for the test compound; (b) identify, and then enrich, the appropriate responder subpopulation in a confirmatory trial; and (c) develop a truly adaptive dosing protocol based on the individual PKs and PDs of the responder population.

A real-time monitoring system is used identify the emergence of these characteristic subpopulations earlier rather than later, to efficiently manage and control the clinical trial and allows the clinical research team make precise decisions regarding trial management. On a patient by patient basis, it dynamically identifies the compound's effects in one particular trial subject, and then physically titrating that patient's dosing regimen to accommodate a truly adaptive "Learn and Confirm" model of drug development.

Longitudinal sampling of proteins is performed with each patient, wherein the proteins represent both the pathophysiology of the disease and the method of action of the compound. A standard cluster analysis is applied at each sample time point in the longitudinal sampling space that is consistent with the evolutionary dynamics of the pathophysiology of the disease, and the purported method of action and PD of the test compound.

Identification of the dynamics of the emergence of separate subpopulations within the trial sample population can be performed with two complementary clustering statistics: Cubic Clustering Criterion (CCC) and the Pseudo-F which help the end-user establish the number of clusters emerging within the geometry as demonstrated in FIG. 21.

The end-user uses both the statistics highlighted above and a visual inspection of the cluster scatter plots to make the final determination as to how many distinct subpopulations exist in the clinical study. Guiding this determination will be a fore-knowledge of the number of treatment (cohort) arms, and any fore-knowledge as to the character of a possible ADR. The methodology will suggest a number of clusters to the end user, and will then present each patient as to his/her cluster assignment. The cluster assignment and the known assignment of a patient to a treatment cohort or ADR outcome are then used standard assignment statistics to calculate both the sensitivity and specificity of the assignment rule.

After determining that the clusters are reasonably specific, the dynamic trajectories of the centroids of each cluster are characterized, their separation speed, and the distribution of speed and directions of each patient in each cluster. If, for example, one cluster of patients is fairly homogeneous in that they were all exposed to the compound at a given dose, and if the distribution of distances, speeds, and directions, suggest that some may be slow responders, then the end user may decide that those patients should receive a higher dose.

Based on the assumptions developed herein, in silico populations of virtual patients are created for each hypothetical patient subclass. A time dependent Monte Carlo simulation is run to identify the emergent clusters. After the simulation is run, a new set of mean vectors and covariance structures is established and the simulation studies are repeated. The sensitivity and specificity of the clustering assignment rule for each dynamic is measured and graphically plot as a receiver operator curve, wherein the diagnostic variable will be the time at which the clusters were suggested.

Figure 21:
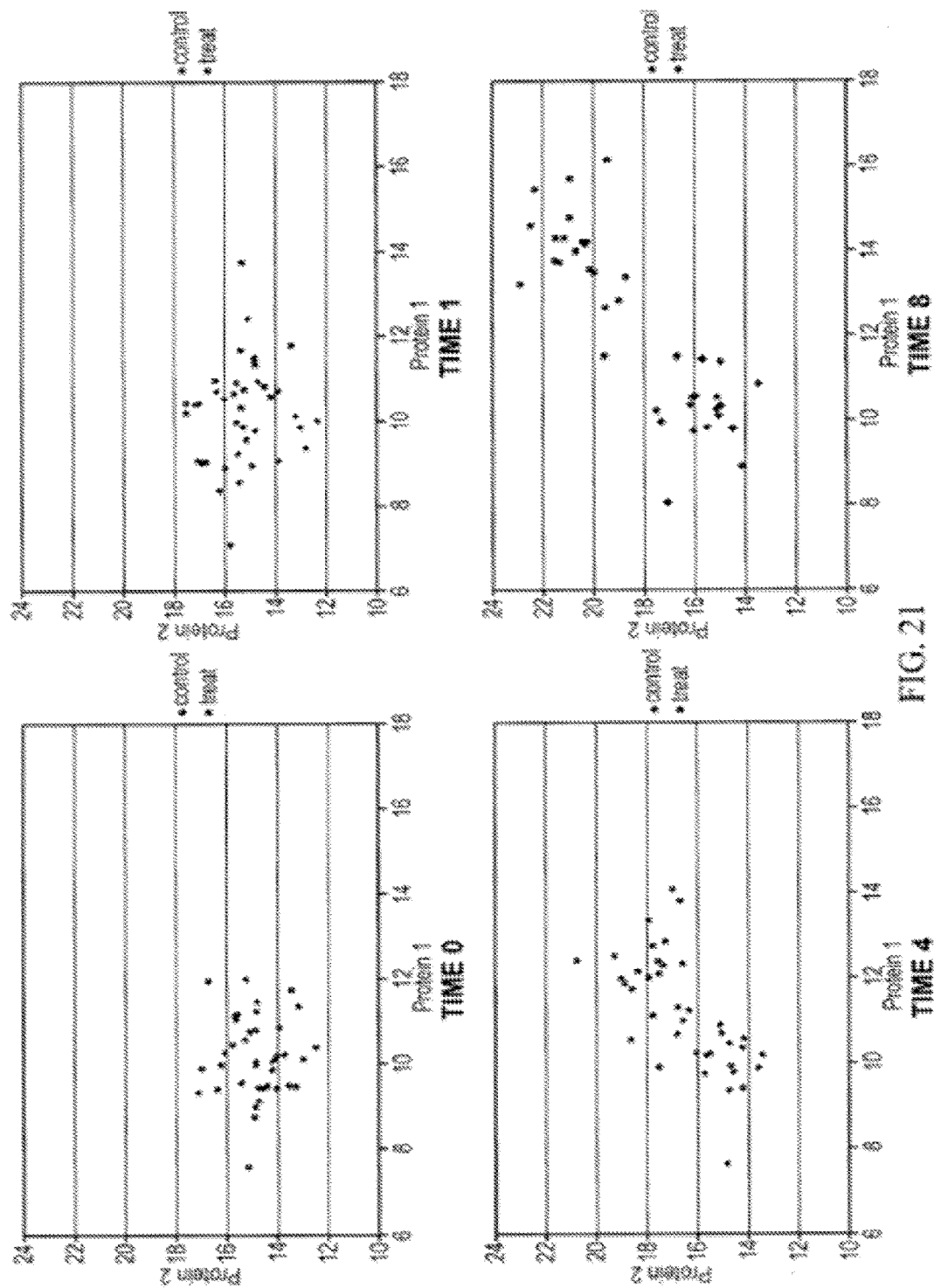
FIG. 21 demonstrates a dynamic subpopulation emergence based on cluster analysis of a Monte Carlo simulation of a two-cohort clinical design.
Figure 22:
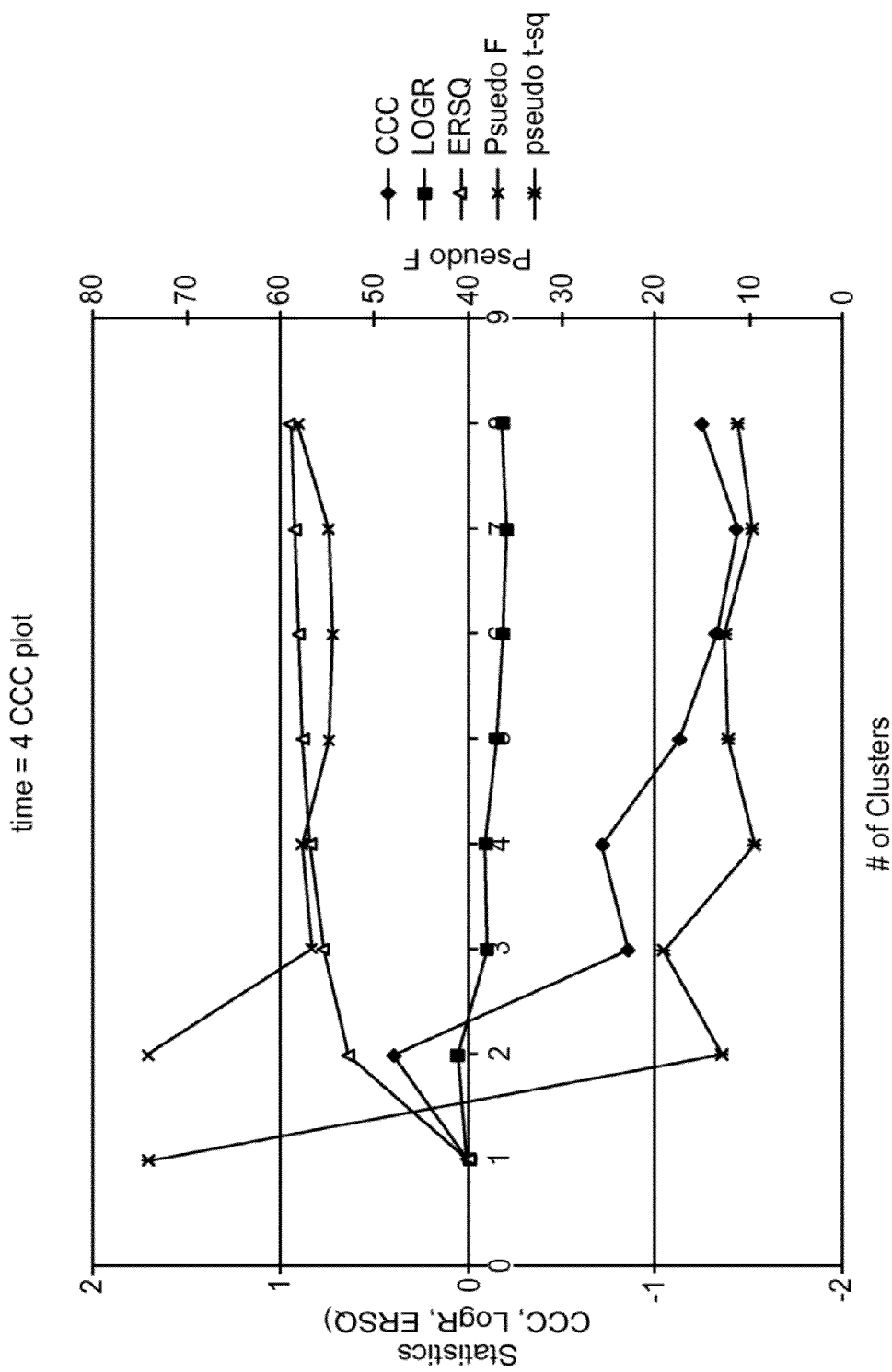
FIG. 22 demonstrates plots of the cluster calling statistics versus the hypothetical number of clusters.
Figure 23:
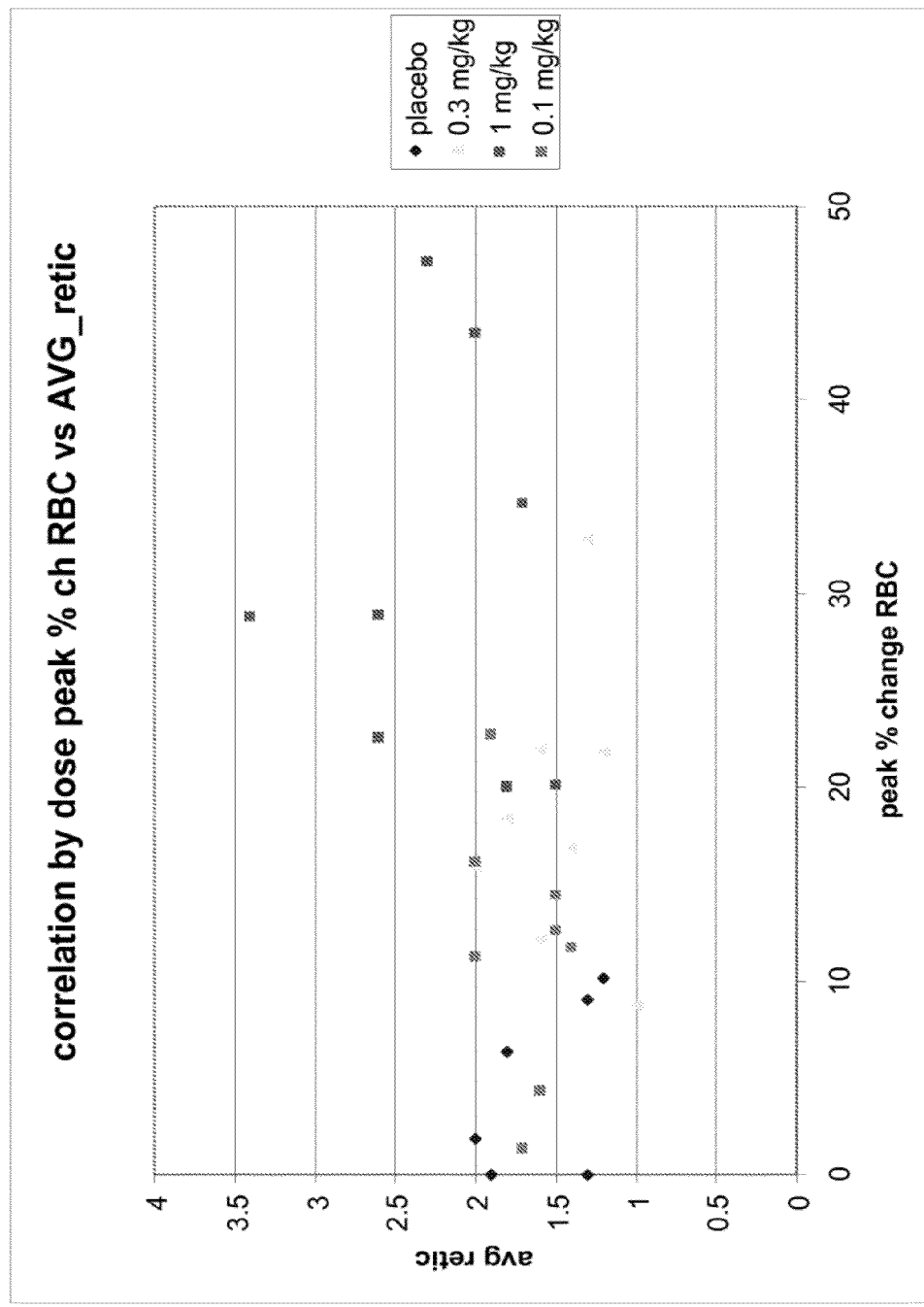
FIG. 23 illustrates markers of clinical effect with the segregation of the marker space as a function of dose at the end point of a clinical study.

Results of the emergent dynamics by Monte Carlo simulation of the described methods described in this example and results in the following emergent dynamics as shown in FIG. 21. FIG. 21 demonstrates a dynamic subpopulation emergence based on cluster analysis of a Monte Carlo simulation of a two-cohort clinical design. At Time=4 there is significant evidence for the emergence of two clusters while by Time=8 the bifurcation is complete and the sensitivity and specificity of the method are both 100%. FIG. 22 demonstrates plots of the cluster calling statistics versus the hypothetical number of clusters at Time=4. FIG. 23 illustrates markers of clinical effect with the segregation of the marker space as a function of dose at the end point of a clinical study.

Example 6

Identification of Type 1 Biomarkers Indicative of Periodic Dosing Regimes

Periodic dosing, as a therapeutic strategy, is a mainstay for the treatment of many chronic diseases or conditions. Foremost among these are anti-cancer chemotherapy regimens and treatments for autoimmune diseases. Whether therapeutically or in the context of an adaptive clinical trial, the ability to both monitor and characterize efficacy and toxicity profiles for a particular dosing regimen in any given patient provides the clinical professional important information regarding the ultimate efficacy of his/her dosing strategy. The benefit of such a feedback mechanism is that the feedback is timely and represents the mechanism of action and clinical impact of the compound. For example, in cancer chemotherapy, the feedback is provided by imaging technologies that help quantify tumor burden, which in many cases is not timely.

This example characterizes the periodicity of the molecular efficacy measures to identify trends and other measures of clinical relevance (for example, increasing refractory response) to further aid in clinical decision making. As demonstrated herein a real-time feedback monitoring system can account for the periodicity of the dosing regimen and characterizes any clinically trends in the data.

The system can be a statistically valid and robust methodology which dynamically characterizes the time-dependent profiles of molecular markers of drug activity in periodically treated patient subpopulations which then uses that information as a real-time feedback monitor for optimizing the therapeutic regimen.

The protein profiles of a treated population act in accordance with the underlying hypothesis regarding a compound's mechanism of action, they should, as a conglomerate pattern, reflect the periodicity of the treatment regimen, and taken as a whole, act as a Type 1 biomarker for compound activity at the site of action. Additionally, if there is evidence that the periodic expression of these profile proteins changes with time, the trend of that change allows a clinician to adjust the dosing regimen for example in frequency and/or dosage to individualize the therapy.

Applying a time series-based statistical methodology to the longitudinal (within an individual patient) protein profiles systematically accounts for the periodicity of a given dosing regimen within an individual patient and using that information to identify and characterize the emergence of any clinically relevant trends in the response. This knowledge can then be used to both monitor a therapeutic regimen in an individual patient and to design and manage the dynamics of an adaptive clinical trial.

By developing a valid longitudinal Type 1 biomarker for a compound's activity in the context of a periodic dosing regimen will: (a) validate the underlying hypothesis regarding the method of action for the test compound; (b) identify potentially relevant clinical conditions comprising: growing refractoriness to the compound, target response to the regimen, and then adjust, as appropriate, the frequency or dosages of the treatment itself; and (c) develop an adaptive dosing protocol based on the individual PDs of the responder population.

Using real-time monitoring and feedback to identify the emergence of these characteristic dynamics aids the clinician to make more precise decisions regarding patient treatment and/or trial management.

Figure 24:
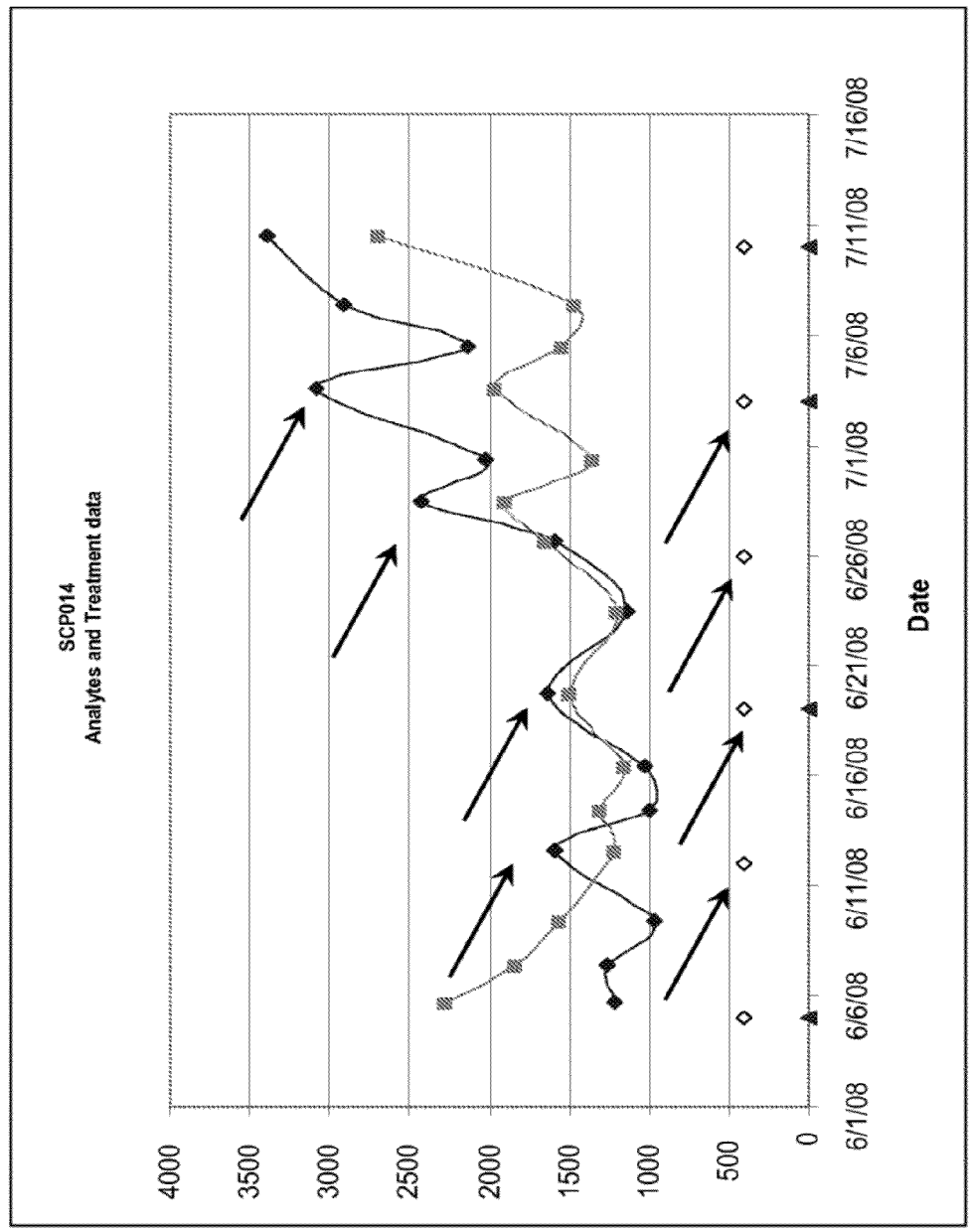
FIG. 24 demonstrates patient data showing the seasonality of two type 1 biomarkers over time.

A statistical Time Series analysis is used to characterize the periodicity or seasonality of marker proteins in a patient subjected to periodic treatments similar to those employed in cancer chemotherapy, weekly methotrextate injections. The system adjusts for the seasonality of the data train as shown in FIG. 24 and de-trends the responses as necessary, a one or two lag differencing scheme as applied to Autoregressive Integrated moving Average (ARIMA) Models, to characterize the actual response profile of the patient to the therapy stream. FIG. 24 demonstrates patient data showing the seasonality of two type 1 biomarkers over time. If two or more proteins markers are identified as markers, any temporal relationships between them (for example without limitation, the levels of drug in the blood and/or clinical readout) can be identified and characterized using Distributed Lags analysis in the same modeling context. Each analysis depends on explicit characterization of the time-time correlations observed in the time series, the Autocorrelation Function (ACF) and its related Partial Autocorrelation Function (PACF)). Each of these functions can be represented as a vector of correlations which are functionally dependent on the lag between measures. The functions can be used to identify linear trends in the data, periodicity in the data, and nonlinear curvature dynamics in the data. The functions themselves can be visualized for inspection using histograms called correlograms. Once the data is de-trended and the periodicity accounted for, the individual spikes in the marker profiles are analyzed to see if the compound is working as expected.

The first step involved in developing this methodology is identifying those proteins that best represent both the pathophysiology of the disease and the purported method of action of the compound. Once established, these proteins are sampled longitudinally in each patient.

Based upon the expected seasonality of the treatment regimen and the frequency of the therapeutic dosages, an appropriate sampling frequency is established to ensure that the suspected periodic expression of the marker proteins will be captured in the sample data sets.

The system automatically generates and inspects difference time series with 0, 1, or two lag differences comprising ARIMA (0, 0, 0), ARIMA (0, 1, 0), and ARIMA (0, 2, 0) models and compares them to the best fit through Root Mean Square Error, thus appropriately de-trending the data to make the series stationary. Once a stationary series has been established, the de-trending parameters comprising the slope of a linear trend line is estimated from the data, and an ACF and PACF for the stationary series is generated.

Figure 25:
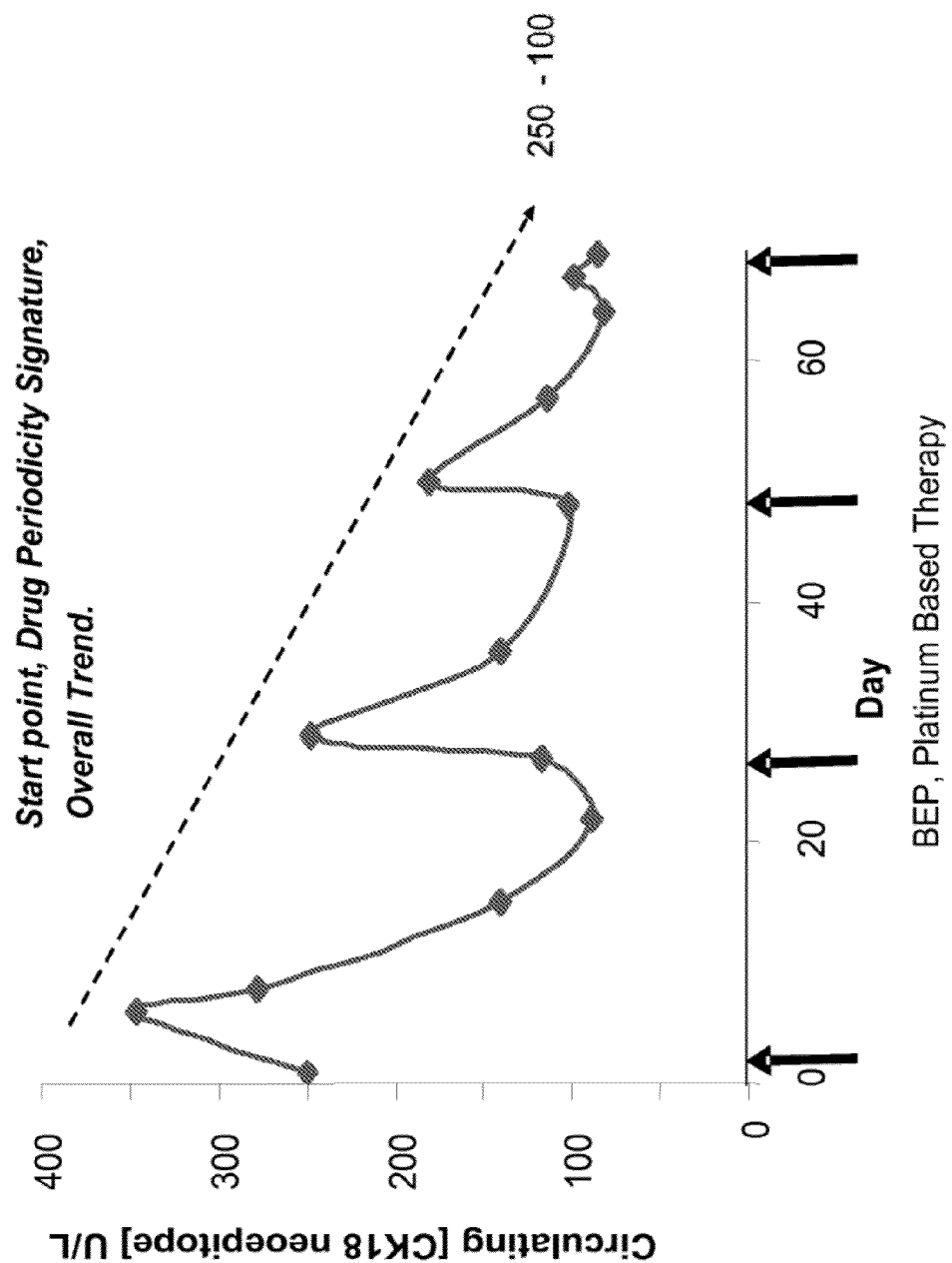
FIG. 25 demonstrates a time series of a biomarker value versus the time of chemotherapy delivery.

Any periodic expression patterns are identified and characterized as the period of the peaks and their subsequent amplitudes. An example of this is shown in FIG. 25 demonstrating a time series of a biomarker value versus the time of chemotherapy delivery.

When multiple time series are involved comprising two or more protein markers and/or levels of compounds in the blood, a distributed lags analysis is performed to identify and characterize the correlations between the series and their lags. The methodology identifies the dynamics of the emergence of protein marker wave trains and to relate these back to clinically relevant events and/or the dosing schedule of the regimen.

A Monte Carlo simulation of the methods described above using four time series were generated using a stationary time series, a time series with linearly increasing slope, a time series with exponentially decreasing affect to mimic patient-drug attenuation, and a stationary time series with linearly decreasing peaks, to model patient-drug adaptation or up-regulation of metabolic pathways.

Example 7

Time to Fever Spike and Sepsis from Time Series Measurements of Levels of Circulating Pyrogens and Other Biomarkers A patient with Acute Myeloid Leukemia (AML) undergoing in-patient chemotherapy was monitored using the methods and systems described herein with sampling of blood every four to eight hours. The patient's temperature was also monitored frequently. IL-6 elevation (>1000-fold between consecutive measurements) was found at time designated zero in Table 2 and a significant decline >30% between consecutive measurements 14 hours later. Fever was first noted eight hours later. The methods herein would have anticipated the subsequent recognition of sepsis by 8 hours.

TABLE 2

| Time, hours | Event |
| --- | --- |
| 0.0 | First elevation of IL-6 |
| 8.4 | First fever |
| 14.3 | Significant decline in protein-C |
| 22.3 | Septic shock |
| 27.2 | Patient admitted to ICU |

The system identifies the relationship between the time to a fever spike during aggressive chemotherapy of leukemia resulting in fever and dramatically changed levels of circulating pyrogens (Protein-C, IL-6, Il-1beta, TNF-alpha, IL-10). This is performed by employing standard statistical modeling methodologies. The system can be generalized to other situations where sepsis occurs. It can also be employed for other situations where significant disease processes and outcome of therapy can be beneficially projected.

Science and engineering often involve using easy-to-measure variables, called factors or independent variable factors to explain or predict the behavior of other variables, called responses. When the factors are few in number, not significantly redundant (non-collinear), and have a well-defined, functional relationship to the responses, one can use multiple linear regression to characterize that relationship. However, if any of these three pre-conditions should fail, multiple linear regression may prove to be inefficient or statistically inappropriate. In that case, one may employ an alternative model building strategy termed Partial Least Squares Regression.

This methodology is particularly useful when there are many factors that might be highly co-linear, and when the relationship between independent variable factors and dependent variable response is ill-defined. The aim of this type of analysis is to construct a good predictive model.

Figure 26:
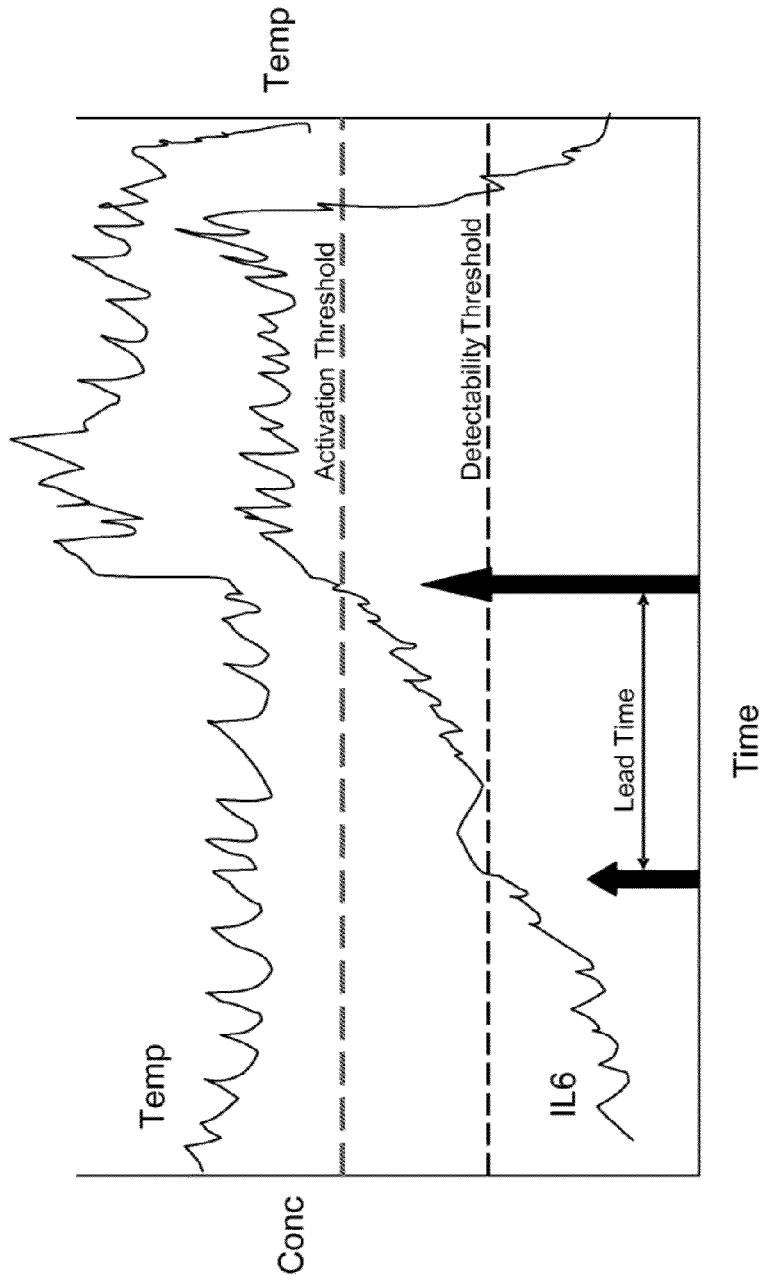
FIG. 26 demonstrates the relationship between parameters computed from circulating pyrogen levels measured over time and/or and the time-to-spike.

Anticipating the time to a Fever Spike based on statistical models using levels of several circulating pyrogens. FIG. 26 demonstrates the relationship between parameters computed from circulating pyrogen levels measured over time and/or and the time-to-spike (also labeled Lead Time). The rate of change and shape of the parameters over time is determined by the incidence, time of infection, extent of infection, numbers of organisms, virulence of the organisms, and the condition and genetic make-up of the patient. The activation threshold is the point at which the body physiology begins to generate a fever spike. The detection threshold is a parameter level at which some therapeutic intervention is indicated. The system determines the relationship between the pyrogen levels and the dependent variable in the model, Lead Time, enabling prediction of fever spike early enough to intervene with beneficial outcome.

This method and data provides enables anticipation of the time patients are most likely to experience a fever spike. The physician can then preempt and/or ameliorate the onset of the fever event, for example by providing prophylactic antibiotic therapy.

The treatment of patients with Acute Myelogenous Leukemia (AML) is used as an exemplary case. Such patients are often treated with a course of induction chemotherapy (inpatient chemotherapy typically using more than one drug and intended to eliminate all cancer cells). An undesired side-effect of the induction chemotherapy is usually febrile neutropenia. This occurs because infectious microorganisms can invade the patient due to the inactivation of active immunity by the chemotherapy. The definition of febrile neutropenia is the fever spike, a clinician defined state in which the patient's temperature measures greater than 39 degrees Celsius or in a six hour period two consecutive patient temperatures measured greater than 38.5 degrees Celsius.

Fever, as a defense mechanism, results from the effects exerted on the hypothalamus by circulating cytokines, called pyrogens. These cytokines emerge from the immune system during an inflammatory response. The best known of these are IL-6, IL-1 beta, and TNF-alpha. The purpose of this example is to identify a pattern of circulating pyrogens leading up to a fever spike, and, from them, build a model that best anticipates the time-to-spike.

The methods developed in the studies may be generalized to generate a monitoring means in other high-risk disease states and therapeutic procedures.

The system builds a statistical model characterizing the relationship between the time-to-spike and the circulating levels for two particular pyrogens, IL-6 and IL-1 beta. The system, while independent of measurement means, requires frequent sampling in the period prior to the fever spike (anywhere from 3 to 6 measures per day).

The first step involved in developing the methodology requires one characterization of fever in well defined categories and to identify, as closely as possible, the time of the first fever event. The definition chosen was that either the patient's temperature measures greater than 39 degrees Celsius or in a six hour period or two consecutive temperatures are recorded greater than 38.5 degrees Celsius.

Individual patient data for the circulating levels of IL-6, IL-1 beta, and TNF-alpha and other biomarkers were recorded in a database, based on the sampling interval. The samples in the study (3 measures per day at 8-hour increments) were subjected to post hoc analysis, and used to populate the model.

These markers were selected based upon a number of current studies which show that patients with Sepsis Syndrome have elevated levels of circulating IL-1 beta, IL-6, and TNF-alpha when compared with critically ill patients without sepsis and normal controls (Casey, L Annals of Internal Medicine (1993) 119; 8:771-778).

IL-6 predominately regulates the synthesis of CRP made by the hepatocytes (liver) in the acute phase response. Transcription of CRP is also regulated somewhat by TNF and IL-1. CRP is a pentraxin protein which binds to phosphocholine on bacterial cell walls, endogenous cell membranes, and apoptotic bodies. Inflammation caused by infection/sepsis, inflammatory and autoimmune disorders, traumatic injury, and some malignancies, CRP is seen in increased amounts making it a useful biomarker in monitoring sepsis and infection. CRP production is not affected by neutropenia. There is an abundance of literature which focuses on CRP levels during neutropenic fever and in diagnosing the severity of febrile incidences.

Protein C is anti-coagulant protein that is synthesized in the liver. It plays an important role in maintaining coagulation homeostasis. Protein C is activated by thrombin into an active protein which along with protein S and phospholipid as cofactors, it cleaves coagulation factors VIII and V thus inhibiting coagulation. Recently, Protein C's anti-inflammatory responses have been discovered.

Patients with sepsis and septic shock have Protein C depletion which may have a role in the pathophysiology of sepsis. Improvement was seen in a specific subgroup of patients by counteracting Protein C depletion by the addition of activated Protein C. Protein C can be used as a biomarker in the diagnosis of sepsis in patients and as a therapeutic agent. One study found that concentrations of Protein C are proportionate with severity of neutropenic sepsis at fever onset.

Ten adult leukemia patients receiving chemotherapy were enrolled. Blood samples were taken every 8 hours prior to the onset of the fever spike and then every 6 hours until the end of the observation period. Biomarker analysis was performed on these samples. Patient sampling of 8 hours prior to fever spike and 6 hours after fever spike observed.

A Partial Least Squares model was constructed based on the pre-spike (36 hour window) measures for IL-6, Ill-beta, and TNF-alpha and their sample-to-sample fold changes. Given the data set derived from this study, a minimal sampling period of 8 hours and a minimal window of 36 hours pre-spike is sufficient to derive an anticipative model of the time to spike.

Quantitative Biomarker concentration data was derived using well known ELISA immunoassay known to measure IL-6, Ill-beta, and TNF-alpha. Concentrations measured in pg/mL, and sample-to-sample fold changes in concentration were recorded and analyzed as follows.

The concentration data were first visually inspected for Gaussian normality. Because they were log normally distributed the data was transformed by calculating the log of the raw data measures. Based on these measures, an initial Partial Least Squares regression model was built that included all three pyrogens and their fold changes from sample to sample. This model characterized the amount of variation accounted for in the covariance structures of the dependent vectors (times-to-spike) and the independent vectors (pyrogen levels). In this data set there were more independent variables than degrees of freedom. To address the problem, standard statistical model building tools like top-down elimination and bottom-up addition were employed.

The full model (IL-6, TNF-alpha, and IL-1beta, and their sample to sample changes) accounted for the percentage of the variation in the whole model covariance structure and the percentage of the variance in the dependent variable (time-to-spike). Using feature selection processes comprising and not limited to bottom up model building and top down model building, a series of seven sub-models were developed.

The chosen model included log(IL-6), log(IL-1 beta), log (sample-to-sample fold change IL-6), log(TNF-alpha), and accounted for 93% of the total model covariance and 27.5% of the variance in the dependent variable (time-to-spike).

The model is given by a standard multiple linear regression equation with the following parameter set: intercept=36.5; log(IL-6)=−8.0; log(IL-6 fold change)=2.4; log(IL-1 beta)=−0.3; and log(TNF-alpha)=4.4. Each measure is a point-in-time measure at the observed time-to-spike. For example, 24 hours prior to the fever spike, the log of the concentrations of IL-6, IL-1 beta, and their sample-to-sample fold changes from the 30 hour time point are added to the model using fitted parameters, meaning the coefficients of the linear model.

The final model was selected from the seven total sub-models because it accounted for the highest level of the percentage of variance in the dependent vector. The final model included log(IL-6), log(IL-1 beta), and the logs of their sample-to-sample fold changes as anticipators of time-to-spike. The size of the anticipative window of 36 hours was selected by clinical relevance but is not limited to that anticipative window. The selected model equation is as follows:

Time-to-spike=36.6-8*log(IL6)+2.4*Log(IL-6 fold change)−0.3*Log(IL-1 beta+4.4*Log(TNF alpha)

Figure 27:
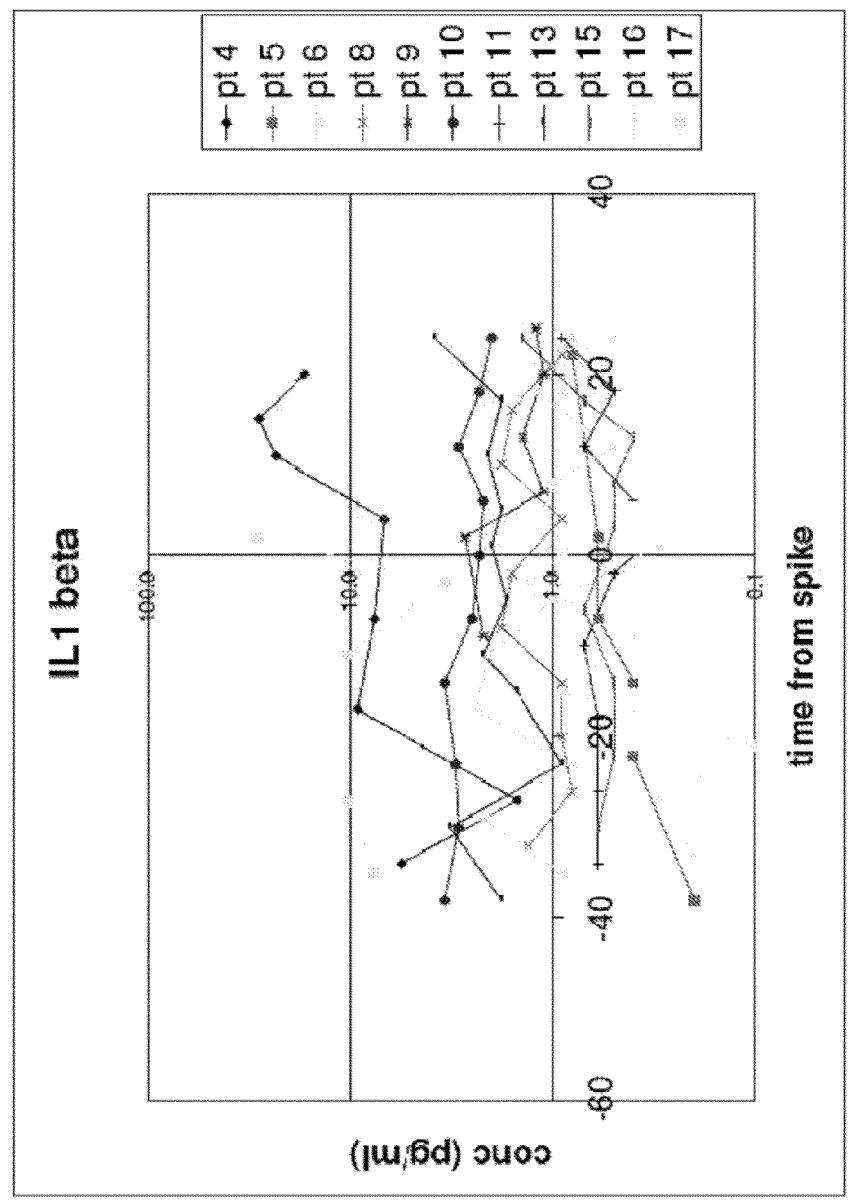
FIG. 27 is the IL-1 beta concentration versus time point number.
Figure 28:
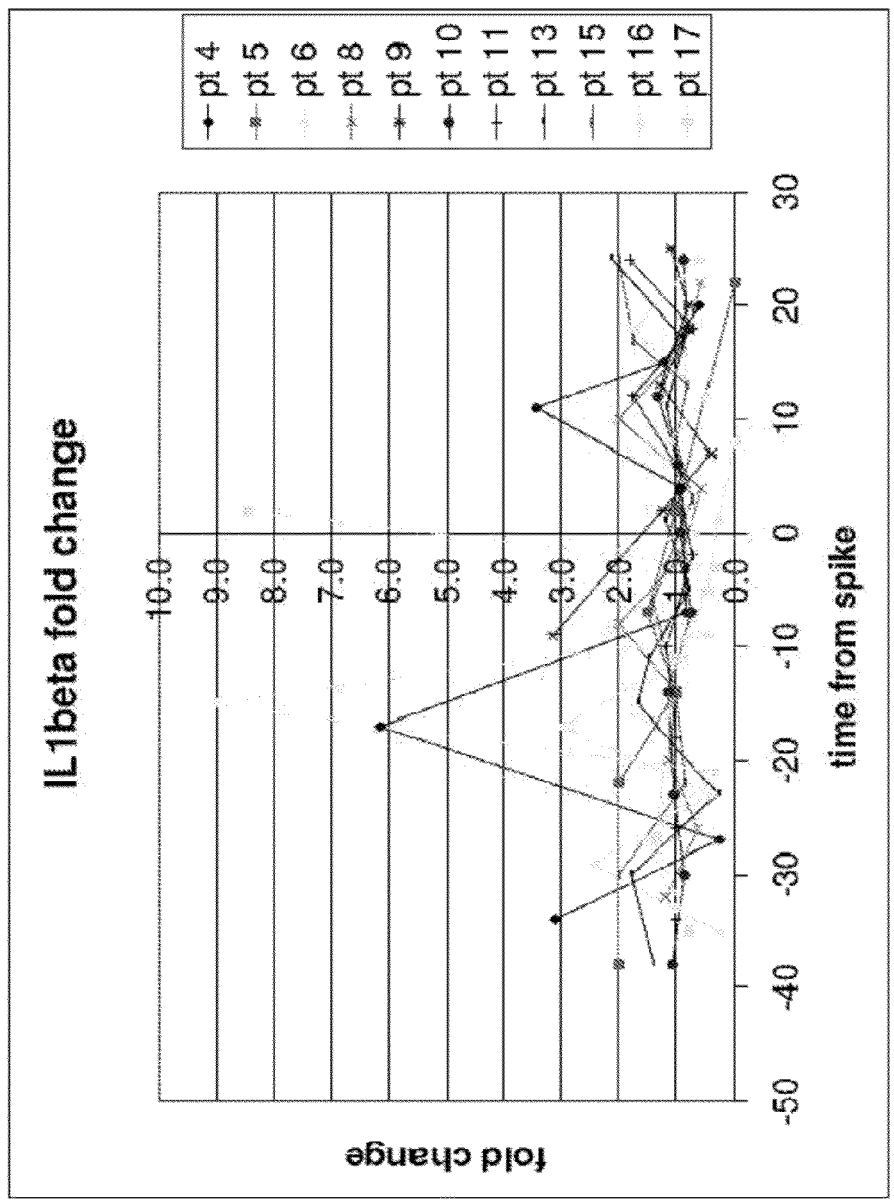
FIG. 28 is the sample-to-sample fold change for IL1-beta versus time point number.
Figure 29:
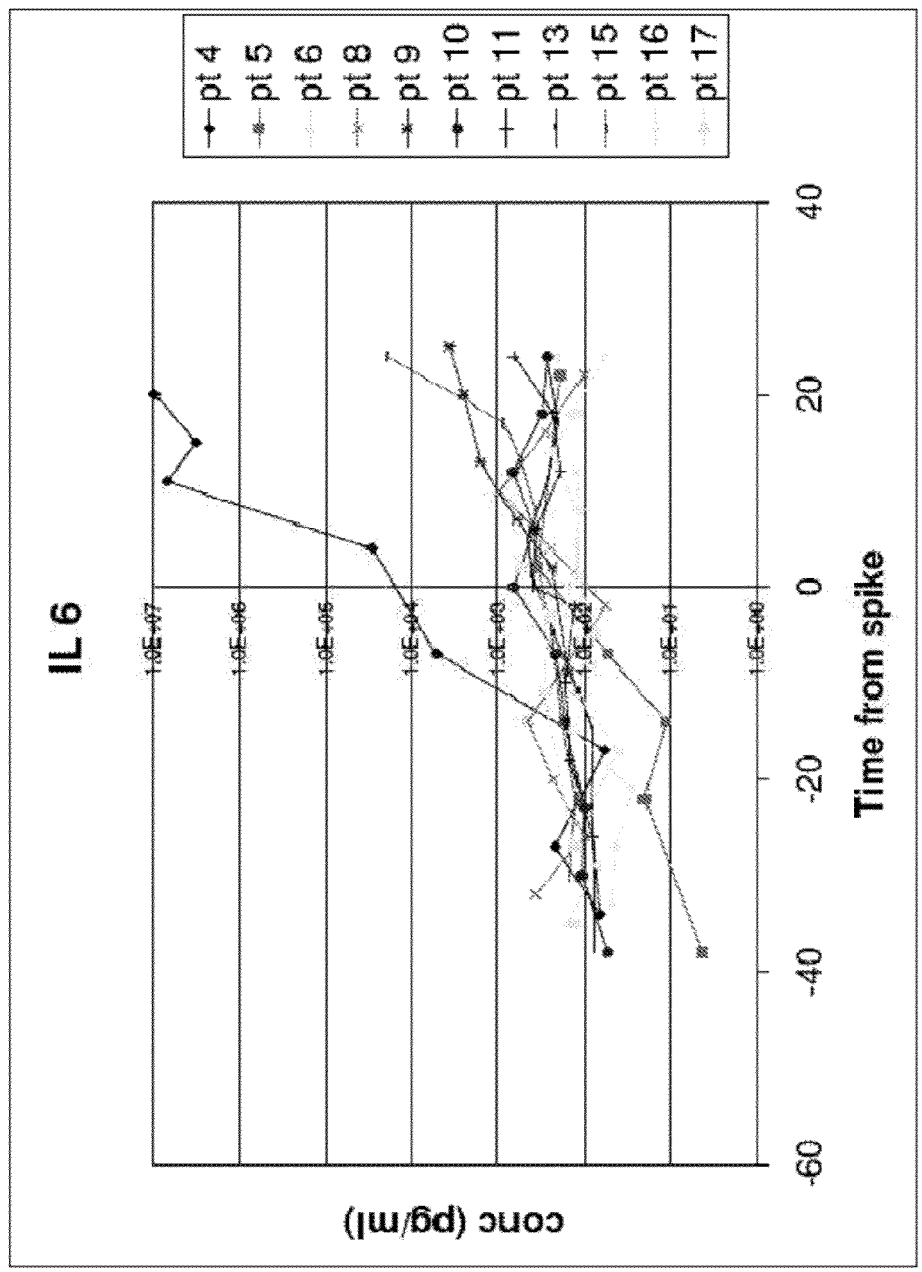
FIG. 29 is the IL-6 concentration versus time point number, wherein patient 4 became septic.
Figure 30:
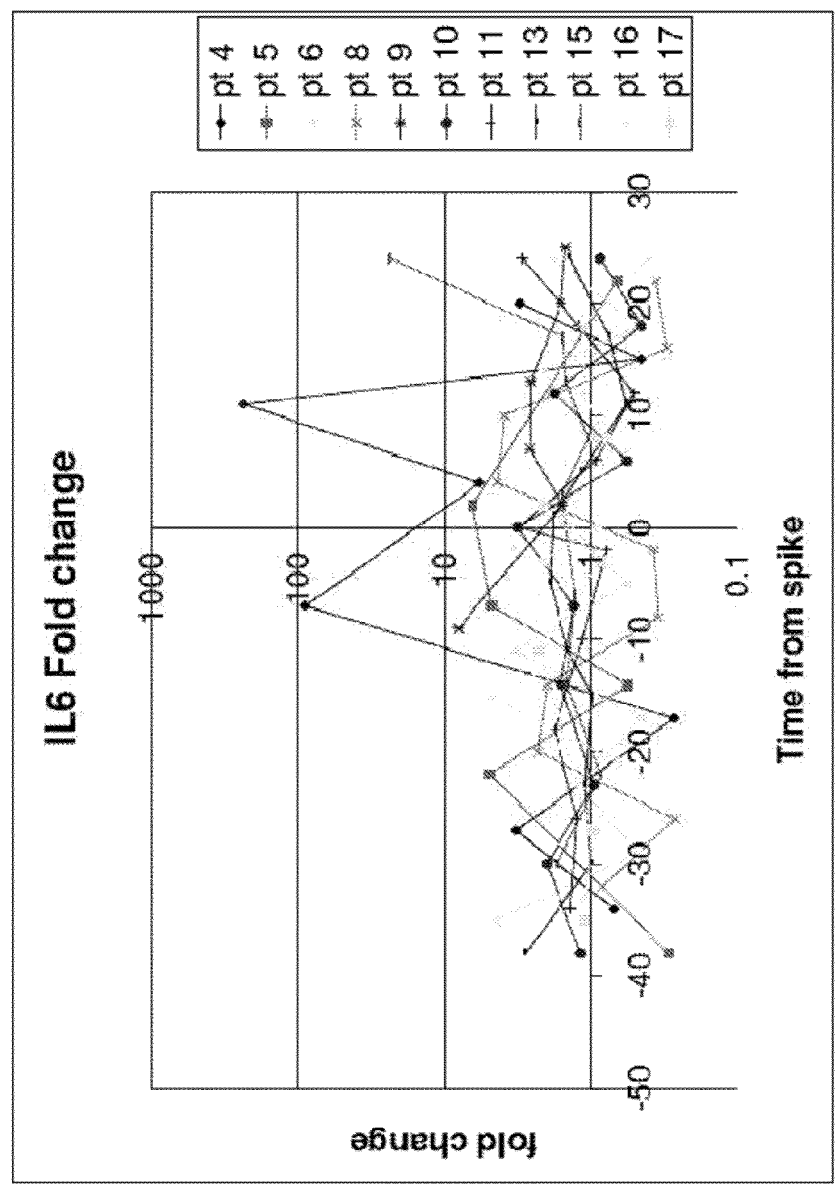
FIG. 30 is the sample-to-sample fold change for IL-6 versus time point number, wherein patient 4 became septic.
Figure 31:
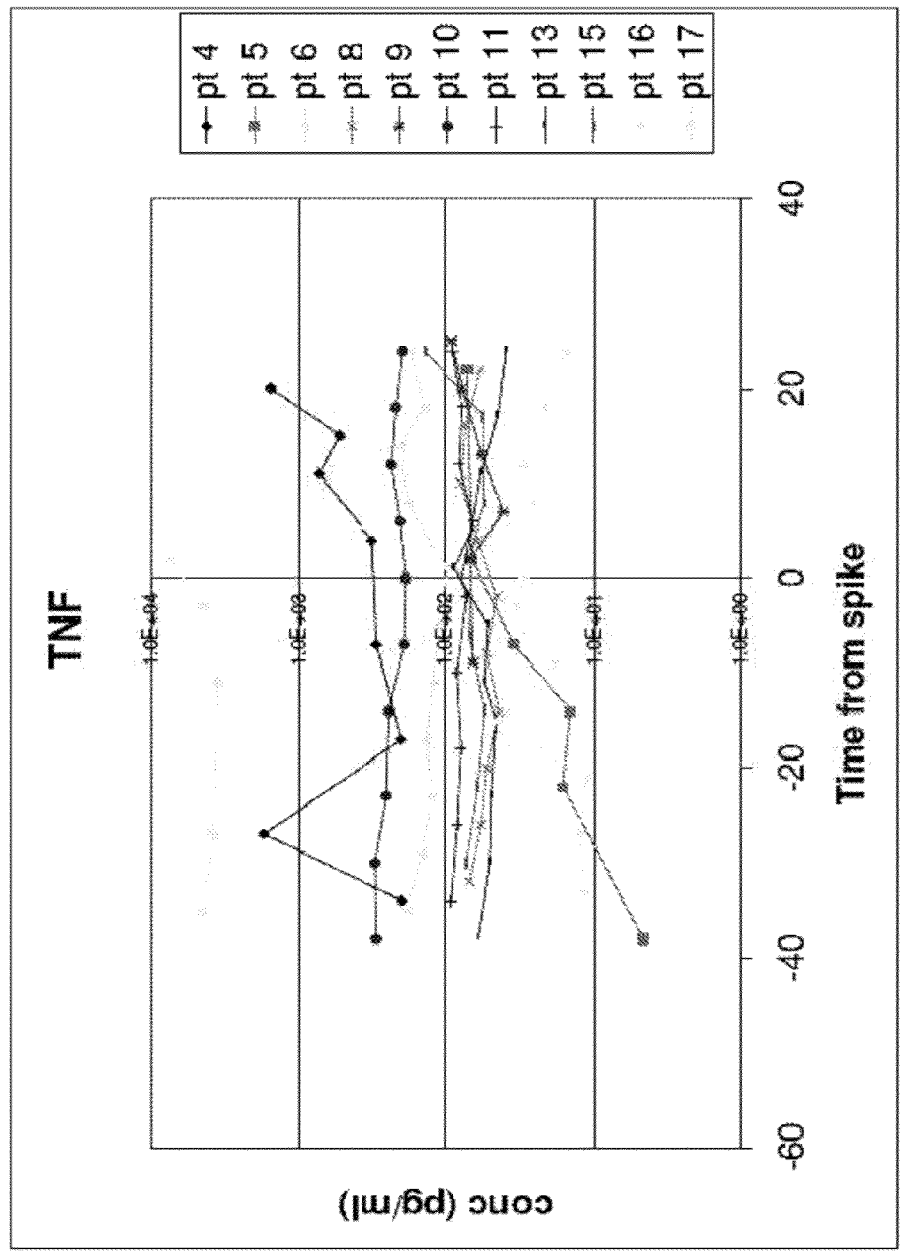
FIG. 31 is the TNF-alpha concentration versus time point number.
Figure 32:
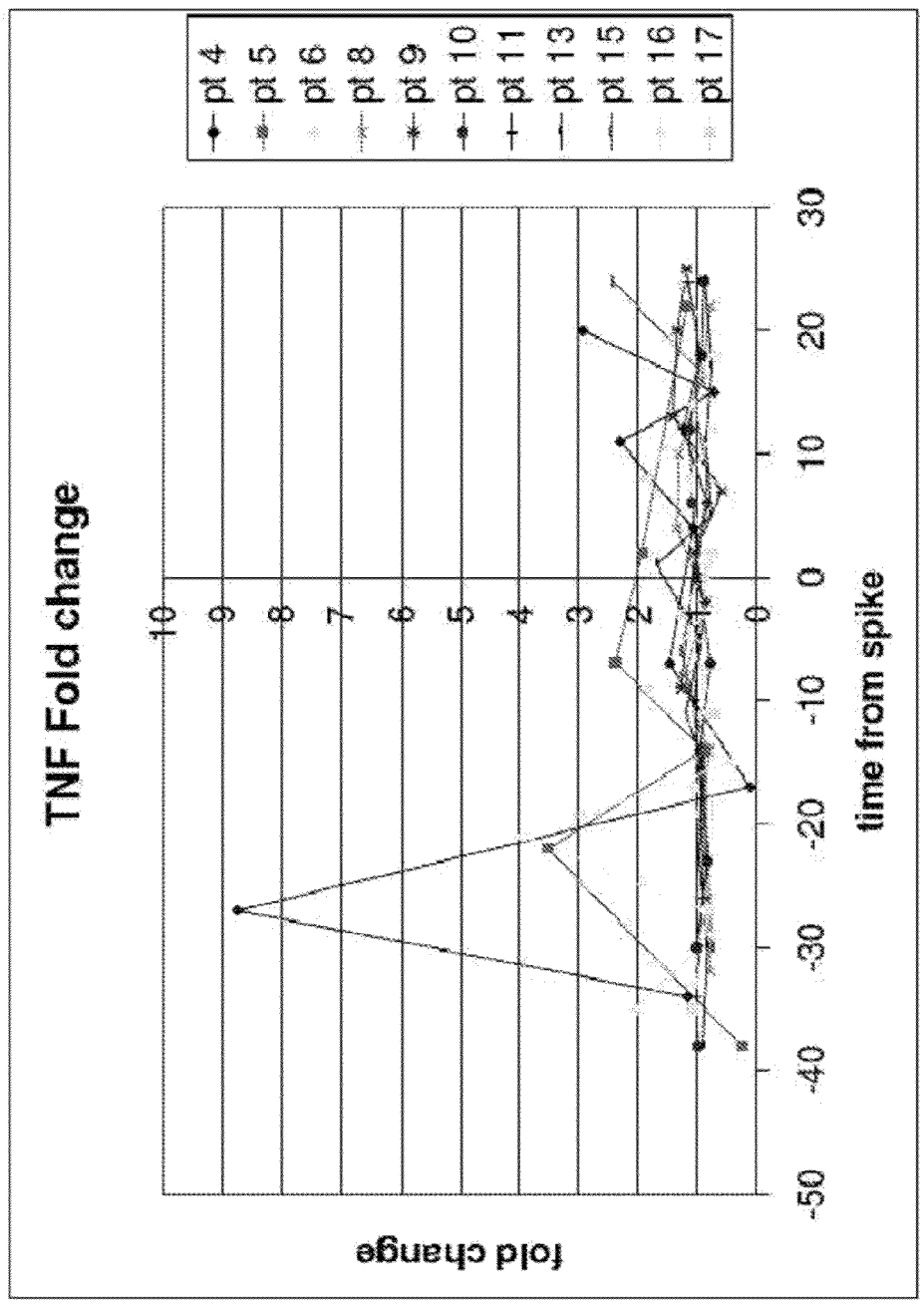
FIG. 32 is the sample-to-sample fold change for TNF-alpha versus time point number.

The results of the 10 patients were evaluated in this example for their biomarker patterns in the 36 hours prior to fever spikes. The data for each of the pyrogens and their sample-to-sample fold changes are in FIGS. 27-32. FIG. 27 is the IL-1 beta concentration versus time point number. FIG. 28 is the sample-to-sample fold change for IL1-beta versus time point number. FIG. 29 is the IL-6 concentration versus time point number, wherein patient 4 became septic. FIG. 30 is the sample-to-sample fold change for IL-6 versus time point number, wherein patient 4 became septic. FIG. 31 is the TNF-alpha concentration versus time point number. FIG. 32 is the sample-to-sample fold change for TNF-alpha versus time point number.

The model anticipated the time-to-spike in all patients and explained the percentage of the variance observed in the dependent variable. Patient 6 had ATRA syndrome and thus is outside the patient population used to construct the model.

Figure 33:
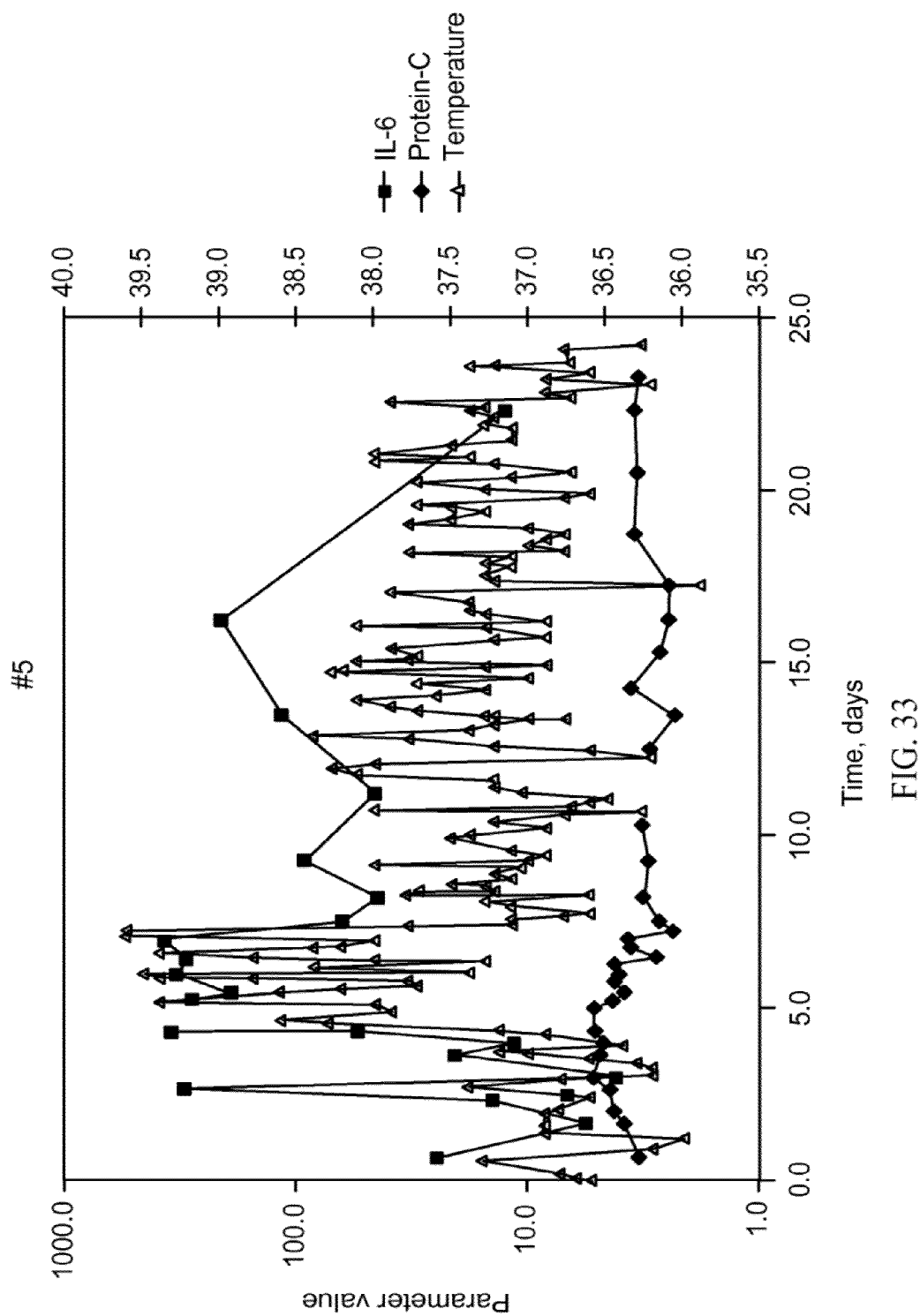
FIG. 33 illustrates the residual plot for Patient 5 who has a fever spike and no decreasing markers.

The residual plot for patient 5 is given in FIG. 33. Patient 5 has a fever spike and no decreasing markers. Temperature in degrees C. (right scale) biomarker concentrations given in pg/mL, wherein IL-6 is a 10-fold increase, not necessarily indicating sepsis. An analysis of the residuals suggest that the model anticipations for the period between 12 and 24 hours prior to the fever spike are non-systematic, meaning randomly distributed about the zero-axis and the size of the residual is no more than the percentage of the anticipated time-to-spike, which is anticipated by the model using the equation 1.

Figure 34:
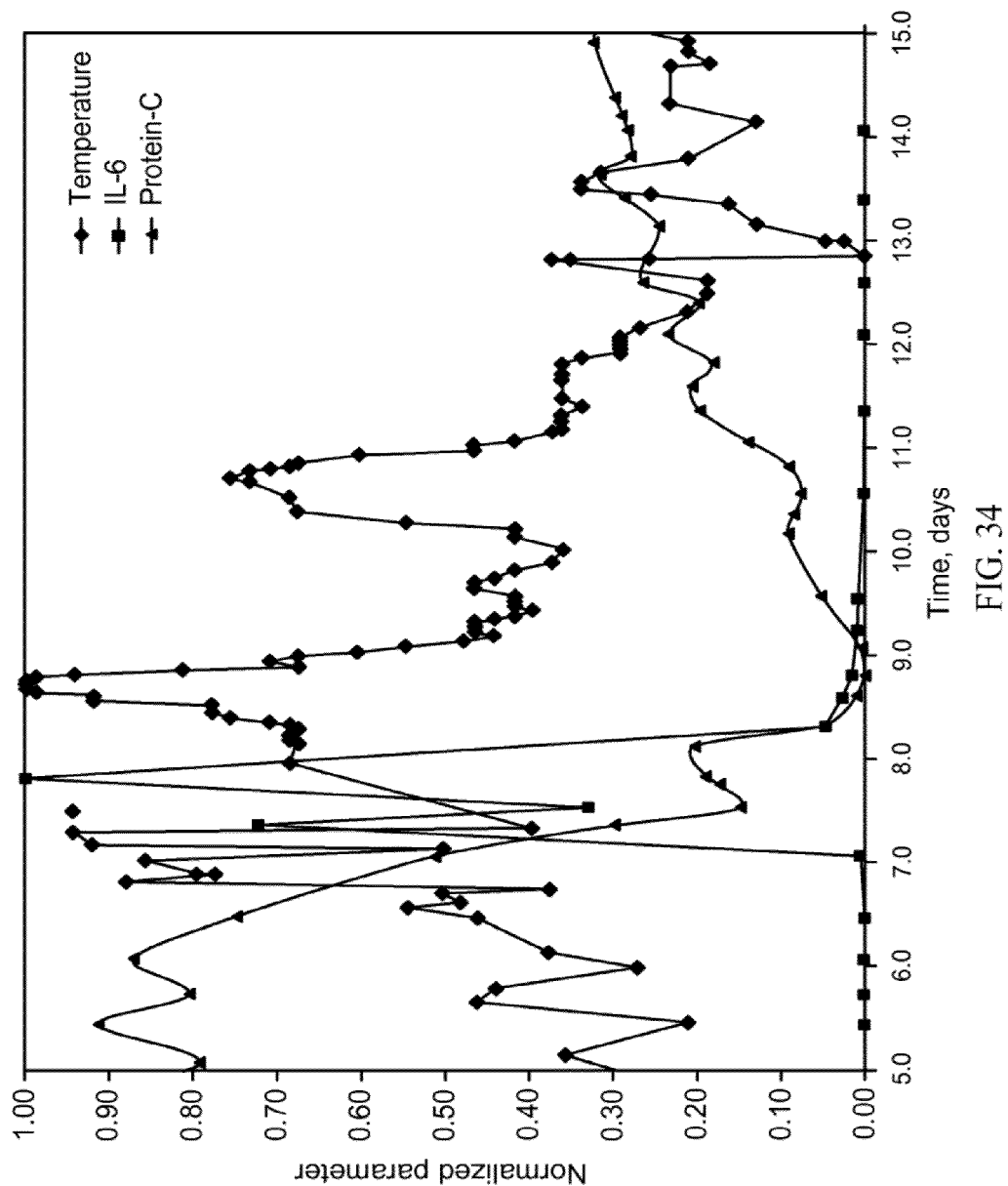
FIG. 34 demonstrates Patient 4 data points showing decreasing Protein-C with increasing IL-6 just prior to fever spike.

For patient 4, the model anticipates a time-to-spike of 3.3 hours when the actual time-to-spike was 7 hours, and, at the other extreme, anticipates a time-to-spike of 31.9 hours when the actual time-to-spike was actually 34 hours as demonstrated in FIG. 34. Patient 4 data points showing decreasing Protein-C with increasing IL-6 just prior to fever spike. Normalized parameter is the ratio of the (parameter value at time t minus the lowest value in the range) to the difference between the maximum and minimum value of the parameter. A residual analysis for Patient 4 yields an excellent fit to the data measured in patient 4, meaning the residuals are randomly distributed about the zero axis, and no residual is greater than 20% of the anticipated time-to-spike, as derived from equation 1.

Figure 35:
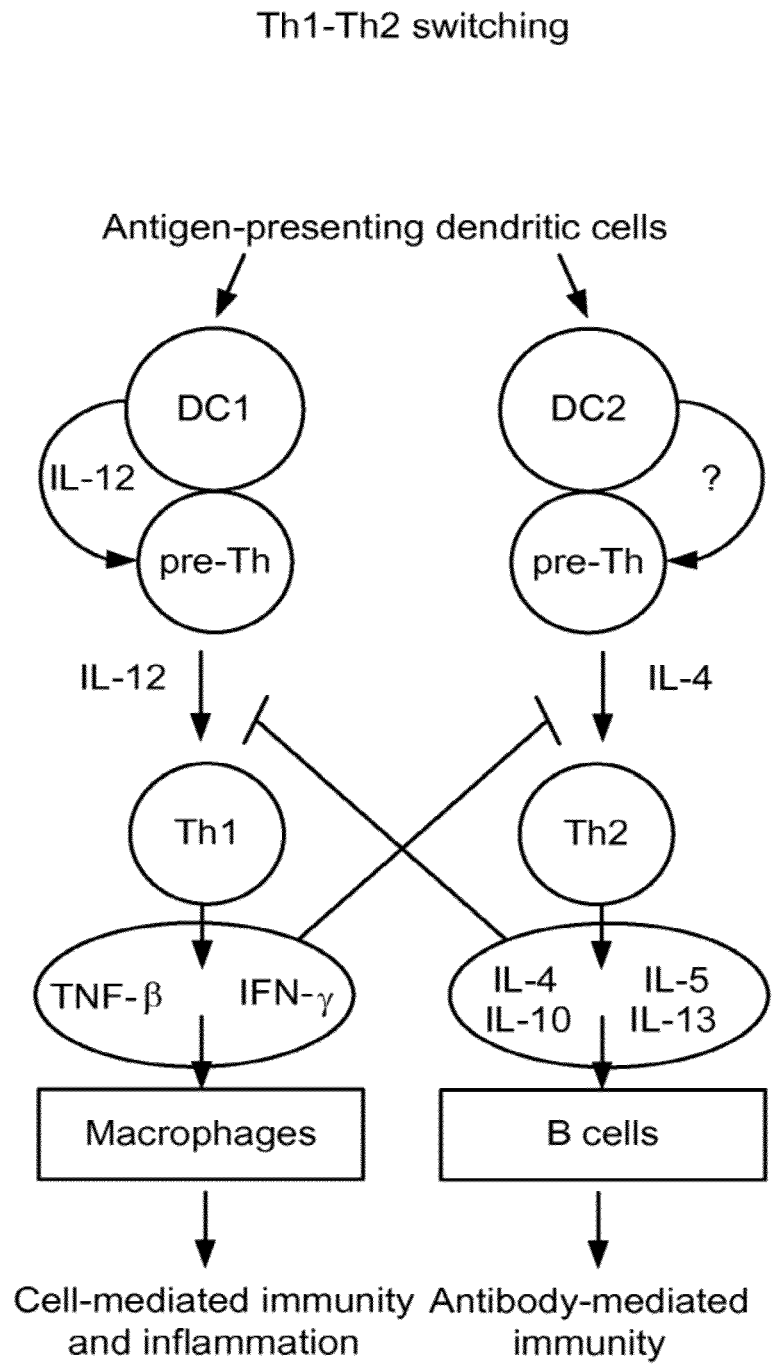
FIG. 35 is a schematic of the Th1-to-Th2 switch and the cytokines representing each phenotype.

In conclusion of this example, induction cancer chemotherapy is only one of the underlying etiologies of sepsis. Others include, but are not limited to, severe burn and thermal injury or traumatic injury. In burn and traumatic injury, the patient expresses an alteration in the immune system resulting in a predominance of the T Helper-2 Lymphocyte phenotype, where the phenotype of the helper cell population switches from Th1 to Th2. This is termed the Th1-to-Th2 switch and makes the patient more susceptible to the onset of infection. FIG. 35 is a schematic of the Th1-to-Th2 switch and the cytokines representing each phenotype. Once the patient becomes infected, if the underlying pathogen is identified, the rate and spread of infection can result in a systemic inflammatory response which is called sepsis. If the pathogen is unidentified, the inflammatory response is termed Systemic Inflammatory Response Syndrome (SIRS). Thus, the underlying etiology of progression to sepsis can be captured as a process divided into three physiologically distinct intervals: Susceptibility to Infection, which is represented by the Th1-Th2 switch, progression through infection, and the onset and progression of sepsis/SIRS. The markers relevant to the monitoring of each stage are shown in Table 3.

TABLE 3

| Sepsis Onset and Sequellae | I. | Sepsis Onset | |
|---|---|---|---|
| | | a. | Protein C** |
| | | b. | IL-1beta** |
| | | c. | IL-6** |
| | | d. | Procalcitonin |
| | | e. | IL-10 |
| | II. | DIC | |
| | | a. | Von Willebrand Factor |
| | | b. | Procalcitonin |
| | | c. | Neopterin |
| | | d. | TNF-α |
| | | e. | Protein C |
| | | f. | PAF1 |
| | | g. | (Pro)Thrombin |
| | III. | ARF (Acute Renal Failure) | |
| | | a. | Creatinine |
| | | b. | Cystin C |
| | IV. | ARDS | |
| | | a. | Von Willebrand Factor |
| | | b. | IL-6 |
| | | c. | Il-8 |
| | | d. | IL-1 |
| | | e. | Il-1ra (IL-1 receptor agonist) |
| | | f. | TNF |
| | V. | ALF (Acute Liver Failure) | |
| | | a. | ALT |
| | | b. | AST |
| | | c. | GGT |
| | | d. | LDH |
| | | e. | Alkaline phosphatase |
| | | f. | Protein C |
| | | g. | Cytokeratin-18 fragments |

Figure 36:
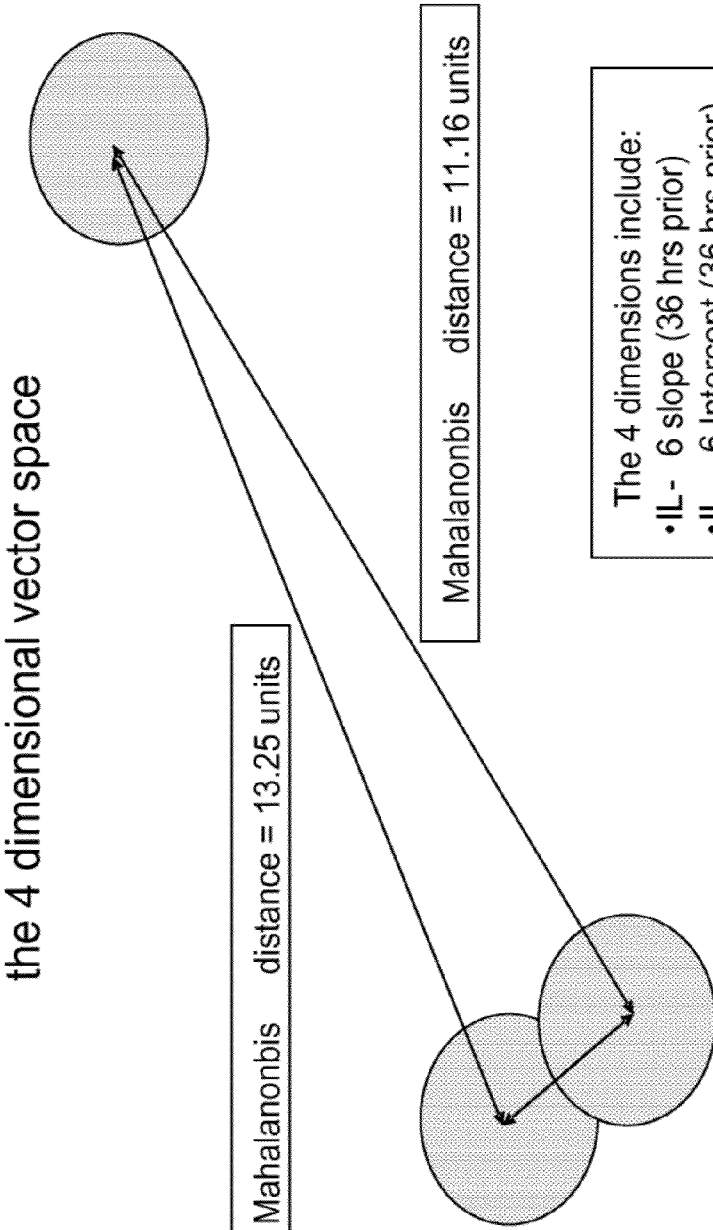
FIG. 36 and FIG. 37 demonstrate that the system uses an equation that is anticipative of sepsis using the Squared Maholanobis distance equation and Bayesian Probability.
Figure 37:
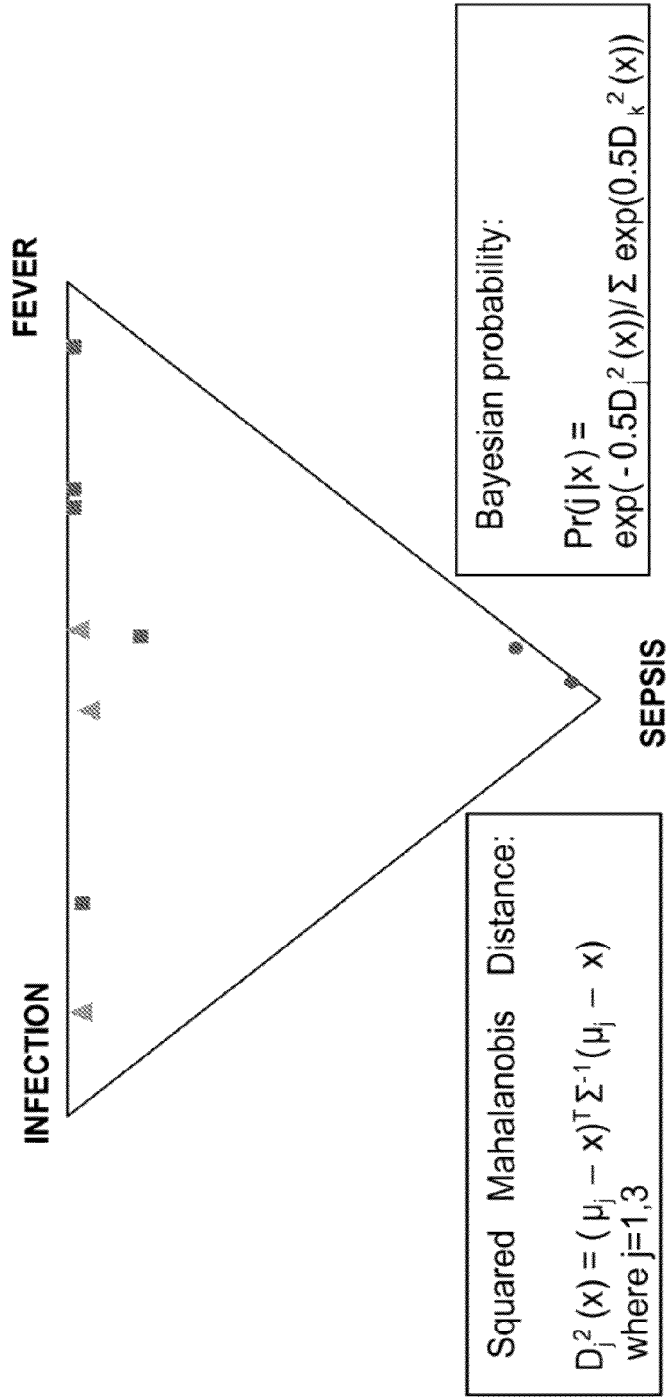

FIG. 36 and FIG. 37 demonstrate that the system uses an equation that is anticipative of sepsis using the Squared Maholanobis distance equation and Bayesian Probability. The Squared Mahalanobis Distance is:

$$D_j^2(x) = (\mu_j - x)^T \Sigma^{-1} (\mu_j) \text{ where } j = 1, 2, 3$$

and the Bayesian probability is:

$$Pr(j|x)=\exp(-0.5\ D_j^2(x))/\Sigma\exp(0.5\ D_k^2(x))$$

wherein μ a is the mean vector representing the centroid of the patient population and j is the three different outcomes (sepsis, fever, infection).

Figure 38:
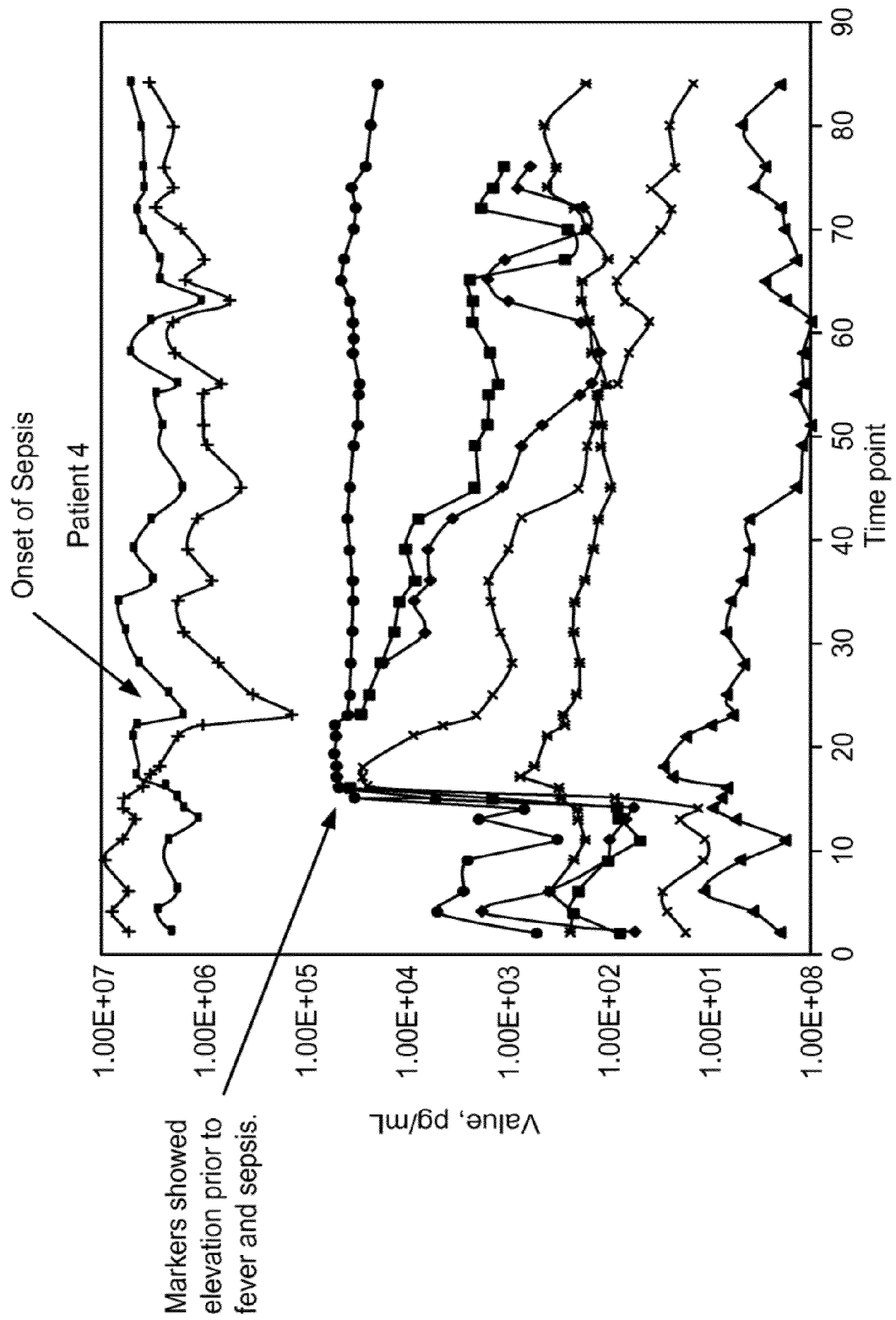
FIG. 38 illustrates a graph in time of a plurality of marker proteins for a patient in a sepsis trial.

FIG. 38 illustrates a graph in time of a plurality of marker proteins for a patient in a sepsis trial. The time of the onset to sepsis for this patient is marked and all patterns leading up to that point are relevant to the determination that this patient became septic.

Figure 39:
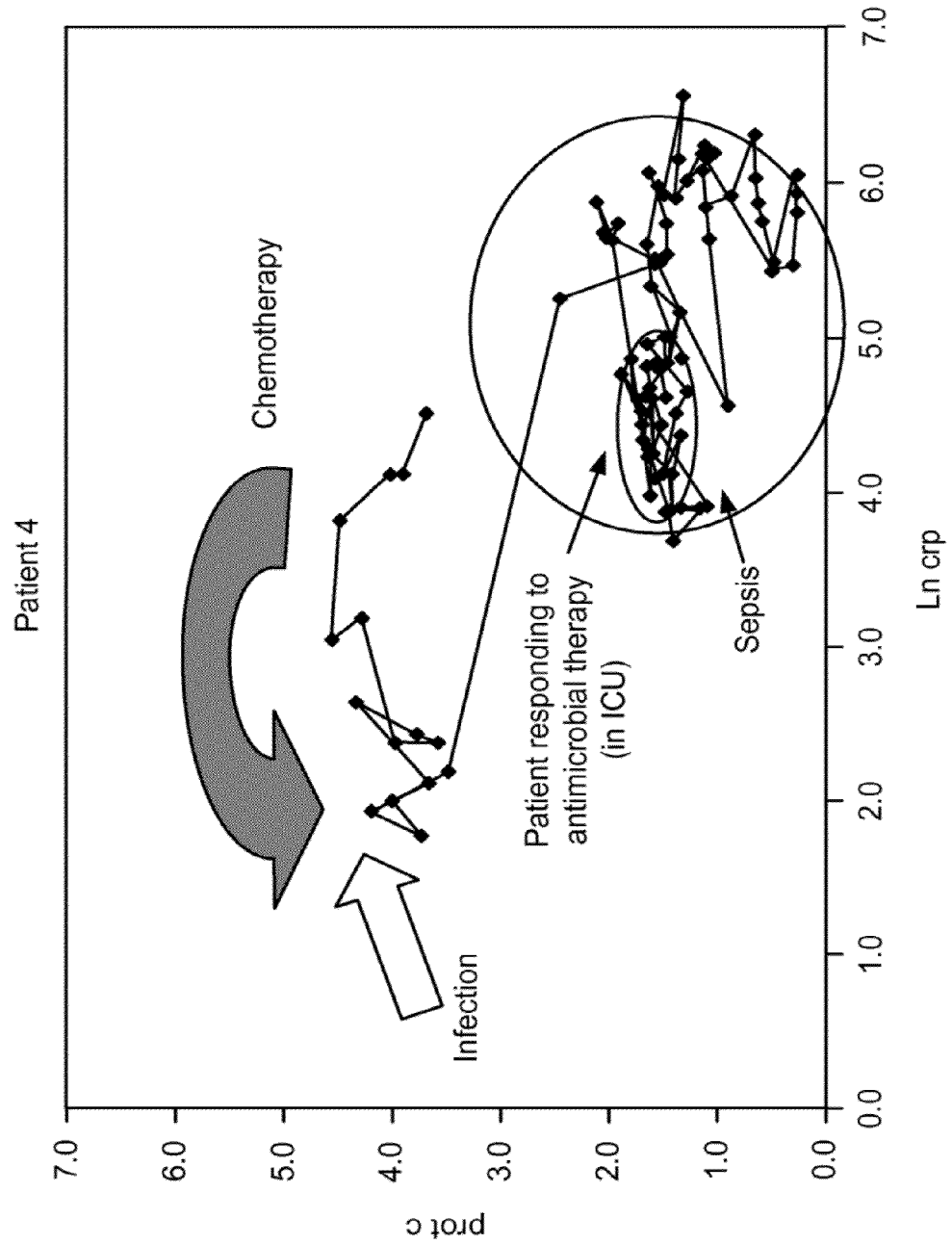
FIG. 39 illustrates a bivariate time course of two particular markers (protein C and C-reactive protein) in the same patient.

FIG. 39 illustrates a bivariate time course of two particular markers (protein C and C-reactive protein) in the same patient. The change in direction in the center of the graph represents a rapid onset of disease. In this example, a patient rapidly deteriorated and was illustrated as septic in a very particular region of the bivariate space. In this example, the sampling intervals are fairly regular; therefore the length of each line segment represents the rate of change of the biomarkers in this particular space.

What is claimed is:

1. A method for characterizing the probability of a clinical outcome of a subject, comprising:
   (a) constructing one or more probability spaces with the aid of a computer processor within a computer system that executes a program to construct said one or more probability spaces, wherein a given probability space is defined by a plurality of discrete clinical outcomes, wherein each discrete clinical outcome of said plurality is characterized by a statistical distribution of a set of markers, wherein at least one discrete clinical outcome of said plurality is characterized by a statistical distribution of a set of markers comprising at least one biological marker, and wherein said given probability space is reflective of a medical condition, medical procedure, therapy, clinical trial, drug discovery, or drug development;
   (b) receiving, with the aid of the computer system, subject data corresponding to the set of markers for each discrete clinical outcome within the given probability space;
   (c) calculating, with the aid of a computer processor that executes a program to determine the position of the subject data in the given probability space, the position of said subject data in said given probability space based on a position of said subject data within each statistical distribution of said set of markers characterizing each said discrete clinical outcome; and
   (d) repeating steps (b) and (c) at multiple time points to determine a velocity or rate of change of said velocity that is indicative of a progression to a given discrete clinical outcome.

2. The method of claim 1, wherein the statistical distribution for a given set of markers is different from all other statistical distributions for all other sets of markers characterizing each of the clinical outcomes within said given probability space.

3. The method of claim 1, wherein step (d) comprises determining a velocity of said progression to said given discrete clinical outcome.

4. The method of claim 1, further comprising notifying a medical personnel or the subject of a need for taking a medical action upon assessing or characterizing the position of said subject data in said probability space.

5. The method of claim 4, wherein the medical action involves at least one action selected from the group consisting of altering a dosage of an existing therapeutic agent administered to said subject, altering the schedule of drug administration, administering a different a therapeutic agent, and administering a different combination of therapeutic agents.

6. The method of claim 5, further comprising, upon selection of at least one action, performing an outcome analysis for assessing a result of said selected action, and automatically updating the probability of a discrete clinical outcome of said subject.

7. The method of claim 1, wherein said plurality of discrete clinical outcomes are selected from the group consisting of complete response (CR), partial response (PR), stable disease (SR), non-response (NR), adverse drug effect (ADR), and drug toxicity.

8. The method of claim 1, further comprising the step of (e) identifying a medical intervention appropriate to achieve or avoid said one of said at least three discrete clinical outcomes indicated by said trajectory.

9. The method of claim 1, wherein said plurality of discrete clinical outcomes comprises at least three discrete clinical outcomes.

10. A method of characterizing a clinical outcome of a subject, comprising:
    (a) constructing, with the aid of a computer processor within a computer system that executes a program to construct a probability space, said probability space defined by a plurality of discrete clinical outcomes, wherein each discrete clinical outcome of said plurality is characterized by a statistical distribution of a set of markers, wherein at least one discrete clinical outcome of said plurality is characterized by a statistical distribution of a set of markers comprising at least one biological marker, and wherein said probability space is reflective of a medical condition, medical procedure, therapy, clinical trial, drug discovery, or drug development;
    (b) providing data of a subject to the computer system, wherein said data corresponds to the set of markers for each discrete clinical outcome within the probability space;
    (c) calculating, with the aid of a computer processor that executes a program to determine the position of the subject data in the probability space, the position of said subject data in said probability space based on a position of said subject data within each statistical distribution of said set of markers characterizing each said discrete clinical outcome; and
    (d) repeating steps (b) and (c) at multiple time points to determine a velocity or rate of change of said velocity that is indicative of a progression to a given discrete clinical outcome.

11. The method of claim 10, further comprising notifying a medical personnel or the subject of a need for taking a medical action upon assessing or characterizing the position of said subject data in said probability space.

12. The method of claim 10, wherein said plurality of discrete clinical outcomes comprises at least three discrete clinical outcomes.

13. The method of claim 10, wherein the statistical distribution for a given set of markers is different from all other statistical distributions for all other sets of markers characterizing each of the clinical outcomes within said given probability space.

14. The method of claim 10 wherein said plurality of discrete clinical outcomes are selected from the group consisting of complete response (CR), partial response (PR), stable disease (SR), non-response (NR), adverse drug effect (ADR), and drug toxicity.

15. A system for subject data analysis, comprising:
(a) a computer processor for executing computer readable instructions, which when executed by said computer processor implements a method, the method comprising:
  (i) constructing one or more probability spaces with the aid of a computer processor that executes a program to construct said one or more probability spaces, wherein a given probability space is defined by a plurality of discrete clinical outcomes, wherein each discrete clinical outcome of said plurality is characterized by a statistical distribution of a set of markers, wherein at least one discrete clinical outcome of said plurality is characterized by a statistical distribution of a set of markers comprising at least one biological marker, and wherein said given probability space is reflective of a medical condition, medical procedure, therapy, clinical trial, drug discovery, or drug development;
  (ii) receiving, with the aid of a computer, subject data corresponding to the set of markers for each discrete clinical outcome within the given probability space;
  (iii) calculating, with the aid of a computer processor that executes a program to determine the position of the subject data in the given probability space, the position of said subject data in said given probability space based on a position of said subject data within each statistical distribution of said set of markers characterizing each said discrete clinical outcome; and
  (iv) repeating steps (ii) and (iii) at multiple time points to determine a velocity or rate of change of said velocity that is indicative of a progression to a given discrete clinical outcome;
(b) an electronic storage unit in communication with the computer processor, wherein the storage unit:
  (i) stores data corresponding to said given probability space; and
  (ii) stores subject data corresponding to said set of markers.

16. The system of claim 15, further comprising an input device that is in communication with said computer processor, wherein said input device is for receiving said subject data.

17. The system of claim 15, further comprising an output device that transmits information relating to said given discrete clinical outcome to an end user.

18. The system of claim 17, wherein said end user is a health care provider.

19. The system of claim 17, wherein said output device transmits selected portions of the subject data and/or the probability space in response to instructions from the end user.

20. The system of claim 17, wherein the information transmitted by the output device represents an assessment of said progression.

21. The system of claim 15, wherein the electronic storage unit stores historical reference data of a plurality of subjects in relationship to said set of markers for each discrete clinical outcome.

22. The system of claim 15, wherein the data stored in the electronic storage unit are selected from the categories consisting of pathology, anatomy, treatment option, treatment outcome, pharmacological parameter, pharmacokinetics parameter, psychological parameter, and genomic information.

23. The system of claim 15, wherein the subject data represent measurements of one or more markers present in a bodily fluid.

24. The system of claim 15, wherein said plurality of discrete clinical outcomes comprises at least three discrete clinical outcomes.

* * * * *